US006451536B1

(12) United States Patent
Fodor et al.

(10) Patent No.: US 6,451,536 B1
(45) Date of Patent: *Sep. 17, 2002

(54) PRODUCTS FOR DETECTING NUCLEIC ACIDS

(75) Inventors: Stephen P. A. Fodor, Palo Alto; Dennis W. Solas, San Francisco; William J. Dower, Menlo Park, all of CA (US)

(73) Assignee: Affymetrix Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/670,563

(22) Filed: Sep. 27, 2000

Related U.S. Application Data

(63) Continuation of application No. 09/362,089, filed on Jul. 28, 1999, which is a division of application No. 09/056,927, filed on Apr. 8, 1998, now Pat. No. 6,197,506, which is a continuation of application No. 08/670,118, filed on Jun. 25, 1996, now Pat. No. 5,800,992, which is a division of application No. 08/168,904, filed on Dec. 15, 1993, now abandoned, which is a continuation of application No. 07/624,114, filed on Dec. 6, 1990, now abandoned.

(51) Int. Cl.[7] .............................. C12Q 1/68; C12M 1/34; C07H 21/04; C07H 21/02
(52) U.S. Cl. ....................... 435/6; 435/288.3; 536/23.1; 536/24.3
(58) Field of Search .................. 435/288.3, 6; 536/23.1, 536/24.3

(56) References Cited

U.S. PATENT DOCUMENTS

| | | |
|---|---|---|
| 3,849,137 A | 11/1974 | Barzynski et al. |
| 3,862,056 A | 1/1975 | Hartman |
| 3,939,350 A | 2/1976 | Kronick et al. |
| 4,072,576 A | 2/1978 | Arwin et al. |
| 4,180,739 A | 12/1979 | Abu-Shumays |
| 4,238,757 A | 12/1980 | Schenck |
| 4,269,933 A | 5/1981 | Pazos |
| 4,314,821 A | 2/1982 | Rice |
| 4,327,073 A | 4/1982 | Huang |
| 4,339,528 A | 7/1982 | Goldman |
| 4,342,905 A | 8/1982 | Fujii et al. |
| 4,373,071 A | 2/1983 | Itakura |
| 4,405,771 A | 9/1983 | Jagur |
| 4,444,878 A | 4/1984 | Paulus |
| 4,444,892 A | 4/1984 | Malmros |

(List continued on next page.)

FOREIGN PATENT DOCUMENTS

| | | |
|---|---|---|
| DE | 2242394 | 3/1974 |
| DE | 3440141 | 5/1986 |
| DE | 3505287 | 3/1988 |
| DE | 3722958 | 1/1989 |
| EP | 046 083 | 2/1982 |
| EP | 088 636 | 9/1983 |
| EP | 103 197 | 3/1984 |
| EP | 127 438 | 12/1984 |
| EP | 063 810 | 3/1986 |
| EP | 194 132 | 9/1986 |
| EP | 228 075 | 7/1987 |
| EP | 245 662 | 11/1987 |
| EP | 268 237 | 5/1988 |
| EP | 281 927 | 9/1988 |
| EP | 228 310 | 10/1988 |

(List continued on next page.)

OTHER PUBLICATIONS

Durland et al, Bioconjugate Chem., 6:278–282 (1995).
Sequencing by Hybridization Workshop, listing of participants and workshop presentation summaries (1991).
"A Sequencing Reality Check," Science, 242:1245 (1988).
"Affymax raises $25 million to develop high–speed drug discovery system," Biotechnology News, 10(3):7–8 (1990).
"Preparation of fluorescent–labeled DNA and its use as a probe in molecular hybridization," Bioorg Khim, 12(11):1508–1513 (1986).
Abbott et al., "Manipulation of the Wettability of Surfaces on the 0.1–to1–Micrometer Scale Through Micromachining and Molecular Self–Assembly," Science, 257:1380–1382 (1992).
Adams et al., "Complementary DNA Sequencing: Expressed Sequence Tags and Human Genome Project," Science, 252(5013):1651–1656 (1991).
Adams et al., "Photolabile Chelators That "Cage" Calcium with Improved Speed of Release and Pre–Photolysis Affinity," J. Gen Physiol., p. 9a (12/86).
Adams et al., "Biologically Useful Chelators That Take Up Ca2+ upon Illumination," J. Am. Chem. Soc., 111:7957–7968 (1989).
Amit et al., "Photosensitive Protecting Groups of Amino Sugars and Their Use in Glycoside Synthesis. 2–Nitrobenzyloxycarbonylamino and 6–Nitroveratryloxycarbonylamino Derivatives," J. Org.Chem, 39(2):192–196 (1974).
Amit et al., "Photosensitive Protecting Groups—A Review," Israel J. Chem., 12(1–2):103–113 (1974).
Applied Biosystems, Model 431A Peptide Synthesizer User's manual, Sections 2 and 6, (Aug. 15, 1989).
Ajayaghosh et al., "Solid–Phase Synthesis of N–Methyl– and N–Ethylamides of Peptides Using Photolytically Detachable ((3–Nitro–4((alkylamino)methyl)benzamido) methylpolystyrene Resin," J.Org.Chem., 55(9):2826–2829 (1990).
Ajayaghosh et al., "Solid–phase synthesis of C–terminal peptide amides using a photoremovable α–methylphenacylamido anchoring linkage," Proc. Ind. Natl. Sci (Chem.Sci.), 100(5):389–396 (1988).

(List continued on next page.)

Primary Examiner—Stephanie Zitomer
(74) Attorney, Agent, or Firm—Morgan, Lewis & Bockius LLP.

(57) ABSTRACT

The present invention provides methods and apparatus for sequencing, fingerprinting and mapping biological macromolecules, typically biological polymers. The methods make use of a plurality of sequence specific recognition reagents which can also be used for classification of biological samples, and to characterize their sources.

27 Claims, 2 Drawing Sheets

U.S. PATENT DOCUMENTS

| | | |
|---|---|---|
| 4,448,534 A | 5/1984 | Wertz et al. |
| 4,458,066 A | 7/1984 | Caruthers et al. |
| 4,483,920 A | 11/1984 | Gillespie et al. |
| 4,500,707 A | 2/1985 | Caruthers et al. |
| 4,516,833 A | 5/1985 | Fusek |
| 4,517,338 A | 5/1985 | Urdea et al. |
| 4,537,861 A | 8/1985 | Elings et al. |
| 4,542,102 A | 9/1985 | Dattagupta et al. |
| 4,555,490 A | 11/1985 | Merril |
| 4,562,157 A | 12/1985 | Lowe et al. |
| 4,569,967 A | 2/1986 | Kornreich et al. |
| 4,580,895 A | 4/1986 | Patel |
| 4,584,277 A | 4/1986 | Ullman |
| 4,613,566 A | 9/1986 | Potter |
| 4,624,915 A | 11/1986 | Schindler et al. |
| 4,626,684 A | 12/1986 | Landa |
| 4,631,211 A | 12/1986 | Houghten |
| 4,637,861 A | 1/1987 | Krull et al. |
| 4,677,054 A | 6/1987 | White et al. |
| 4,681,859 A | 7/1987 | Kramer |
| 4,683,202 A | 7/1987 | Mullis |
| 4,689,405 A | 8/1987 | Frank et al. |
| 4,704,353 A | 11/1987 | Humphries et al. |
| 4,711,955 A | 12/1987 | Ward et al. |
| 4,713,326 A | 12/1987 | Dattagupta et al. |
| 4,713,347 A | 12/1987 | Mitchell et al. |
| 4,719,615 A | 1/1988 | Feyrer et al. |
| 4,722,906 A | 2/1988 | Guire |
| 4,728,502 A | 3/1988 | Hamill |
| 4,728,591 A | 3/1988 | Clark et al. |
| 4,731,325 A | 3/1988 | Palva et al. |
| 4,755,458 A | 7/1988 | Rabbani et al. |
| 4,762,881 A | 8/1988 | Kauer |
| 4,777,019 A | 10/1988 | Dandekar |
| 4,780,504 A | 10/1988 | Buendia et al. |
| 4,786,170 A | 11/1988 | Groebler |
| 4,786,684 A | 11/1988 | Glass |
| 4,794,150 A | 12/1988 | Steel |
| 4,806,631 A * | 2/1989 | Carrico et al. ............. 536/23.1 |
| 4,808,508 A | 2/1989 | Platzer |
| 4,810,869 A | 3/1989 | Yabe et al. |
| 4,811,062 A | 3/1989 | Tabata et al. |
| 4,812,512 A | 3/1989 | Buendia et al. |
| 4,820,630 A | 4/1989 | Taub |
| 4,822,566 A | 4/1989 | Newman |
| 4,822,681 A * | 4/1989 | Schossler et al. ............ 428/405 |
| 4,833,092 A | 5/1989 | Geysen |
| 4,844,617 A | 7/1989 | Kelderman et al. |
| 4,846,552 A | 7/1989 | Veldkamp et al. |
| 4,849,513 A | 7/1989 | Smith et al. |
| 4,855,225 A | 8/1989 | Fung et al. |
| 4,865,990 A | 9/1989 | Stead et al. |
| 4,868,103 A | 9/1989 | Stavrianopoulos et al. |
| 4,874,500 A | 10/1989 | Madou et al. |
| 4,886,741 A | 12/1989 | Schwartz |
| 4,888,278 A | 12/1989 | Singer et al. |
| 4,923,901 A | 5/1990 | Koester et al. |
| 4,925,785 A | 5/1990 | Wang et al. |
| 4,946,942 A | 8/1990 | Fuller et al. |
| 4,965,188 A | 10/1990 | Mullis |
| 4,973,493 A | 11/1990 | Guire |
| 4,979,959 A | 12/1990 | Guire |
| 4,981,783 A | 1/1991 | Augelicht |
| 4,981,985 A | 1/1991 | Kaplan et al. |
| 4,984,100 A | 1/1991 | Takayama et al. |
| 4,987,065 A | 1/1991 | Stavrianopoulos et al. |
| 4,988,617 A | 1/1991 | Landegren et al. |
| 4,992,383 A | 2/1991 | Farnsworth |
| 4,994,373 A | 2/1991 | Stavrianopoulos et al. |
| 5,002,867 A | 3/1991 | Macevicz |
| 5,021,550 A | 6/1991 | Zeiger |
| 5,026,773 A | 6/1991 | Steel |
| 5,026,840 A | 6/1991 | Dattagupta et al. |
| 5,028,525 A | 7/1991 | Gray et al. |
| 5,043,265 A | 8/1991 | Tanke et al. |
| 5,047,524 A | 9/1991 | Andrus et al. |
| 5,075,077 A | 12/1991 | Durley |
| 5,077,210 A | 12/1991 | Eigler |
| 5,079,600 A | 1/1992 | Schnur et al. |
| 5,081,584 A | 1/1992 | Omichinski et al. |
| 5,082,830 A | 1/1992 | Brakel et al. |
| 5,091,652 A | 2/1992 | Mathies et al. |
| 5,112,962 A | 5/1992 | Letsinger et al. |
| 5,141,813 A | 8/1992 | Nelson |
| 5,143,854 A | 9/1992 | Pirrung et al. |
| 5,153,319 A | 10/1992 | Caruthers et al. |
| 5,192,980 A | 3/1993 | Dixon et al. |
| 5,200,051 A | 4/1993 | Cozzette et al. |
| 5,202,231 A | 4/1993 | Drmanac et al. |
| 5,206,137 A | 4/1993 | Ip et al. |
| 5,215,882 A | 6/1993 | Bahl et al. |
| 5,215,889 A | 6/1993 | Schultz |
| 5,217,866 A | 6/1993 | Summerton et al. ............ 435/6 |
| 5,232,829 A | 8/1993 | Longiaru et al. |
| 5,235,028 A | 8/1993 | Barany et al. |
| 5,242,974 A | 9/1993 | Holmes |
| 5,252,743 A | 10/1993 | Barrett et al. |
| 5,256,549 A | 10/1993 | Urdea et al. |
| 5,258,506 A | 11/1993 | Urdea et al. |
| 5,306,641 A | 4/1994 | Saccocio |
| 5,310,893 A | 5/1994 | Erlich et al. |
| 5,324,633 A | 6/1994 | Fodor et al. |
| 5,348,855 A | 9/1994 | Dattagupta et al. |
| 5,384,261 A | 1/1995 | Winkler et al. |
| 5,405,783 A | 4/1995 | Pirrung et al. |
| 5,412,087 A | 5/1995 | McGall et al. ............. 536/24.3 |
| 5,424,186 A | 6/1995 | Fodor et al. |
| 5,436,327 A | 7/1995 | Southern et al. |
| 5,445,934 A | 8/1995 | Fodor et al. |
| 5,447,841 A | 9/1995 | Gray et al. |
| 5,451,505 A | 9/1995 | Dollinger |
| 5,474,796 A | 12/1995 | Brennan ..................... 427/2.13 |
| 5,484,908 A | 1/1996 | Froehler et al. ......... 536/24.31 |
| 5,486,452 A | 1/1996 | Gordon et al. |
| 5,489,507 A | 2/1996 | Chehab |
| 5,489,678 A | 2/1996 | Fodor et al. |
| 5,492,806 A | 2/1996 | Drmanac et al. |
| 5,510,270 A | 4/1996 | Fodor et al. |
| 5,525,464 A | 6/1996 | Drmanac et al. |
| 5,527,681 A | 6/1996 | Holmes |
| 5,552,270 A | 9/1996 | Khrapko et al. |
| 5,556,752 A | 9/1996 | Lockhart et al. ................ 435/6 |
| 5,556,961 A | 9/1996 | Foote et al. |
| 5,561,071 A | 10/1996 | Hollenberg et al. |
| 5,565,324 A | 10/1996 | Still |
| 5,567,809 A | 10/1996 | Apple |
| 5,571,639 A | 11/1996 | Hubbell et al. |
| 5,573,905 A | 11/1996 | Lerner |
| 5,593,839 A | 1/1997 | Hubbell et al. |
| 5,604,097 A | 2/1997 | Brenner ......................... 435/6 |
| 5,635,400 A | 6/1997 | Brenner |
| 5,641,634 A | 6/1997 | Mandecki |
| 5,653,939 A | 8/1997 | Hollis et al. |
| 5,654,413 A | 8/1997 | Brenner |
| 5,667,667 A | 9/1997 | Southern |
| 5,667,972 A | 9/1997 | Drmanac et al. |
| 5,690,894 A | 11/1997 | Pinkel |
| 5,695,940 A | 12/1997 | Drmanac et al. |
| 5,698,393 A | 12/1997 | Macioszek et al. |
| 5,700,637 A | 12/1997 | Southern |
| 5,707,806 A | 1/1998 | Shuber |

| | | |
|---|---|---|
| 5,744,305 A | 4/1998 | Fodor et al. |
| 5,751,629 A | 5/1998 | Nova |
| 5,770,367 A | 6/1998 | Southern |
| 5,777,888 A | 7/1998 | Rine et al. |
| 5,800,992 A | 9/1998 | Fodor et al. |
| 5,804,563 A | 9/1998 | Still |
| 5,807,522 A | 9/1998 | Brown et al. |
| 5,807,683 A | 9/1998 | Brenner |
| 5,830,645 A | 11/1998 | Pinkel et al. |
| 5,843,767 A | 12/1998 | Beattie |
| 5,846,708 A | 12/1998 | Hollis et al. |
| 5,846,719 A | 12/1998 | Brenner |
| 5,863,722 A | 1/1999 | Brenner |
| 5,871,697 A | 2/1999 | Rothberg et al. |
| 6,023,540 A | 2/2000 | Walt |
| 6,054,270 A | 4/2000 | Southern |
| 6,060,240 A | 5/2000 | Kamb |

FOREIGN PATENT DOCUMENTS

| | | |
|---|---|---|
| EP | 288 310 | 10/1988 |
| EP | 304 202 | 2/1989 |
| EP | 307 476 | 3/1989 |
| EP | 319 012 | 6/1989 |
| EP | 328 256 | 8/1989 |
| EP | 333 561 | 9/1989 |
| EP | 337 498 | 10/1989 |
| EP | 386 229 | 4/1990 |
| EP | 373 203 | 6/1990 |
| EP | 392 546 | 10/1990 |
| EP | 173 339 | 1/1992 |
| EP | 171 150 | 3/1992 |
| EP | 237 362 | 3/1992 |
| EP | 185 547 | 6/1992 |
| EP | 260 634 | 6/1992 |
| EP | 232 967 | 4/1993 |
| EP | 235 726 | 5/1993 |
| EP | 476 014 | 8/1994 |
| EP | 225 807 | 10/1994 |
| EP | 717 113 | 6/1996 |
| EP | 0 721 016 | 7/1996 |
| EP | 848 067 | 6/1998 |
| EP | 619 321 | 1/1999 |
| FR | 2559783 | 3/1988 |
| GB | 2 129 551 | 5/1984 |
| GB | 2156074 | 3/1988 |
| GB | 2196476 | 4/1988 |
| GB | 8810400.5 | 5/1988 |
| GB | 2233654 | 1/1991 |
| GB | 2248840 | 9/1992 |
| JP | 49-110601 | 10/1974 |
| JP | 60-248669 | 12/1985 |
| JP | 63-084499 | 4/1988 |
| JP | 63-223557 | 9/1988 |
| JP | 1-233447 | 9/1989 |
| NO | P 913186 | 8/1991 |
| WO | WO 84/03151 | 8/1984 |
| WO | WO 84/03564 | 9/1984 |
| WO | WO 85/01051 | 3/1985 |
| WO | WO 86/00991 | 2/1986 |
| WO | WO 86/05518 | 9/1986 |
| WO | WO 86/06487 | 11/1986 |
| WO | WO 88/04777 | 6/1988 |
| WO | WO 89/05616 | 6/1989 |
| WO | WO 89/08834 | 9/1989 |
| WO | WO 89/10977 | 11/1989 |
| WO | WO 89/11548 | 11/1989 |
| WO | WO 89/12819 | 12/1989 |
| WO | WO 90/00626 | 1/1990 |
| WO | WO 90/00887 | 2/1990 |
| WO | WO 90/15070 | 2/1990 |
| WO | WO 90/03382 | 4/1990 |
| WO | WO 90/04652 | 5/1990 |
| WO | WO 91/04266 | 4/1991 |
| WO | WO 91/07087 | 5/1991 |
| WO | WO 92/16655 | 1/1992 |
| WO | WO 92/10092 | 6/1992 |
| WO | WO 92/10588 | 6/1992 |
| WO | WO 93/02992 | 2/1993 |
| WO | WO 93/09668 | 5/1993 |
| WO | WO 88/01302 | 6/1993 |
| WO | WO 93/11262 | 6/1993 |
| WO | WO 93/17126 | 9/1993 |
| WO | WO 93/22456 | 11/1993 |
| WO | WO 93/22480 | 11/1993 |
| WO | WO 95/00530 | 1/1995 |
| WO | WO 95/11995 | 5/1995 |
| WO | WO 95/33846 | 12/1995 |
| WO | WO 96/23078 | 8/1996 |
| WO | WO 97/10365 | 3/1997 |
| WO | WO 97/17317 | 5/1997 |
| WO | WO 97/19410 | 5/1997 |
| WO | Wo 97/27317 | 7/1997 |
| WO | Wo 97/29212 | 8/1997 |
| WO | WO 98/31836 | 7/1998 |
| WO | WO 99/60007 | 11/1999 |

OTHER PUBLICATIONS

Ajayaghosh et al., "Polymer–supported Solid–phase Synthesis of C–Terminal Peptide N–Methylamides Using a Modified Photoremovable 3–Nitro–4–methylaminomethylpolystyrene Support," *Ind. J.Chem.*,27B:1004–1008 (1988).

Ajayaghosh et al., "Polymer–Supported Synthesis of Protected Peptide Segments on a Photosensitive o–Nitro($\alpha$–Methyl)Bromobenzyl Resin," *Tetrahedron*, 44(21):6661–6666 (1988).

Arnold et al., "A Novel Universal Support for DNA & RNA Synthesis," abstract from *Federation Proceedings*, 43(7): abstract No. 3669 (1984).

Atherton et al., Solid Phase Peptide Synthesis: A Practical Approach, IRL Press, (1989), tbl. of cont., pp. vii–ix.

Augenlicht et al., "Cloning and Screening of Sequences Expressed in a Mouse Colon Tumor," *Cancer Research*, 42:1088–1093 (1982).

Augenlicht et al., "Expression of Cloned Sequences in Biopsies of Human Colonic Tissue and in Colonic Carcinoma Cells Induced to Differentiate in Vitro," *Cancer Res.*, 47:6017–6021 (1987).

Bains, W., "Hybridization Methods for DNA Sequencing," *Genomics*, 11(2):294–301 (1991).

Bains et al., "A Novel Method for Nucleic Acid Sequence Determination," *J.Theor.Biol.*, 135:303–307 (1988).

Bains, W., "Alternative Routes Through the Genome," *Biotechnology*, 8:1251–1256 (1988).

Balachander et al., "Functionalized Siloxy–Anchored Monolayers with Exposed Amino, Azido, Bromo, or Cyano Groups," *Tetrahed. Ltrs.*, 29(44):5593–5594 (1988).

Baldwin et al., "New Photolabile Phosphate Protecting Groups," *Tetrahed.*, 46(19):6879–6884 (1990).

Barltrop et al., "Photosensitive Protective Groups," *Chemical Communications*, pp. 822–823 (1966).

Barinaga, M., "Will 'DNA Chip' Speed Genome Initiative," *Science*, 253:1489 (1985).

Bart et al., "Microfabricated Electrohydrodynamic Pumps," *Sensors and Actuators*, A21–A23:193–197 (1990).

Bartsh et al., "Cloning of mRNA sequences from the human colon: Preliminary characterisation of defined mRNAs in normal and neoplastic tissues," *Br.J.Can.*, 54:791–798 (1986).

Baum, R., "Fledgling firm targets drug discovery process," *Chem. Eng. News*, p. 10–11 (1990).

Beltz et al., "Isolation of Multigene Families and Determination of Homologies by Filter Hybridization Methods," *Methods in Enzymology*, 100:266–285 (1983).

Benschop, Chem. Abstracts 114(26):256643 (1991).

Bhatia et al., "New Approach To Producing Patterned Biomolecular Assemblies," *J. American Chemical Society*, 114:4432–4433 (1992).

Biorad Chromatography Electrophoresis Immunochemistry Molecular Biology HPLC catalog M 1987 pp. 182.

Blawas et al., "Step–and–Repeat Photopatterning of Protein Features Using Caged–Biotin–BSA: Characterization and Resolution," *Langmuir*,14(15):4243–4250 (1998).

Blawas, A.S., "Photopatterning of Protein Features using Caged–biotin–Bovine Serum Albumin," dissertation for Ph.D. at Duke University in 1998.

Bos et al., "Amino–acid substirutions at codon 13 of the N–ras oncogene in human acute myeloid leukaemia," *Nature*, 315:726–730 (1985).

Boyle et al., "Differential distribution of long and short interspersed element sequences in the mouse genome: Chromosome karyotyping by fluorescence in situ hybridization," *PNAS*, 87:7757–7761 (1990).

Brock et al., "Rapid fluorescence detection of in situ hybridization with biotinylated bovine herpesvirus–1 DNA probes," J.Veterinary Diagnostic Invest., 1:34–38 (1989).

Burgi et al., "Optimization in Sample Stacking for High–Performance Capillary Electrophoresis," *Anal. Chem.*, 63:2024–2047 (1991).

Cameron et al., "Photogeneration of Organic Bases from o–Nitrobenzyl–Derived Carbamates," *J. Am. Chem. Soc.*, 113:4303–4313 (1991).

Carrano et al., "A High–Resolution, Fluorescence–Based, Semiautomated Method for DNA Fingerprinting," *Genomics*, 4:129–136 (1989).

Caruthers, M.H., "Gene Synthesis Machines: DNA Chemistry and Its Uses," *Science*, 230:281–285 (1985).

Chatterjee et al., "Inducible Alkylation of DNA Using an Oligonucleotide–Quinone Conjugate," *Am. J. Chem. Soc.*, 112:6397–6399 (1990).

Chee et al., "Accessing Genetic Information with High–Density DNA Arrays," *Science*, 274:610–614 (1996).

Chehab et al., "Detection of sicle cell anaemia mutation by colour DNA amplification," *Lancet*, 335:15–17 (1990).

Chehab et al. "Detection of specific DNA sequences by fluorescence amplification: A color complementation assay," *PNAS*, 86:9178–9182 (1989).

Clevite Corp., Piezoelectric Technology, Data for Engineers.

Corbett et al., "Reaction of Nitroso Aromatics with Glyoxylic Acid. A New Path to Hydroxamic Acids," *J. Org. Chem.*, 45:2834–2839 (1980).

Craig et al., "Ordering of cosmid clones covering the Herpes simplex virus type 1 (HSV–1) genome: a test case for fingerprinting by hybridization," *Nuc. Acid. Res.*, 18(9):2653–2660 (1990).

Cummings et al., "Photoactivable Fluorophores. 1. Synthesis and Photoactivation of o–Nitrobenzyl–Quenched Fluorescent Carbamates," *Tetrahedron Letters*, 29(1):65–68 (1988).

Diggelmann, "Investigating the VLSIPS synthesis process," Sep. 9,1994.

Di Mauro et al., "DNA Technology in Chip Construction," *Adv. Mater.*,5(5):384–386 (1993).

Drmanac et al., "Partial Sequencing by Oligo–Hybridization Concept and Applications in Genome Analysis," 1st Int. Conf. Electrophor., Supercomp., Hum. Genome pp. 60–74 (1990).

Drmanac et al., "Sequencing by Oligonucleotide Hybridization: A Promising Framework in Decoding of the Genome Program?", 1st Int. Conf. Electrophor., Supercomp., Hum. Genome pp. 47–59 (1990).

Drmanac et al., "Laboratory Methods, Reliable Hybridization of Oligonucleotides as Short as Six Nucleotides," *DNA and Cell Biol.*, 9(7):527–534 (1990).

Drmanac et al., "Sequencing of Megabase Plus DNA by Hybridization: theory of the Method," *Genomics*,4:114–128 (1989).

Dramanac et al., "Sequencing of Megabase Plus DNA by Hybridization: Theory of the Method," abstract of presentation given at Cold Spring Harbor Symposium on Genome Mapping and Sequencing, Apr. 27, 1988 thru May 1, 1988.

Dulcey et al., "Deep UV Photochemistry of Chemisorbed Monolayers: Patterned Coplanar Molecular Assemblies," *Science*, 252:551–554 (1991).

Duncan et al., "Affinity Chromatography of a Sequence–Specific DNA Binding Protein Using Teflon–Linked Oligonucleotides," Analytical Biochemistry, 169:104–108 (1988).

Effenhauser et al., "Glass Chips for High–speed Capillary Electrophoresis Separations with Submicrometer Plate Heights," Anal. Chem., 65:2637–2642 (1993).

Effenhauser et al., "High–Speed Separation of Antisense Oligonucleotides on a Micromachined Capillary Electrophoresis Device," *Anal. Chem.*, 66:2949–2953 (1994).

Ekins et al., "High Specific Activity Chemiluminescent and Fluorescent Markers: their Potential Application to High Sensitivity and 'Multi–analyte' Immunoassays," *J. Bioluminescence Chemiluminescence,* 4:59–78 (1989).

Ekins et al., "Development of Microspot Multi–Analyte Ratiometric Immunoassay Using dual Fluorescent–Labelled Antibodies," *Anal. Chemica Acta*, 227:73–96 (1989).

Ekins et al., "Multianalyte Microspot Immunoassay–Microanalytical 'Compact Disk' of the Future," *Clin. Chem.*, 37(11):1955–1967 (1991).

Ekins, R.P., "Multi–Analyte immunoassay*," *J. Pharmaceut. Biomedical Analysis*, 7(2):155–168 (1989).

Ekins et al., "Fluorescence Spectroscopy and its Application to a New Generation of High Sensitivity, Multi–Microspot, Multianlyte, Immunoassay," *Clin. Chim. Acta*, 194:91–114 (1990).

Evans et al., "Microfabrication for Automation of Molecular processes in Human Genome Analysis," *Clin. Chem.*, 41(11):1681 (1995).

Evans et al., "Physical mapping of complex genomes by cosmid multiplex anlaysis," *PNAS*, 86:5030–5034 (1989).

Ezaki et al., "Small–Scale DNA Preparation for Rapid Genetic Identification of *Campylobacter* Species without Radioisotope," *Microbiol. Immunology*,32(2):141–150 (1988).

Fan et al., "Mapping small DNA sequences by fluorescence in situ hybridization directly on banded metalplast chromosomes," PNAS, 87(16):6223–6227 (1990).

Fan et al., "Micromachining of Capillary Electrophoresis Injectors and Separators on Glass Chips and Evaluation of Flow at Capillary Intersections," Anal. Chem., 66:177–184 (1994).

Fettinger et al., "Stacked modules for micro flow systems in chemical analysis: concept and studies using an enlarged model," *Sensors and Actuators*, B17:19–25 (1993).

Flanders et al., "A new interferometric alignment technique," *App. Phys. Ltrs.*,31(7):426–429 (1977).

Fodor et al., "Multiplexed biochemical assays with biological chips," *Nature*, 364:555–556 (1993).

Fodor et al., "Light–directed, Spatially Addressable Parallel Chemical Synthesis," *Science*, 251:767–773 (1991).

Forman et al., "Thermodynamics of Duplex Formation and Mismatch Discrimination on Photolithography Synthesized Oligonucleotide Arrays," chapter 13pp. 206–228 from *Molecular Modeling of Nucleic Acids*, ACS Symposium Series 682, Apr. 13–17, 1997, Leontis et al., eds.

Frank et al., "Simultaneous Multiple Peptide Synthesis Under Continuous flow Conditions on Cellulose Paper Discs as Segmental Solid Supports," *Tetrahedron*, 44(19):6031–6040 (1988).

Frank et al., "Automation of DNA Sequencing Reactions and Related Techniques: A Workstation for Micromanipulation of Liquids," *Bio/Technology*,6:1211–1212 (1988).

Frank et al., "Simultaneous Synthesis and Biological Applications of DNA Fragments: An Efficient and Complete Methodology," *Methods in Enzymology*, 154:221–250 (1987).

Fuhr et al., "Travelling wave–driven microfabricated electrohydrodynamic pumps for liquids," *J. Micromech. Microeng.*, 4:217–226 (1994).

Fuller et al., "Urethane–Protected Amino Acid N–Carboxy Anhydrides and Their Use in Peptide Synthesis," *J. Amer. Chem. Soc.*, 112(20):7414–7416 (1990).

Furka et al., "General method for rapid synthesis of multicomponent peptide mixtures," *Int. J. Peptide Protein Res.*, 37:487–493 (1991).

Furka et al., "Cornucopia of Peptides by Synthesis," 14th Int.Congress of Biochem. abst.#FR:013, Jul. 10–15, 1988 Prague, Czechoslavakia.

Furka et al., "More Peptides by Less Labour," abst. 288, Int. Symp. Med. Chem., Budapest Hungary Aug. 15–19, 1988.

Gait, eds., pp. 1–115 from *Oligonucleotide Synthesis: A Practical Approach*, IRL Press, (1984).

Gazard et al., "Lithographic Technique Using Radiation–Induced Grafting of Arcylic Acid into Poly(Methyl Methacrylate)Films," *Polymer Engineering and Science*, 20(16):1069–1072 (1980).

Gergen et al., "Filter replicas and permanent collections of recombinant DNA plasmids," *Nuc.Acids Res.*, 7(8):2115–2137 (1979).

Getzoff et al., "Mechanisms of Antibody Binding to a Protein," *Science*, 235:1191–1196 (1987).

Geysen et al., "Strategies for epitope analysis using peptide synthesis," *J. Immunol. Meth.*, 102:259–274 (1987).

Geysen et al., "Use of peptide synthesis to probe viral antigens for epitopes to a resolution of a single amino acid," *PNAS*, 81:3998–4002 (1984).

Geysen et al., "A synthetic strategy for epitope mapping," from Peptide:Chem. & Biol., Proc. of 10th Am. Peptides Symp., May 23–28, 1987, pp. 519–523, (1987).

Geysen, "Antigen–antibody interactions at the molecular level: adventures in peptide synthesis," *Immunol. Today*, 6(12):364–369 (1985).

Geysen et al., "Cognitive Features of Continuous Antigenic Determinants," from Synthetic Peptides: Approaches to Biological Probes, pp. 19–30, (1989).

Geysen et al., "Chemistry of Antibody Binding to a Protein," *Science*, 235:1184–1190 (1987).

Geysen et al., "The delineation of peptides able to mimic assembled epitopes," 1986 CIBA Symp., pp. 130–149.

Geysen et al., "Cognitive Features of Continuous Antigenic Determinants," *Mol. Recognit.*, 1(1):1–10 (1988).

Geysen et al., "A Prio Ri Delineation of a Peptide Which Mimics A Discontinuous Antigenic Determinant," *Mol. Immunol.*, 23(7):709–715 (1986).

Gilon et al., "Backbone Cyclization: A New Method for Conferring Conformational Constraint on Peptides," *Biopolymers*, 31(6):745–750 (1991).

Gingeras et al., "Hybridization properties of immobilized nucleic acids," *Nuc. Acids Res.*, 15(13):5373–5390 (87).

Gummerlock et al., "RAS Enzyme–Linked Immunoblot Asssay Discriminates p21 Species: A Technique to Dissect Gene Family Expression," *Anal. Biochem.*, 180:158–169 (1989).

Gurney et al., "Activation of a potassium current by rapid photochemically generated step increases of intracellular calcium in rat sympathetic neurons," *PNAS*, 84:3496–3500 (1987).

Haase et al., "Detection of Two Viral Genomes in Single Cells by Double–Label Hybridization in Situ and Color Microradioautography," *Science*, 227:189–192 (1985).

Hacia, et al., "Two color hybridization analysis using high density oligonucleotide arrays and energy transfer dyes," *Nuc. Acids Res.*, 26(16):3865–3866 (1998).

Hack, M.L., "Conics Formed to Make Fluid & Industrial Gas Micromachines," *Genetic Engineering News*, 15(18):1, 29 (1995).

Hagedorn et al., "Pumping of Water Solutions in Microfabricated Electrohydrodynamic Systems," from Micro Electro Mechanical Systems conference in Travemunde Germany (1992).

Hames et al., *Nuclear acid hybridization, a practical approach*, cover page and table of contents (1985).

Hanahan et al., "Plasmid Screening at High Colony Density," *Meth. Enzymology*, 100:333–342 (1983).

Hanahan et al., "Plasmid screening at high colony destiny," *Gene*, 10:63–67 (1980).

Haridasan et al., "Peptide Synthesis using Photolytically Cleavable 2–Nitrobenzyloxycarbonyl Protecting Group," *Proc. Indian Natn. Sci. Adad.*, 53A(6):717–728 (1987).

Harrison et al., "Capillary Electrophoresis and Sample Injection Systems Integrated on a Planar Glass Chip," *Anal. Chem.*, 64:1926–1932 (1992).

Harrison et al., "Micromachining a Minaturized Capillary Electrophoresis–Based Chemical Analysis System on a Chip," Science, 261:895–897 (1993).

Harrison et al., "Towards minaturized electrophoresis and chemical analysis systems on silicon: an alternative to chemical sensors*," *Sensors and Actuators*, B10:107–116 (1993).

Harrison et al., "Rapid separation of fluorescein derivatives using a micromachined capillary electrophoresis system," *Analytica Chemica Acta*, 283:361–366 (1993).

Hellberg et al., "Minimum analogue peptide sets (MAPS) for quantitative structure–activity relationships," *Int. J. Peptide Protein Res.*, 37:414–424 (1991).

Hilser et al., "Protein and peptide mobility in capillary zone electrophoresis, A comparison of existing models and further analysis," *J. Chromatography*, 630:329–336 (1993).

Ho et al., "Highly Stable Biosensor Using an Artificial Enzyme," *Anal. Chem.*, 59:536–537 (1987).

Hochgeschwender et al., "Preferential expression of a defined T–cell receptor β–chain gene in hapten–specific cytotoxic T–cell clones," *Nature*, 322:376–378 (1986).

Hodgson, J., "Asssays A La Photolithography," *Biotech.*, 9:419 (1991).

Hopman et al., "Bi–color detection of two target DNAs by non–radioactive in situ hybridization*," *Histochem.*, 85:1–4 (1986).

Iwamura et al., "1–Pyrenylmethyl Esters, Photolabile Protecting Groups for Carboxlic Acids," *Tetrahedron Ltrs.*, 28(6):679–682 (1987).

Iwamura et al., "1–(α–Diazobenzyl)pyrene: A Reagent for Photolabile and Fluorescent Protection of Carboxyl Groups of Amino Acids and Peptides," *Synlett*, p. 35–36 (1991).

Jacobson et al., "Effects of Injection Schemes and Column Geometry on the Performance of Microchip Electrophoresis Devices," Anal. Chem., 66:1107–1113 (1994).

Jacobsen et al., "Open Channel Electrochromatography on a Microchip," Anal. chem., 66:2369–2373 (1994).

Jacobson et al., "Microchip Capillary Electrophoresis with an Integrated Postcolumn Reactor" Anal. Chem., 66:3472–3476 (1994).

Jacobson et al., "Precolumn Reactions with Electrophoretic Analysis Integrated on a Microchip," *Anal. Chem.*, 66:4127–4132 (1994).

Jacobson et al., "Microfabricated chemical measurement systems," *Nature Medicine*, 1(10):1093–1096 (1995).

Jacobsen et al., "Fused Quartz Substrates for Microchip Electrophoresis," *Anal. chem.*, 67:2059–2063 (1995).

Jacobson et al., "High–Speed Separtions on a Microchip," Anal. Chem., 66:1114–1118 (1994).

Jacobson et al., "Microchip electrophoresis with sample stacking," *Electrophoresis*, 16:481–486 (1995).

Jayakumari, "Peptide synthesis in a triphasic medium catalysed by papain immobilized on a crosslinked polystyrene support," *Indian J. Chemistry*, 29B:514–517 (1990).

Kaiser et al., "Peptide and Protein Synthesis by Segment Synthesis–Condensation," *Science*, 243:187–192 (1989).

Kaplan et al., "Photolabile chelators for the rapid photorelease of divalent cations," *PNAS*, 85:6571–6575 (1988).

Karube, "Micro–biosensors based on siicon fabrication technology," chapter 25 from Biosensors:Fundamentals and Applications, Turner et al., eds., Oxford Publ., 1987, pp. 471–480 (1987).

Kates et al., "A Novel, Convenient, Three–dimensional Orthogonal Strategy for Solid–Phase Synthesis of Cyclic Peptides 1–3," *Tetrahed. Letters*, 34(10):1549–1552 (1993).

Kerkof et al., "A Procedure for Making Simultaneous Determinations of the Relative Levels of Gene Transcripts in Tissues or Cells," *Anal. Biochem.*, 188:349–355 (1990).

Khrapko et al., "An Oligonucleotide hybridization approach to DNA sequencing," *FEBS Lett.*, 256(1,2):118–122 (1989).

Kievits et al., "Rapid subchromosomal localization of cosmids by nonradioactive in situ hybridization," *Cytogenetics Cell Genetics*, 53(2–3):134–136 (1990).

Kimura et al., "An Immobilized Enzyme Membrane Fabrication Method using an Ink Jet Nozzle," *Biosensors*, 4:41–52 (1988).

Kimura et al., "An Integrated SOS/FET Multi–Biosensor," *Sensors & Actuators*, 9:373–387 (1986).

Kitazawa et al., "In situ DNA–RNA hybridization using in vivo bromodeoxyuridine–labeled DNA probe," *Histochemistry*, 92:195–199 (1989).

Kleinfeld et al., "Controlled Outgrowth of Dissociated Neurons on Patterned Substrates," *J. Neurosci.*, 8(11):4098–4120 (1988).

Knight, P., "Materials and Methods/Microsequencers for Proteins and Oligosaccharides," *Bio/Tech.*, 7:1075–76 (1989).

Kohara et al., "The Physical Map of the Whole *E. coli* Chromosome: Application of a New Strategy for Rapid Analysis and Sorting of a Large Genomic Library," *Cell*, 50:495–508 (1987).

Krile et al., "Multiplex holography with chirp–modulated binary phase–coded reference–beam masks," *Applied Opt.*, 18(1):52–56 (1979).

Labat, I., "Subfragments as an informative characteristic of the DNA molecule—computer simulation," research report submitted to the University of Belgrade College of Natural Sciences and Mathematics, (1988).

Lainer et al., "Human Lymphocyte Subpopulations Identified by Using Three–Color Immunofluorescence and Flow Cytometry Analysis: Correlation of Leu–2, Leu–3, Leu–7, Leu–8, and Leu–11 Clee Surface Antigen Expression," *Journal of Immunology*, 132(1):151–156 (1984).

Lam et al., "A new type of synthetic peptide library for identifying ligand–binding activity," *Nature*, 354:82–84 (1991).

Laskey et al., "Messenger RNA prevalence in sea urchin embryos measured with cloned cDNAs," *PNAS*, 77(9):5317–5321 (1980).

Lee et al., "synthesis of a Polymer Surface Containing Covalently Attached Triethoxysilane Functionality: Adhesion to Glass," *Macromolecules*, 21:3353–3356 (1988).

Lehrach et al., "Labelling oligonucleotides to high specific activity (1)," *Nuc. Acids Res.*, 17(12):4605–4610 (89).

Lehrach et al., "Phage Vectors—EMBL Series," *Meth. Enzymology*, 153:103–115 (1987).

Levy, M.F., "Preparing Additive Printed Circuits," *IBM Tech. Discl. Bull.*, 9(11):1473 (1967).

Lichter et al., "High–Resolution Mapping of Human Chromosome 11 by in Situ hybridization with Cosmid Clones," *Science*, 247:64–69 (1990).

Licther et al., "Fluorescence in situ hybridization with Alu and L1 polymerase chain reaction probes for rapid characterization of human chromosomes in hybrid cell lines," *PNAS*, 87:6634–6638 (1990).

Lichter et al., "Rapid detection of human chromosome 21 abberations by in situ hybridization," *PNAS*, 85:9664–9668 (1988).

Lichter et al., "Is non–isotopic in situ hybridization finally coming of age," *Nature*, 345:93–94 (1990).

Lieberman et al. "A Light source Smaller Than the Optical Wavelength," *Science*, 247:59–61 (1990).

Lipshutz et al., "Using Oligonucleotide Probe Arrays To Access Genetic Diversity," *BioTech.*, 19(3):442–7 (1995).

Liu et al., "Sequential Injection Analysis in Capillary Format with an Electroosmotic Pump," *Talanta*, 41(11):1903–1910 (1994).

Lockhart et al. "Expression monitoring by hybridization to high–density oligonucleotide arrays," *Nat. Biotech.*, 14:1675–1680 (1996).

Logue et al., "General Approaches to Mask Design for Binary Optics," SPIE, 1052:19–24 (1989).

Loken et al., "three–color Immunofluorescence Analysis of Leu Antigens on Human Peripheral Blood Using Two Lasers on a Fluorescence–Activated Cell Sorter," *Cymoetry*, 5:151–158 (1984).

Love et al., "Screening of λ Library for Differentially Expressed Genes Using in Vitro Transcripts," *Anal. Biochem.*, 150:429–441 (1985).

Lowe, C.R., "Biosensors," *Trends in Biotech.*, 2:59–65 (1984).

Lowe, C.R., "An Introduction to the Concepts and Technology of Biosensors," *Biosensors*, 1:3–16 (1985).

Lowe, C. R., Biotechnology and Crop Improvement and Protection, BCPC Publications, pp. 131–138 (1986).

Lowe et al., "Solid–Phase Optoelectronic Biosensors," *Methods in Enzymology*, 137:338–347 (1988).

Lowe, C.R., "Biosensors," *Phil. Tran. R. Soc. Lond.*, 324:487–496 (1989).

Lu et al., "Differential screening of murine ascites cDNA libraries by means of in vitro transcripts of cell–cycle–phase–specific cDNA and digital image processing," *Gene*, 86:185–192 (1990).

Lysov et al., "A new method for determining the DNA nucleotide sequence by hybridization with oligonucleotides," *Doklady Biochem.*303(1–6):436–438 (1989).

Lysov et al., "DNA Sequencing by Oligonucleotide Hybridization," First International Conference on Electrophoresis, Supercomputing and the Human Genome, Apr. 10–13, 1990 p. 157.

MacDonald et al., "A Rapid ELISA for Measuring Insulin in a Large Number of Research Samples," *Metabolism*, 38(5):450–452 (1989).

Mairanovsky, V.G., "Electro–Deprotection—Electrochemical Removal of Protecting Groups**," *Agnew. Chem. Int. Ed. Engl.*, 15(5):281–292 (1976).

Manz et al., "Miniaturized Total Chemical Analysis Systems: a Novel Concept for Chemical Sensing," *Sensors and Actuators*, B1:244–248 (1990).

Manz et al., "Micromachining of monocrystalline silicon and glass for chemical analysis systems, A look into next century's technology or just a fashionable craze?," *Trends in Analytical Chem.*, 10(5):144–149 (1991).

Manz et al., "Planar chips technology for minaturization and integration of separation techniques into monitoring systems, Capillary electrophoresis on a chip," *J. Chromatography*, 593:253–258 (1992).

Manz et al., "Planar Chips Technology for Miniaturization of Separation Systems: A Developing Perspective in Chemical Monitoring," chapter 1, 1–64 (1993).

Manz et al., "Electroosmotic pumping and electrophoretic separations for miniaturized chemical analysis systems," *J. Micromech. Microeng.*, 4:257–265 (1994).

Masiakowski et al., "Cloning of cDNA sequences of hormone–regulated genes from the MCF–7 human breast cancer cell line," *Nuc. Acids Res.*, 10(24):7895–7903 (1982).

Matsumoto et al., "Preliminary Investigation of Micropumping Based on Electrical Control of Interfacial Tension," *IEEE*, pp. 105–110 (1990).

Matsuzawa et al., "Containment and growth of neuroblastoma cells on chemically patterned substrates," *J. Neurosci. Meth.*, 50:253–260 (1993).

McCray et al., "Properties and Uses of Photoreactive Caged Compounds," *Ann. Rev. Biophys. Chem.*, 18:239–270 (1989).

McGall et al. "The Efficiency of Light–Directed Synthesis of DNA Arrays on Glass Substrates," *J. American Chem. Soc.*, 119(22):5081–5090 (1997).

McGillis, VLSI Technology, Sze, eds., Chapter 7, "Lithography," pp. 267–301 (1983).

McMurray, J.S., "Solid Phase Synthesis of a Cyclic Peptide Using Fmoc Chemistry," *Tetrahedron Letters*, 32(52):7679–7682 (1991).

Meinkoth et al., "Review: Hybridization of Nucleic Acids Immobilized on solid Supports," *Analytical Biochem.*, 138:267–284 (1984).

Melcher et al., "Traveling–Wave Bulk Electroconvection Induced across a Temperature Gradient," *Physics of Fluids*, 10(6):1178–1185 (1967).

Merrifield, R.B., "Solid Phase peptide Synthesis. I. The Synthesis of a Tetrapeptide," *J.Am.Chem.Soc.*, 85:2149–2154 (1963).

Michiels et al., "Molecular approaches to genome analysis: a strategy for the construction of ordered overlapping clone libraries," *CABIOS*, 3(3):203–10 (1987).

Mirzabekov, A.D., "DNA sequencing by hybridization—a megasequencing method and a diagnostic tool?," *TIBTECH*, 12:27–32 (1994).

Monaco et al., "Human Genome Linking with Cosmids and Yeast Artificial Chromosomes", abstract from CSHS, p. 50, (1989).

Morita et al., "Direct pattern fabrication on silicone resin by vapor phase electron beam polymerization," *J.Vac.Sci.Technol.*, B1(4):1171–1173 (1983).

Morrison et al., "Solution–Phase Detection of Polynucleotides Using Interacting Fluorescent Labels and Competitive Hybridization," *Anal. Biochem.*, 183:231–244 (1989).

Munegumi et al., "thermal Synthesis of Polypeptides from N–Boc–Amino Acid (Aspartic Acid, β–Aminoglutaric Acid) Anhydrides," *Chem. Letters*, pp. 1643–1646 (1988).

Mutter et al., "Impact of Conformation on the Synthetic Strategies for Peptide Sequences," pp. 217–228 from Chemistry of Peptides and Proteins, vol. 1, Proceedings of the Third USSR–FRG Symp., in USSR (1982).

Nakamori et al., "A Simple and Useful Method for Simultaneous Screening of Elevated Levels of Expression of a Variety of Oncogenes in Malignant Cells," *Jpn. J. Cancer Res.*, 79:1311–1317 (1988).

Nederlof et al., "Multiple Fluorescence In Situ Hybridization," *Cytometry*, 11:126–131 (1990).

Nyborg, W., "Acoustic Streaming," chapter 11 pp. 265–329 from Physical Acoustics, Principles and Methods, Mason, eds., vol. II, part B, Academic Press, New York and London (1965).

Ocvirk et al., "High Performance Liquid Chromatography Partially Integrated onto a Silicon Chip," *Analyt. Meth. Instrumentation*, 2(2):74–82 (1995).

Ohtsuka et al., "Studies on transfer ribonucleic acids and related compounds. IX Ribonucleic oligonucleotide synthesis using a photosensitive 0–nitrobenzyl protection at the 2'–hydroxl group," *Nuc.Acids.Res.*, 1(10):1351–1357 (1974).

Olefirowicz et al., "Capillary Electrophoresis for Sampling Single Nerve Cells," *Chimia*, 45(4):106–108 (1991).

Patchornik et al., "Photosensitive Protecting Groups," *J.Am. Chem.Soc.*, 92(21):6333–6335 (1970).

Patent Abstracts of Japan from EPO, Abst. 13:557, JP 1–233 447 (1989).

Pease et al., "Light-generated oligonucleotide arrays for rapid DNA sequence analysis," *PNAS*, 91:5022–26 (1994).

Pevzner, P.A., "1–Tuple DNA Sequencing: Computer Analysis," *J. Biomol. Struct. Dynam*, 7(1):63–69 (1989).

Pfahler et al., "Liquid Transport in Micron and Submicron Channels," *Sensors and Actuators*, A21–A23:431–4 (90).

Pidgeon et al., "Immobilized Artificial Membrane Chromatography: Supports Composed of Membrane Lipids," *Anal. Biochem.*, 176:36–47 (89).

Pillai, V.N., "Photoremovable Protecting Groups in Organic Synthesis," *Synthesis*, pp. 1–26 (1980).

Pillai et al., "3–Nitro–4–Aminomethylbenzoylderivate von Polyethylenglykolen: Eine neue Klasse von Photosensitive loslichen Polymeren Tragern zur Synthese von C–terminalen Peptidamiden," *Tetrah. ltr.*, # 36 p. 3409–3412 (1979).

Pillai et al., "Synthetic Hydrophilic Polymers, Biomedical and Chemical Applications," *Naturwissenschaften*, 68:558–566 (1981).

Pirrung et al., "Proofing of Photolithographic DNA Synthesis with 3'.5'–Dimethoxybenzoinyloxycarbonyl–Protected Deoxynucleoside Phosphoramidites," *J. Org. Chem.*, 63(2):241–246 (1998).

Pirrung et al., "Comparison of Methods for Photochemical Phosphoramidite–Based DNA Synthesis," *J. Org. Chem.*, 60:6270–6276 (1995).

Ploax et al., "Cyclization of peptides on a solid support," *Int. J. Peptide Protein Research*, 29:162–169 (1987).

Polsky–Cynkin et al., "Use of DNA Immobilized on Plastic and Agarose Supports to Detect DNA by Sandwich Hybridization," *Clin. Chem.*, 31(9):1428–1443 (1985).

Poustka et al., "Molecular Approaches to Mammalian Genetics," Cold Spring Harbor Symposia on Quantitive Biology, 51:131–139 (1986).

Purushothaman et al., "Synthesis of 4,5–diarylimidazoline–2–thiones and their photoconversion to bis(4,5–diarylimidazol–2–yl) sulphides," *Ind. J. Chem.*, 29B:18–21 (1990).

Quesada et al., "High–Sensitivity DNA Detection with a Laser–Exited Confocal Fluorscence Gel Scanner," *Biotechniques*, 10:616 (1991).

Reichmanis et al., *J. Polymer Sci. Polymer Chem. Edition*, 23:1–8 (1985).

Richter et al., "An Electrohydrodynamic Micropump," *IEEE*, pp. 99–104 (1990).

Richter et al., "Electrohydrodynamic Pumping and Flow Measurement," *IEEE*, pp. 271–276 (1991).

Richter et al., "A Micromachined electrohydrodynamic (EHD) pump," *Sensors and Actuators*, A29:159–168 (91).

Robertson et al., "A General and Efficient Route for Chemical Aminoacylation of Transfer RNAs," *J. Am. Chem. Soc.*, 113:2722–2729 (1991).

Rodda et al., "The Antibody Response to Myoglobin–1. Systematic Synthesis of Myglobin Peptides Reveals Location and Substructure of Species–Dependent Continuous Antigenic Determinants," *Mol. Immunol.*, 23(6):603–610 (1986).

Rodgers, R.P., "Data Processing of Immunoassay Results," Manual of Clin. Lab. Immunol., 3rd ed., ch. 15, pp. 82–87 (1986).

Rose, D.J., "Free–solution reactor for post–column fluorescence detection in capillary zone electrophoresis," *J. Chromatography*, 540:343–353 (1991).

Rovero et al., "Synthesis of Cylic Peptides on solid Support," *Tetrahed. Letters*, 32(23):2639–2642 (1991).

Sambrook, Molecular Cloning—A Laboratory Manual, publ. in 1989 (not included).

Saiki et al., "Genetic analysis of amplified DNA with immobilized sequence–specific oligonucleotide probes," *PNAS*, 86:6230–6234 (1989).

Saiki et al., "Analysis of enzymatically amplified β–globin and HLA–DQα DNA with Allele–specific oligonucleotide probes," *Nature*, 324:163–166 (1986).

Scharf et al., "HLA class II allelic variation and susceptibility to pemphigus vulgaris,"*PNAS*, 85(10):3504–3508 (1988).

Schuup et al., "Mechanistic Studies of the Photorearrangement of o–Nitrobenzyl Esters," *J. Photochem.*, 36:85–97 (1987).

Seiler et al., "Planar Glass Chips for Capillary Electrophoresis: Repetitive Sample Injection, Quantitation, and Separation Efficency," *Anal. Chem.*, 65:1481–1488 (1993).

Seller et al., "Electroosmotic Pumping and Valveless Control of Fluid Flow within a Manifold of Capillaries on a Glass Chip," Anal. Chem., 66:3485–3491 (1994).

Semmelhack et al., "Selective Removal of Protecting Groups Using Controlled Potential Electrolysis," *J. Am. Chem. Society*, 94(14):5139–5140 (1972).

Sheldon et al., "Matrix DNA Hybridization," *Clinical Chemistry*, 39(4):718–719 (1993).

Shin et al., "Dehydrooligonpeptides. XI. Facile Synthesis of Various Kinds of Dehydrodi– and tripeptides, and Dehydroenkephalins Containing Tyr Residue by Using N–Carboxydehydrotyrosine Anhydride," *Bull. Chem. Soc. Jpn.*, 62:1127–1135 (1989).

Sim et al., "Use of a cDNA Library for Studies on Evolution and Developmental Expression of the Chorion Multigene Families," *Cell*, 18:1303–1316 (1979).

Smith et al., "A Novel Method for Delineating Antigenic Determinants: Peptide Synthesis and Radioimmunoassay Using the Same Solid Support," *Immunochemistry*, 14:565–568 (1977).

Southern et al., "Report on the Sequencing by Hybridization Workshop," *Genomics*, 13:1378–1383 (1992).

Southern et al., "Oligonucleotide hybridisations on glass supports: a novel linker for oligonucleotide synthesis and hybridization properties of oligonucleotides synthesized in situ," *Nuc. Acids Res.*, 20(7):1679–1584 (1992).

Southern et al., "Analyzing and Comparing Nucleic Acid Sequences by Hybridization to Arrays of Oligonucleotides: Evaluation Using Experimental Models," Genomics, 13:1008–10017 (1992).

Stemme et al., "A valveless diffuser/nozzle–based fluid pump," *Sensors and Acutators*, A39:159–167 (1993).

Stryer, L., "DNA Probes and Genes Can be Synthesized by Automated Solid–Phase Methods," from *Biochemistry*, Third Edition, published by W.H. Freeman & Co., (1988).

Stuber et al., "Synthesis and photolytic cleavage of bovine insulin B22–30 on a nitrobenzoylglycyl–poly (ethylene glycol) support," *Int. J. Peptide Protein Res.*, 22(3):277–283 (1984).

Sundberg et al., "Spatially–Addressable Immobilization of Macromolecules on Solid Supports," *J. Am. Chem. Soc.*, 117(49):12050–12057 (1995).

Swedberg, S.A., "Use of non–ionic and zwitterionic surfactants to enhance selectivity in high–performance capillary electrophoresis, An apparent micellar electrokinetic capillary chromatography mechanism," *J. Chromatography*, 503:449–452 (1990).

Titus et al., "Texas Red, a Hydrophilic, red–emitting fluorophore for use with fluorescein in dual parameter plow microfluorometric and fluorescence microscopic studies," *J. Immunol. Meth.*, 50:193–204 (1982).

Tkachuk et al., "Detection of bcr–abl Fusion in chronic Myelogeneous Leukemia by in situ Hybridization," *Science*, 250:559–562 (90).

Trzeciak et al., "Synthesis of 'Head–to–Tail' Cyclized Peptides on Solid Support by FMOC Chemistry," *Tetrahed. Letters*, 33(32):4557–4560 (1992).

Tsien et al., "Control of Cytoplasmic Calcium with Photolabile Tetracarboxylate 2–Nitrobenzyhydrol Chelators," *Biophys. J.*, 50:843–853 (1986).

Tsutsumi et al., "Expression of L– and M–Type Pyruvate Kinase in Human Tissues," *Genomics*, 2:86–89 (1988).

Turchinskii et al., "Multiple Hybridization in Genome Analysis, Reaction of Diamines and Bisulfate with Cytosine for Introduction of Nonradioactive labels Into DNA," *Molecular Biology*, 22:1229–1235 (1988).

Turner et al., "Photochemical Activation of Acylated α–Thrombin," *J. Am. Chem. Soc.*, 109:1274–1275 (1987).

Urdea et al., "A novel method for the rapid detection of specific nucleotide sequences in crude biological samples without blotting or radioactivity; application to the analysis of hepatitis B virus in human serum," *Gene*, 61:253–264 (1987).

Urdea et al., "A comparison of non–radioisotopic hybridization assay methods using fluorescent, chemiluminescent and enzyme labeled synthetic oligodeoxyribonucleotide probes," *Nuc. Acids Res.*, 16(11):4937–4956 (1988).

Van der Voort et al., "Design and Use of a Computer Controlled Confocal Microscope for Biological Applications," *Scanning*, 7(2):66–78 (1985).

Van Hijfte et al., "Intramolecular 1,3–Diyl Trapping Reactions. A Formal Total Synthesis of –Coriolin," J. Organic Chemistry, 50:3942–3944 (1985).

Veldkamp, W.B., "Binary optics: the optics technology of the 1990s," CLEO 90, vol. 7, paper #CMG6 (1990).

Verlaan–de Vries et al., "A dot–blot screening procedure for mutated ras oncogenes using synthetic oligodeoxynucleotides," *Gene*, 50:313–320 (1986).

Verpoorte et al., "Three–dimensional micro flow manifolds for miniaturized chemical analysis systems," *J. Micromech. Microeng.*, 4:246–256 (1994).

Volkmuth et al., "DNA electrophoresis in microlithographic arrays," *Nature*, 358:600–602 (1992).

Voss et al., "The immobilization of oligonucleotides and their hybridization properties," *Biochem. Soc. Transact.*, 16:216–217 (1988).

Walker et al., "Photolabile Protecting Groups for an Acetylcholine Receptor Ligand, Synthesis and Photochemistry of a New Class of o–Nitrobenzyl Derivatives and their Effects on Receptor Function," *Biochemistry*, 25:1799–1805 (1986).

Wallace et al., "Hybridization of synthetic oligodeoxyribonucleotides to $\Phi\chi$ 174 DNA: the effect of single base pair mismatch," *Nuc. Acids Res.*, 11(6):3543–3557 (1979).

Washizu et al., "Handling Biological Cells Using a Fluid Integrated Circuit," *IEEE Transactions Industry Applications*, 26(2):352–358 (1990).

Werner et al., "Size–Dependent Separation of Proteins Denatured in SDS by Capillary Electrophoresis Using a Replaceable Sieving Matrix," *Anal. Biochem.*, 212:253–258 (1993).

White et al., "An Evaluation of Confocal Versus Conventional Imaging of Biological Structures by Fluorescence Light Microscopy," *J. Cell. Biol.*, 105(1):41–48 (1987).

Widacki et al., "Biochemical Differences in Qa–2 Antigens Expressed by Qa–2+,6+ and Qa–2aα,6– Strains. Evidence for Differential Expression of the Q7 and Q9 Genes," *Mol. Immunology*, 27(6):559–570 (1990).

Wilcox et al., "Synthesis of Photolabile 'Precursors' of Amino Acid Neurotransmitters," *J. Org. Chem.*, 55:1585–1589 (1990).

Wilding et al., "PCR in a Silicon Microstructure," *Clin. Chem.*,40(9):1815–1818 (1994).

Wilding et al., "Manipulation and Flow of Biological Fluids in Straight Channels Micromachined in Silicon," *Clin. Chem.*, 40(1):43–47 (1994).

Wittman–Liebold, eds., Methods in Protein Sequence Analysis, from Proceedings of 7th Int'l Conf., Berlin, Germany, Jul. 3–8, 1988, table of contents, pp. xi–xx* (1989).

Woolley et al., "Ultra–high–speed DNA fragment separations using microfabricated capillary array electrophoresis chips," *PNAS*, 91:11348–11352 (1994).

Wu et al., "Synthesis and Properties of Adenosine–5'–triphosphoro–γ–5–(5–sulfonic acid)naphthyl Ethylamidate: A Fluorescent Nucleotide Substrate for DNA–Dependent RNA Polymerase from *Escherichia coli*," *Arch. Biochem. Biophys.*, 246(2):564–571 (1986).

Wu et al., "Laboratory Methods, Direct Analysis of Single Nucleotide Variation in Human DNA and RNA Using In Situ Dot Hybridization," *DNA*, 8(2):135–142 (1989).

Yamamoto et al., "Features and applications of the laser scanning microscope," *J. Mod. Optics*, 37(11):1691–1701 (1990).

Yarbrough et al., "Synthesis and Properties of Fluorescent Nucleotide Substrates for DNA–dependent RNA Polymerases," *J. Biol. Chem.*, 254(23):12069–12073 (1979).

Yosomiya et al., "Performance, Glass fiber Having Isocyanate Group on the Surface. Preparation and Reaction with Amino Acid," *Polymer Bulletin*, 12:41–48 (1984).

Young, W.S., "Simultaneous Use of Digoxigenin– and Radiolabeled Oligodeoxyribonucleotide Probes for Hybridization Histochemistry," *Neuropeptides*, 13:271–275 (1989).

Yue et al., "Miniature Field–Flow Fractionation System for Analysis of Blood Cells," *Clin. Chem.*, 40(9):1810–1814 (1994).

Zehavi et al., "Light–Sensitive Glycosides. I. 6–Nitroveratryl β–D–Glucopyranoside and 2–Nitrobenzyl β–D–Glucopyranoside," *J. Org. Chem.*, 37(14):2281–2285 (1972).

Zengerle et al., "Transient measurements on miniaturized diaphragm pumps in microfluid systems," *Sensors and Actuators*, A46–47:557–561 (1995).

Perkin Elmer Cetus, Gene Amp DNA Amplification Reagent Kit, insert, Oct. 1988.

Church et al, Proc. Natl. Acad. Sci., 81:1991–1995 (Apr., 1984).

Chetverin et al., Bio/Technology, 12:1093–1099 (Nov. 1994).

Coulson et al, Proc. Natl. Acad. Sci. USA, 83:7821–7825 (Oct. 1986).

Dower et al, Ann. Rep. Med. Chem., 26:271–280 (1991).

Dramanac et al, J. Biomol. Struct. Dyn., 8(5):1085–1102 (1991).

Hodgson et al, Nucl. Acids Res., 15(15):6295 (1987).

Khrapko et al, DNA Seq. Map, 1;375–388 (1991).

Lander et al, Genomics, 2:231–239 (1988).

Little, Nature, 346:611–612 (1990).

Lysov et al, Dokl. Akad. Nauk. SSSR, 303:1508–1511 (1988).

Olson et al, Proc. Natl. Acad. Sci. USA, 83:7826–7830 (Oct. 1986).

Pevzner, Algorithmica, 13(1–2):77–105 (1995).

Pevzner et al, Algorithmica, 13(1–2):135–154 (1995).

Pfeifer et al, Science, 246:810–813 (Nov. 10, 19889).

Seed, Nucl. Acids Res., 10(5):1799–1810 (1982).

Wood et al, Proc. Natl. Acad. Sci. USA, 82:1585–1588 (1985).

Feinberg et al, Anal. Biochem., 137:266–267 (1984).

Pevzner et al, Adv. Applied Math, 14:139–171 (1993).

Schena et al, Proc. Natl. Acad. Sci. USA, 93:10614–10619 (Oct. 1996).

Bannwarth "Gene technology: A challenge for a chemist" Chimia 1987, 41:302–317.

Bannwarth et al. "A system for the simultaneous chemical synthesis of different DNA fragments on solid support" DNA 1986, 5:413–419.

Brenner et al. "In vitro cloning of complex mixtures of DNA on microbeads: Physical separation of differentially expressed cDNAs" Prod Natl Acad Sci USA 2000, 97:1665–1670.

Brenner et al. "Gene expression analysis by massively parallel signature sequencing (MPSS) on microbead arrays" Nature Biotechnology 2000, 18:630–634.

Tyagi "Taking a census of mRNA populations with microbeads" Nature Biotechnology 2000, 18:597–598.

Wada (chairman) *Hayashibara Intl Worshop on Automatic and High Speed DNA–Base Sequencing* 1987 pp. 1–63.

Miller et al. "Detection of bacteria by hybridization of rRNA with DNA–latex and immunodetection of hybrids" J Clin Microbiol 1988, 26:1271–1276.

\* cited by examiner

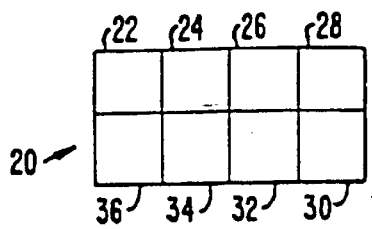
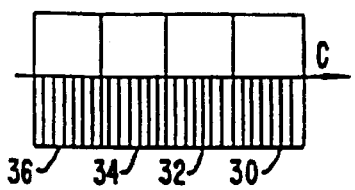
FIG. 2A    FIG. 2B
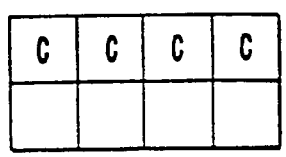
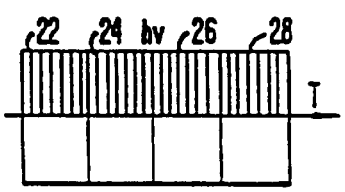
FIG. 2C    FIG. 2D
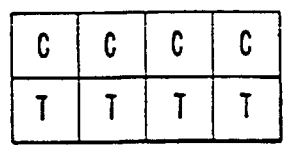
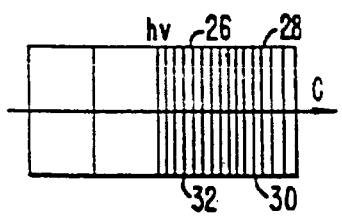
FIG. 2E    FIG. 2F
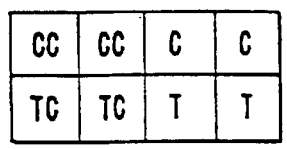
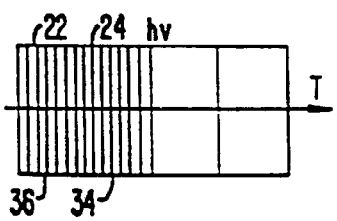
FIG. 2G    FIG. 2H
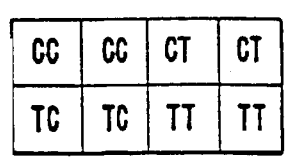
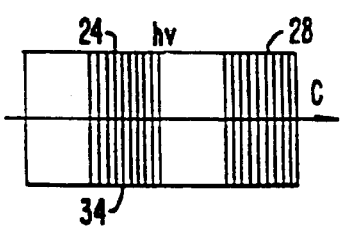
FIG. 2I    FIG. 2J
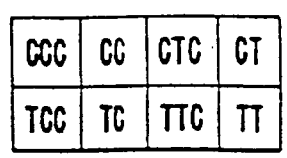
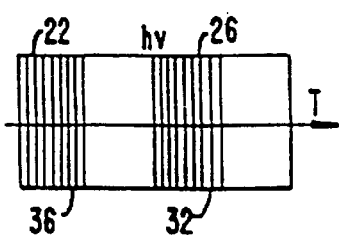
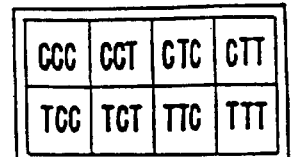
FIG. 2K    FIG. 2L    FIG. 2M

PRODUCTS FOR DETECTING NUCLEIC ACIDS

CROSS REFERENCE TO RELATED APPLICATIONS

This is a continuation of Appln. Ser. No. 09/362,098, filed Jul. 28, 1999; which is a divisional of Appln. Ser. No. 09/056,927, filed Apr. 8, 1998, now U.S. Pat. No. 6,197,506; which is a continuation of Appln. Ser. No. 08/670,118, filed Jun. 25, 1996, now U.S. Pat. No. 5,800,992; which is a divisional of Appln. Ser. No. 08/168,904, filed Dec. 15, 1993, now abandoned; which is a continuation of Appln. Ser. No. 07/624,114, filed Dec. 6, 1990, now abandoned, which are hereby incorporated by reference.

Additional commonly assigned Appln. Ser. No. 07/492,462, filed Mar. 7, 1990, now U.S. Pat. No. 5,143,854; Appln. Ser. No. 07/362,901, filed Jun. 7, 1989, now abandoned; Appln. Ser. Nos. 07/624,120 and 07/626,730, both of which were filed on Dec. 6, 1990; Appln. Ser. No. 07/435,316, filed Nov. 13, 1989, now abandoned; and U.S. Pat. No. 5,252,743 are also hereby incorporated herein by reference.

BACKGROUND OF THE INVENTION

The present invention relates to the sequencing, fingerprinting, and mapping of polymers, particularly biological polymers. The inventions may be applied, for example, in the sequencing, fingerprinting, or mapping of nucleic acids, polypeptides, oligosaccharides, and synthetic polymers.

The relationship between structure and function of macromolecules is of fundamental importance in the understanding of biological systems. These relationships are important to understanding, for example, the functions of enzymes, structural proteins, and signalling proteins, ways in which cells communicate with each other, as well as mechanisms of cellular control and metabolic feedback.

Genetic information is critical in continuation of life processes. Life is substantially informationally based and its genetic content controls the growth and reproduction of the organism and its complements. Polypeptides, which are critical features of all living systems, are encoded by the genetic material of the cell. In particular, the properties of enzymes, functional proteins, and structural proteins are determined by the sequence of amino acids which make them up. As structure and function are integrally related, many biological functions may be explained by elucidating the underlying structural features which provide those functions. For this reason, it has become very important to determine the genetic sequences of nucleotides which encode the enzymes, structural proteins, and other effectors of biological functions. In addition to segments of nucleotides which encode polypeptides, there are many nucleotide sequences which are involved in control and regulation of gene expression.

The human genome project is directed toward determining the complete sequence of the genome of the human organism. Although such a sequence would not correspond to the sequence of any specific individual, it would provide significant information as to the general organization and specific sequences contained within segments from particular individuals. It would also provide mapping information which is very useful for further detailed studies. However, the need for highly rapid, accurate, and inexpensive sequencing technology is nowhere more apparent than in a demanding sequencing project such as this. To complete the sequencing of a human genome would require the determination of approximately $3 \times 10^9$, or 3 billion base pairs.

The procedures typically used today for sequencing include the Sanger dideoxy method, see, e.g., Sanger et al. (1977) *Proc. Natl. Acad. Sci. USA*, 74:5463–5467, or the Maxam and Gilbert method, see, e.g., Maxam et al., (1980) *Methods in Enzymolocy*, 65:499–559. The Sanger method utilizes enzymatic elongation procedures with chain terminating nucleotides. The Maxam and Gilbert method uses chemical reactions exhibiting specificity of reaction to generate nucleotide specific cleavages. Both methods require a practitioner to perform a large number of complex manual manipulations. These manipulations usually require isolating homogeneous DNA fragments, elaborate and tedious preparing of samples, preparing a separating gel, applying samples to the gel, electrophoresing the samples into this gel, working up the finished gel, and analyzing the results of the procedure.

Thus, a less expensive, highly reliable, and labor efficient means for sequencing biological macromolecules is needed. A substantial reduction in cost and increase in speed of nucleotide sequencing would be very much welcomed. In particular, an automated system would improve the reproducibility and accuracy of procedures. The present invention satisfies these and other needs.

SUMMARY OF THE INVENTION

The present invention provides improved methods useful for de novo sequencing of an unknown polymer sequence, for verification of known sequences, for fingerprinting polymers, and for mapping homologous segments within a sequence. By reducing the number of manual manipulations required and automating most of the steps, the speed, accuracy, and reliability of these procedures are greatly enhanced.

The production of a substrate having a matrix of positionally defined regions with attached reagents exhibiting known recognition specificity can be used for the sequence analysis of a polymer. Although most directly applicable to sequencing, the present invention is also applicable to fingerprinting, mapping, and general screening of specific interactions. The VLSIPS™ Technology (Very Large Scale Immobilized Polymer Synthesis) substrates will be applied to evaluating other polymers, e.g., carbohydrates, polypeptides, hydrocarbon synthetic polymers, and the like. For these non-polynucleotides, the sequence specific reagents will usually be antibodies specific for a particular subunit sequence.

According to one aspect of the masking technique, the invention provides an ordered method for forming a plurality of polymer sequences by sequential addition of reagents comprising the step of serially protecting and deprotecting portions of the plurality of polymer sequences for addition of other portions of the polymer sequences using a binary synthesis strategy.

The present invention also provides a means to automate sequencing manipulations. The automation of the substrate production method and of the scan and analysis steps minimizes the need for human intervention. This simplifies the tasks and promotes reproducibility.

The present invention provides a composition comprising a plurality of positionally distinguishable sequence specific reagents attached to a solid substrate, which reagents are capable of specifically binding to a predetermined subunit sequence of a preselected multi-subunit length having at least three subunits, said reagents representing substantially all possible sequences of said preselected length. In some embodiments, the subunit sequence is a polynucleotide or a polypeptide, in others the preselected multi-subunit length is five subunits and the subunit sequence is a polynucleotide sequence. In other embodiments, the specific reagent is an oligonucleotide of at least about five nucleotides. Alternatively, the specific reagent is a monoclonal antibody. Usually the specific reagents are all attached to a single solid substrate, and the reagents comprise about 3000 different sequences. In other embodiments, the reagents represents at least about 25% of the possible subsequences of said preselected length. Usually, the reagents are localized in regions of the substrate having a density of at least 25 regions per square centimeter, and often the substrate has a surface area of less than about 4 square centimeters.

The present invention also provides methods for analyzing a sequence of a polynucleotide or a polypeptide, said method comprising the step of:

a) exposing said polynucleotide or polypeptide to a composition as described.

It also provides useful methods for identifying or comparing a target sequence with a reference, said method comprising the step of:

a) exposing said target sequence to a composition as described;

b) determining the pattern of positions of the reagents which specifically interact with the target sequence; and c) comparing the pattern with the pattern exhibited by the reference when exposed to the composition.

The present invention also provides methods for sequencing a segment of a polynucleotide comprising the steps of:

a) combining:
 i) a substrate comprising a plurality of chemically synthesized and positionally distinguishable oligonucleotides capable of recognizing defined oligonucleotide sequences; and
 ii) a target polynucleotide; thereby forming high fidelity matched duplex structures of complementary subsequences of known sequence; and b) determining which of said reagents have specifically interacted with subsequences in said target polynucleotide.

In one embodiment, the segment is substantially the entire length of said polynucleotide.

The invention also provides methods for sequencing a polymer, said method comprising the steps of:

a) preparing a plurality of reagents which each specifically bind to a subsequence of preselected length;

b) positionally attaching each of said reagents to one or more solid phase substrates, thereby producing substrates of positionally definable sequence specific probes;

c) combining said substrates with a target polymer whose sequence is to be determined; and d) determining which of said reagents have specifically interacted with subsequences in said target polymer.

In one embodiment, the substrates are beads. Preferably, the plurality of reagents comprise substantially all possible subsequences of said preselected length found in said target. In another embodiment, the solid phase substrate is a single substrate having attached thereto reagents recognizing substantially all possible subsequences of preselected length found in said target.

In another embodiment, the method further comprises the step of analyzing a plurality of said recognized subsequences to assemble a sequence of said target polymer. In a bead embodiment, at least some of the plurality of substrates have one subsequence specific reagent attached thereto, and the substrates are coded to indicate the sequence specificity of said reagent.

The present invention also embraces a method of using a fluorescent nucleotide to detect interactions with oligonucleotide probes of known sequence, said method comprising:

a) attaching said nucleotide to a target unknown polynucleotide sequence, and b) exposing said target polynucleotide sequence to a collection of positionally defined oligonucleotide probes of known sequences to determine the sequences of said probes which interact with said target.

In a further refinement, an additional step is included of:

a) collating said known sequences to determine the overlaps of said known sequences to determine the sequence of said target sequence.

A method of mapping a plurality of sequences relative to one another is also provided, the method comprising:

a) preparing a substrate having a plurality of positionally attached sequence specific probes;

b) exposing each of said sequences to said substrate, thereby determining the patterns of interaction between said sequence specific probes and said sequences; and c) determining the relative locations of said sequence specific probe interactions on said sequences to determine the overlaps and order of said sequences.

In one refinement, the sequence specific probes are oligonucleotides, applicable to where the target sequences are nucleic acid sequences.

In the nucleic acid sequencing application, the steps of the sequencing process comprise:

a) producing a matrix substrate having known positionally defined regions of known sequence specific oligonucleotide probes;

b) hybridizing a target polynucleotide to the positions on the matrix so that each of the positions which contain oligonucleotide probes complementary to a sequence on the target hybridize to the target molecule;

c) detecting which positions have bound the target, thereby determining sequences which are found on the target; and d) analyzing the known sequences contained in the target to determine sequence overlaps and assembling the sequence of the target therefrom.

The enablement of the sequencing process by hybridization is based in large part upon the ability to synthesize a large number (e.g., to virtually saturate) of the possible overlapping sequence segments and distinguishing those probes which hybridize with fidelity from those which have mismatched bases, and to analyze a highly complex pattern of hybridization results to determine the overlap regions.

The detecting of the positions which bind the target sequence would typically be through a fluorescent label on the target. Although a fluorescent label is probably most convenient, other sorts of labels, e.g., radioactive, enzyme linked, optically detectable, or spectroscopic labels may be used. Because the oligonucleotide probes are positionally defined, the location of the hybridized duplex will directly translate to the sequences which hybridize. Thus, analysis of the positions provides a collection of subsequences found within the target sequence. These subsequences are matched with respect to their overlaps so as to assemble an intact target sequence.

BRIEF DESCRIPTION OF THE DRAWINGS

FIG. 2A–M illustrates the process of a VLSIPS™ Technology trinucleotide synthesis.

DESCRIPTION OF THE PREFERRED EMBODIMENTS

Figure 1:
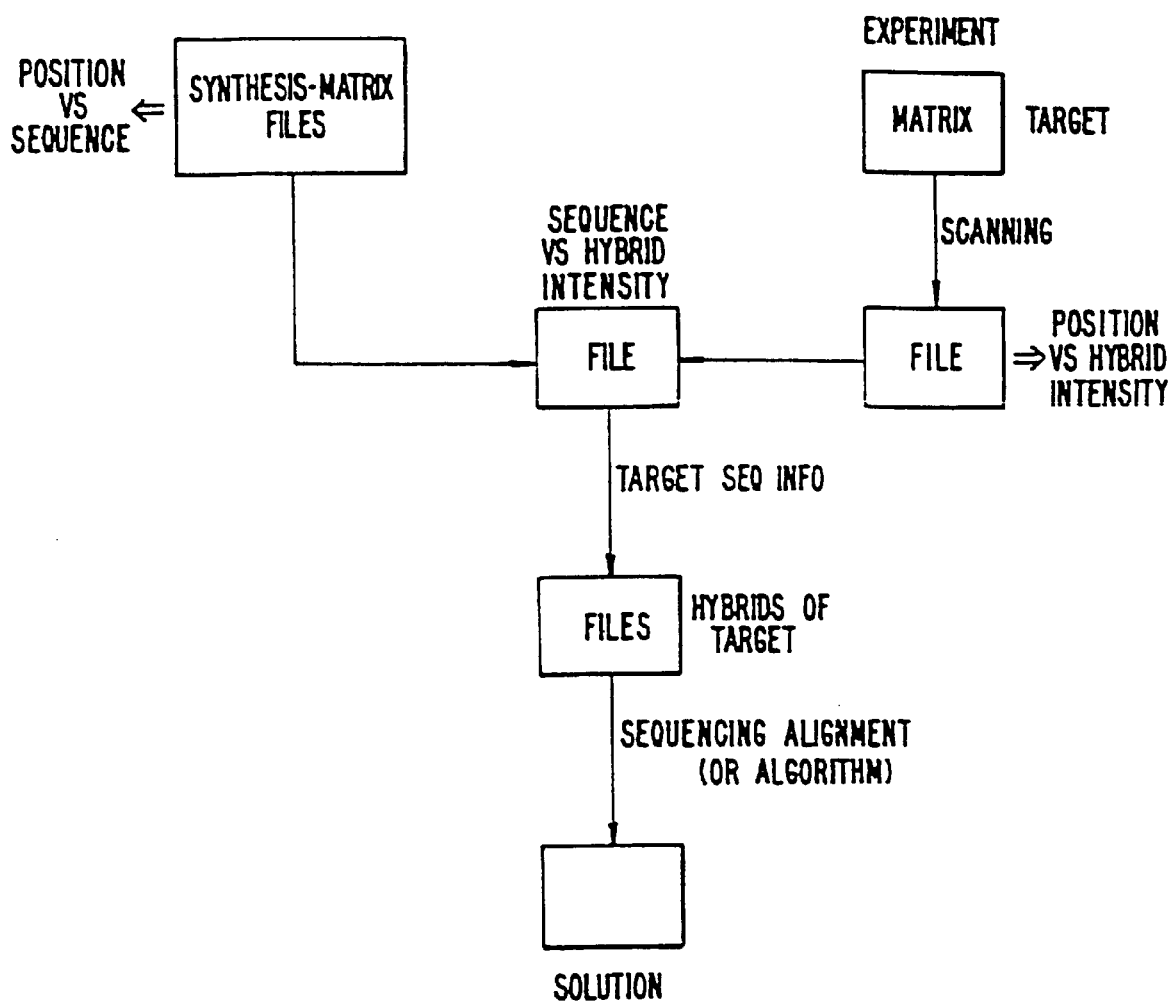
FIG. 1 illustrates a flow chart for sequence, fingerprint, or mapping analysis.

I. Overall Description
A. general
B. VLSIPS substrates
C. binary masking
D. applications
E. detection methods and apparatus
F. data analysis
II. Theoretical Analysis
A. simple n-mer structure; theory
B. complications
C. non-polynucleotide embodiments
III. Polynucleotide Sequencing
A. preparation of substrate matrix
B. labeling target polynucleotide
C. hybridization conditions
D. detection; VLSIPS scanning
E. analysis
F. substrate reuse
G. non-polynucleotide aspects
IV. Fingerprinting
A. general
B. preparation of substrate matrix
C. labeling target nucleotides
D. hybridization conditions
E. detection; VLSIPS scanning
F. analysis
G. substrate reuse
H. non-polynucleotide aspects
V. Mapping
A. general
B. preparation of substrate matrix
C. labeling
D. hybridization/specific interaction
E. detection
F. analysis
G. substrate reuse
H. non-polynucleotide aspects
VI. Additional Screening
A. specific interactions
B. sequence comparisons
C. categorizations
D. statistical correlations
VII. Formation of Substrate
A. instrumentation
B. binary masking
C. synthetic methods
D. surface immobilization
VIII. Hybridization/Specific Interaction
A. general
B. important parameters
IX. Detection Methods
A. labeling techniques
B. scanning system
X. Data Analysis
A. general
B. hardware
C. software
XI. Substrate Reuse
A. removal of label
B. storage and preservation
C. processes to avoid degradation of oligomers
XII. Integrated Sequencing Strategy
A. initial mapping strategy
B. selection of smaller clones
C. actual sequencing procedures
XIII. Commercial Applications
A. sequencing
B. fingerprinting
C. mapping

I. OVERALL DESCRIPTION

A. General

The present invention relies in part on the ability to synthesize or attach specific recognition reagents at known locations on a substrate, typically a single substrate. In particular, the present invention provides the ability to prepare a substrate having a very high density matrix pattern of positionally defined specific recognition reagents. The reagents are capable of interacting with their specific targets while attached to the substrate, e.g., solid phase interactions, and by appropriate labeling of these targets, the sites of the interactions between the target and the specific reagents may be derived. Because the reagents are positionally defined, the sites of the interactions will define the specificity of each interaction. As a result, a map of the patterns of interactions with specific reagents on the substrate is convertible into information on the specific interactions taking place, e.g., the recognized features. Where the specific reagents recognize a large number of possible features, this system allows the determination of the combination of specific interactions which exist on the target molecule. Where the number of features is sufficiently large, the identical same combination, or pattern, of features is sufficiently unlikely that a particular target molecule may often be uniquely defined by its features. In the extreme, the features may actually be the subunit sequence of the target molecule, and a given target sequence may be uniquely defined by its combination of features.

In particular, the methodology is applicable to sequencing polynucleotides. The specific sequence recognition reagents will typically be oligonucleotide probes which hybridize with specificity to subsequences found on the target sequence. A sufficiently large number of those probes allows the fingerprinting of a target polynucleotide or the relative mapping of a collection of target polynucleotides, as described in greater detail below.

In the high resolution fingerprinting provided by a saturating collection of probes which include all possible subsequences of a given size, e.g., 10-mers, collating of all the subsequences and determination of specific overlaps will be derived and the entire sequence can usually be reconstructed.

Although a polynucleotide sequence analysis is a preferred embodiment, for which the specific reagents are most easily accessible, the invention is also applicable to analysis of other polymers, including polypeptides, carbohydrates, and synthetic polymers, including $\alpha$-, $\beta$-, and $\omega$-amino acids, polyurethanes, polyesters, polycarbonates, polyureas, polyamides, polyethyleneimines, polyarylene sulfides, polysiloxanes, polyimides, polyacetates, and mixed polymers. Various optical isomers, e.g., various D- and L- forms of the monomers, may be used.

Sequence analysis will take the form of complete sequence determination, to the level of the sequence of individual subunits along the entire length of the target sequence. Sequence analysis also takes the form of sequence homology, e.g., less than absolute subunit resolution, where "similarity" in the sequence will be detectable, or the form of selective sequences of homology interspersed at specific or irregular locations.

In either case, the sequence is determinable at selective resolution or at particular locations. Thus, the hybridization method will be useful as a means for identification, e.g., a "fingerprint", much like a Southern hybridization method is used. It is also useful to map particular target sequences.

B. VLSIPS™ Technology

The invention is enabled by the development of technology to prepare substrates on which specific reagents may be either positionally attached or synthesized. In particular, the very large scale immobilized polymer synthesis (VLSIPS™) technology allows for the very high density production of an enormous diversity of reagents mapped out in a known matrix pattern on a substrate. These reagents specifically recognize subsequences in a target polymer and bind thereto, producing a map of positionally defined regions of interaction. These map positions are convertible into actual features recognized, and thus would be present in the target molecule of interest.

As indicated, the sequence specific recognition reagents will often be oligonucleotides which hybridize with fidelity and discrimination to the target sequence. For use with other polymers, monoclonal or polyclonal antibodies having high sequence specificity will often be used.

In the generic sense, the VLSIPS technology allows the production of a substrate with a high density matrix of positionally mapped regions with specific recognition reagents attached at each distinct region. By use of protective groups which can be positionally removed, or added, the regions can be activated or deactivated for addition of particular reagents or compounds. Details of the protection are described below and in related Pirrung et al. (1992) U.S. Pat. No. 5,143,854. In a preferred embodiment, photosensitive protecting agents will be used and the regions of activation or deactivation may be controlled by electro-optical and optical methods, similar to many of the processes used in semiconductor wafer and chip fabrication.

In the nucleic acid nucleotide sequencing application, a VLSIPS substrate is synthesized having positionally defined oligonucleotide probes. See Pirrung et al. (1992) U.S. Pat. No. 5,143,854; and U.S. Ser. No. 07/624,120, now abandoned. By use of masking technology and photosensitive synthetic subunits, the VLSIPS apparatus allows for the stepwise synthesis of polymers according to a positionally defined matrix pattern. Each oligonucleotide probe will be synthesized at known and defined positional locations on the substrate. This forms a matrix pattern of known relationship between position and specificity of interaction. The VLSIPS technology allows the production of a very large number of different oligonucleotide probes to be simultaneously and automatically synthesized including numbers in excess of about $10^2$, $10^3$, $10^4$, $10^5$, $10^6$, or even more, and at densities of at least about $10^2$, $10^3/cm^2$, $10^4/cm^2$, $10^5/cm^2$ and up to $10^6/cm^2$ or more. This application discloses methods for synthesizing polymers on a silicon or other suitably derivatized substrate, methods and chemistry for synthesizing specific types of biological polymers on those substrates, apparatus for scanning and detecting whether interaction has occurred at specific locations on the substrate, and various other technologies related to the use of a high density very large scale immobilized polymer substrate. In particular, sequencing, fingerprinting, and mapping applications are discussed herein in detail, though related technologies are described in simultaneously filed applications U.S. Ser. No. 07/624,120, now abandoned; and U.S. Ser. No. 07/517,659; Dower et al. (1995) U.S. Pat. No. 5,427,908, each of which is hereby incorporated herein by reference.

In other embodiments, antibody probes will be generated which specifically recognize particular subsequences found on a polymer. Antibodies would be generated which are specific for recognizing a three contiguous amino acid sequence, and monoclonal antibodies may be preferred. Optimally, these antibodies would not recognize any sequences other than the specific three amino acid stretch desired and the binding affinity should be insensitive to flanking or remote sequences found on a target molecule. Likewise, antibodies specific for particular carbohydrate linkages or sequences will be generated. A similar approach could be used for preparing specific reagents which recognize other polymer subunit sequences. These reagents would typically be site specifically localized to a substrate matrix pattern where the regions are closely packed.

These reagents could be individually attached at specific sites on the substrate in a matrix by an automated procedure where the regions are positionally targeted by some other specific mechanism, e.g., one which would allow the entire collection of reagents to be attached to the substrate in a single reaction. Each reagent could be separately attached to a specific oligonucleotide sequence by an automated procedure. This would produce a collection of reagents where, e.g., each monoclonal antibody would have a unique oligonucleotide sequence attached to it. By virtue of a VLSIPS substrate which has different complementary oligonucleotides synthesized on it, each monoclonal antibody would specifically be bound only at that site on the substrate where the complementary oligonucleotide has been synthesized. A crosslinking step would fix the reagent to the substrate. See, e.g., Dattagupta et al. (1985) U.S. Pat. No. 4,542,102 and (1987) U.S. Pat. No. 4,713,326; and Chatterjee, M. et al. (1990) *J. Am. Chem. Soc.* 112:6397–6399, which are hereby incorporated herein by reference. This allows a high density positionally specific collection of specific recognition reagents, e.g., monoclonal antibodies, to be immobilized to a solid substrate using an automated system.

The regions which define particular reagents will usually be generated by selective protecting groups which may be activated or deactivated. Typically the protecting group will be bound to a monomer subunit or spatial region, and can be spatially affected by an activator, such as electromagnetic radiation. Examples of protective groups with utility herein include nitroveratryl oxycarbonyl (NVOC), nitrobenzyl oxycarbony (NBOC), dimethyl dimethoxy benzyloxy carbonyl, 5-bromo-7-nitroindolinyl, O-hydroxy-α-methyl cinnamoyl, and 2-oxymethylene anthraquinone. Examples of activators include ion beams, electric fields, magnetic fields, electron beams, x-ray, and other forms of electromagnetic radiation.

C. Binary Masking

In fact, the means for producing a substrate useful for these techniques are explained in Pirrung et al. (1992) U.S. Pat. No. 5,143,854, which is hereby incorporated herein by reference. However, there are various particular ways to optimize the synthetic processes. Many of these methods are described in Ser. No. 07/624,120, now abandoned.

Briefly, the binary synthesis strategy refers to an ordered strategy for parallel synthesis of diverse polymer sequences by sequential addition of reagents which may be represented by a reactant matrix, and a switch matrix, the product of which is a product matrix. A reactant matrix is a 1×n matrix of the building blocks to be added. The switch matrix is all or a subset of the binary numbers from 1 to n arranged in columns. In preferred embodiments, a binary strategy is one in which at least two successive steps illuminate half of a region of interest on the substrate. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme, but will still be considered to be a binary masking scheme within the definition herein. A binary "masking" strategy is a binary synthesis which uses light to remove protective groups from materials for addition of other materials such as nucleotides or amino acids.

In particular, this procedure provides a simplified and highly efficient method for saturating all possible sequences of a defined length polymer. This masking strategy is also particularly useful in producing all possible oligonucleotide sequence probes of a given length.

D. Applications

The technology provided by the present invention has very broad applications. Although described specifically for polynucleotide sequences, similar sequencing, fingerprinting, mapping, and screening procedures can be applied to polypeptide, carbohydrate, or other polymers. In particular, the present invention may be used to completely sequence a given target sequence to subunit resolution. This may be for de novo sequencing, or may be used in conjunction with a second sequencing procedure to provide independent verification. See, e.g., (1988) *Science* 242:1245. For example, a large polynucleotide sequence defined by either the Maxam and Gilbert technique or by the Sanger technique may be verified by using the present invention.

In addition, by selection of appropriate probes, a polynucleotide sequence can be fingerprinted. Fingerprinting is a less detailed sequence analysis which usually involves the characterization of a sequence by a combination of defined features. Sequence fingerprinting is particularly useful because the repertoire of possible features which can be tested is virtually infinite. Moreover, the stringency of matching is also variable depending upon the application. A Southern Blot analysis may be characterized as a means of simple fingerprint analysis.

Fingerprinting analysis may be performed to the resolution of specific nucleotides, or may be used to determine homologies, most commonly for large segments. In particular, an array of oligonucleotide probes of virtually any workable size may be positionally localized on a matrix and used to probe a sequence for either absolute complementary matching, or homology to the desired level of stringency using selected hybridization conditions.

In addition, the present invention provides means for mapping analysis of a target sequence or sequences. Mapping will usually involve the sequential ordering of a plurality of various sequences, or may involve the localization of a particular sequence within a plurality of sequences. This may be achieved by immobilizing particular large segments onto the matrix and probing with a shorter sequence to determine which of the large sequences contain that smaller sequence. Alternatively, relatively shorter probes of known or random sequence may be immobilized to the matrix and a map of various different target sequences may be determined from overlaps. Principles of such an approach are described in some detail by Evans et al. (1989) "Physical Mapping of Complex Genomes by Cosmid Multiplex Analysis," *Proc. Natl. Acad. Sci. USA* 86:5030–5034; Michiels et al. (1987) "Molecular Approaches to Genome Analysis: A Strategy for the Construction of Ordered Overlap Clone Libraries," *CABIOS* 3:203–210; Olsen et al. (1986) "Random-Clone Strategy for Genomic Restriction Mapping in Yeast," *Proc. Natl. Acad. Sci. USA* 83:7826–7830; Craig, et al. (1990) "Ordering of Cosmid Clones Covering the Herpes Simplex Virus Type I (HSV-I) Genome: A Test Case for Fingerprinting by Hybridization," *Nuc. Acids Res.* 18:2653–2660; and Coulson, et al. (1986) "Toward a Physical Map of the Genome of the Nematode Caenorhabditis elegans," *Proc. Natl. Acad. Sci. USA* 83:7821–7825; each of which is hereby incorporated herein by reference.

Fingerprinting analysis also provides a means of identification. In addition to its value in apprehension of criminals from whom a biological sample, e.g., blood, has been collected, fingerprinting can ensure personal identification for other reasons. For example, it may be useful for identification of bodies in tragedies such as fire, flood, and vehicle crashes. In other cases the identification may be useful in identification of persons suffering from amnesia, or of missing persons. Other forensics applications include establishing the identity of a person, e.g., military identification "dog tags", or may be used in identifying the source of particular biological samples. Fingerprinting technology is described, e.g., in Carrano, et al. (1989) "A High-Resolution, Fluorescence-Based, Semi-automated method for DNA Fingerprinting," *Genomics* 4: 129–136, which is hereby incorporated herein by reference. See, e.g., table I, for nucleic acid applications, and corresponding applications may be accomplished using polypeptides.

TABLE I

VLSIPS™ TECHNOLOGY IN NUCLEIC ACIDS
I. Construction of Chips
II. Applications
  A. Sequencing
    1. Primary sequencing
    2. Secondary sequencing (sequence checking)
    3. Large scale mapping
    4. Fingerprinting
  B. Duplex/Triplex formation
    1. Antisense
    2. Sequence specific function modulation (e.g. promoter inhibition)
  C. Diagnosis
    1. Genetic markers
    2. Type markers a. Blood donors b. Tissue transplants
  D. Microbiology
    1. Clinical microbiology
    2. Food microbiology
III. Instrumentation
  A. Chip machines
  B. Detection IV. Software Development
  A. Instrumentation software
  B. Data reduction software
  C. Sequence analysis software The fingerprinting analysis may be used to perform various types of genetic screening. For example, a single substrate may be generated with a plurality of screening probes, allowing for the simultaneous genetic screening for a large number of genetic markers. Thus, prenatal or diagnostic screening can be simplified, economized, and made more generally accessible.

In addition to the sequencing, fingerprinting, and mapping applications, the present invention also provides means for determining specificity of interaction with particular sequences. Many of these applications were described in Ser. No. 07/362,901, now abandoned, Pirrung et al. (1992) U.S. Pat. No. 5,143,854; Ser. No. 07/435,316, and Ser. No. 07/612,671.

E. Detection Methods and Apparatus

An appropriate detection method applicable to the selected labeling method can be selected. Suitable labels include radionucleotides, enzymes, substrates, cofactors, inhibitors, magnetic particles, heavy metal atoms, and particularly fluorescers, chemiluminescers, and spectroscopic labels. Patents teaching the use of such labels include U.S. Pat. Nos. 3,817,837; 3,850,752; 3,939,350; 3,996,345; 4,277,437; 4,275,149; and 4,366,241.

With an appropriate label selected, the detection system best adapted for high resolution and high sensitivity detection may be selected. As indicated above, an optically detectable system, e.g., fluorescence or chemiluminescence would be preferred. Other detection systems may be adapted to the purpose, e.g., electron microscopy, scanning electron microscopy (SEM), scanning tunneling electron microscopy (STEM), infrared microscopy, atomic force microscopy (AFM), electrical condutance, and image plate transfer.

With a detection method selected, an apparatus for scanning the substrate will be designed. Apparatus, as described in Ser. No. 07/362,901, now abandoned; or Pirrung et al. (1992) U.S. Pat. No. 5,143,854; or Ser. No. 07/624,120, now abandoned, are particularly appropriate. Design modifications may also be incorporated therein.

F. Data Analysis

Data is analyzed by processes similar to those described below in the section describing theoretical analysis. More efficient algorithms will be mathematically devised, and will usually be designed to be performed on a computer. Various computer programs which may more quickly or efficiently make measurement samples and distinguish signal from noise will also be devised. See, particularly, Ser. No. 07/624,120, now abandoned.

The initial data resulting from the detection system is an array of data indicative of fluorescent intensity versus location on the substrate. The data are typically taken over regions substantially smaller than the area in which synthesis of a given polymer has taken place. Merely by way of example, if polymers were synthesized in squares on the substrate having dimensions of 500 microns by 500 microns, the data may be taken over regions having dimensions of 5 microns by 5 microns. In most preferred embodiments, the regions over which florescence data are taken across the substrate are less than about ½ the area of the regions in which individual polymers are synthesized, preferably less than 1/10 the area in which a single polymer is synthesized, and most preferably less than 1/100 the area in which a single polymer is synthesized. Hence, within any area in which a given polymer has been synthesized, a large number of fluorescence data points are collected.

A plot of number of pixels versus intensity for a scan should bear a rough resemblance to a bell curve, but spurious data are observed, particularly at higher intensities. Since it is desirable to use an average of fluorescent intensity over a given synthesis region in determining relative binding affinity, these spurious data will tend to undesirably skew the data.

Accordingly, in one embodiment of the invention the data are corrected for removal of these spurious data points, and an average of the data points is thereafter utilized in determining relative binding efficiency. In general the data are fitted to a base curve and statistical measures are used to remove spurious data.

In an additional analytical tool, various degeneracy reducing analogues may be incorporated in the hybridization probes. Various aspects of this strategy are described, e.g., in Macevicz, S. (1990) PCT publication number WO 90/04652, which is hereby incorporated herein by reference.

II. Thoretical Analysis

The principle of the hybridization sequencing procedure is based, in part, upon the ability to determine overlaps of short segments. The VLSIPS technology provides the ability to generate reagents which will saturate the possible short subsequence recognition possibilities. The principle is most easily illustrated by using a binary sequence, such as a sequence of zeros and ones. Once having illustrated the application to a binary alphabet, the principle may easily be understood to encompass three letter, four letter, five or more letter, even 20 letter alphabets. A theoretical treatment of analysis of subsequence information to reconstruction of a target sequence is provided, e.e., in Lysov, Yu., et al. (1988) *Doklady Akademi. Nauk. SSR* 303:1508–1511; Khrapko K., et al. (1989) *FEBS Letters* 256:118–122; Pevzner, P. (1989) *J. of Biomolecular Structure and Dynamics* 7:63–69; and Drmanac, R. et al. (1989) *Genomics* 4:114–128; each of which is hereby incorporated herein by reference.

The reagents for recognizing the subsequences will usually be specific for recognizing a particular polymer subsequence anywhere within a target polymer. It is preferable that conditions may be devised which allow absolute discrimination between high fidelity matching and very low levels of mismatching. The reagent interaction will preferably exhibit no sensitivity to flanking sequences, to the subsequence position within the target, or to any other remote structure within the sequence. For polynucleotide sequencing, the specific reagents can be oligonucleotide probes; for polypeptides and carbohydrates, antibodies will be useful reagents. Antibody reagents should also be useful for other types of polymers.

A. Simple n-mer Structure: Theory
  1. Simple Two Letter Alphabet: example

A simple example is presented below of how a sequence of ten digits comprising zeros and ones would be sequenceable using short segments of five digits. For example, consider the sample ten digit sequence:

1010011100.

A VLSIPS™ Technology substrate could be constructed, as discussed elsewhere, which would have reagents attached in a defined matrix pattern which specifically recognize each of the possible five digit sequences of ones and zeros. The number of possible five digit subsequences is $2^5=32$. The number of possible different sequences 10 digits long is $2^{10}=1,024$. The five contiguous digit subsequences within a ten digit sequence number six, i.e., positioned at digits 1–5, 2–6, 3–7, 4–8, 5–9, and 6–10. It will be noted that the specific order of the digits in the sequence is important and that the order is directional, e.g., running left to right versus right to left. The first five digit sequence contained in the target sequence is 10100. The second is 01001, the third is 10011, the fourth is 00111, the fifth is 01110, and the sixth is 11100.

The VLSIPS™ substrate would have a matrix pattern of positionally attached reagents which recognize each of the different 5-mer subsequences. Those reagents which recognize each of the 6 contained 5-mers will bind the target, and a label allows the positional determination of where the sequence specific interaction has occurred. By correlation of the position in the matrix pattern, the corresponding bound subsequences can be determined.

In the above-mentioned sequence, six different 5-mer sequences would be determined to be present. They would be:
10100
 01001
  10011
   00111
    01110
     11100

Any sequence which contains the first five digit sequence, 10100, already narrows the number of possible sequences (e.g., from 1024 possible sequences) which contain it to less than about 192 possible sequences.

This 192 is derived from the observation that with the subsequence 10100 at the far left of the sequence, in positions 1–5, there are only 32 possible sequences. Likewise, for that particular subsequence in positions 2–6, 3–7, 4–8, 5–9, and 6–10. So, to sum up all of the sequences that could contain 10100, there are 32 for each position and 6 positions for a total of about 192 possible sequences. However, some of these 10 digit sequences will have been counted twice. Thus, by virtue of containing the 10100 subsequence, the number of possible 10-mer sequences has been decreased from 1024 sequences to less than about 192 sequences.

In this example, not only do we know that the sequence contains 10100, but we also know that it contains the second five character sequence, 01001. By virtue of knowing that the sequence contains 10100, we can look specifically to determine whether the sequence contains a subsequence of five characters which contains the four leftmost digits plus a next digit to the left. For example, we would look for a sequence of X1010, but we find that there is none. Thus, we know that the 10100 must be at the left end of the 10-mer. We would also look to see whether the sequence contains the rightmost four digits plus a next digit to the right, e.g., 0100X. We find that the sequence also contains the sequence 01001, and that X is a 1. Thus, we know at least that our target sequence has an overlap of 0100 and has the left terminal sequence 101001.

Applying the same procedure to the second 5-mer, we also know that the sequence must include a sequence of five digits having the sequence 1001Y where Y must be either 0 or 1. We look through the fragments and we see that we have a 10011 sequence within our target, thus Y is also 1. Thus, we would know that our sequence has a sequence of the first seven being 1010011.

Moving to the next 5-mer, we know that there must be a sequence of 0011Z, where Z must be either 0 or 1. We look at the fragments produced above and see that the target sequence contains a 00111 subsequence and Z is 1. Thus, we know the sequence must start with 10100111.

The next 5-mer must be of the sequence 0111W where W must be 0 or 1. Again, looking up at the fragments produced, we see that the target sequence contains a 01110 subsequence, and W is a 0. Thus, our sequence to this point is 101001110. We know that the last 5-mer must be either 11100 or 11101. Looking above, we see that it is 11100 and that must be the last of our sequence. Thus, we have determined that our sequence must have been 1010011100.

However, it will be recognized from the example above with the sequences provided therein, that the sequence analysis can start with any known positive probe subsequence. The determination may be performed by moving linearly along the sequence checking the known sequence with a limited number of next positions. Given this possibility, the sequence may be determined, besides by scanning all possible oligonucleotide probe positions, by specifically looking only where the next possible positions would be. This may increase the complexity of the scanning but may provide a longer time span dedicated towards scanning and detecting specific positions of interest relative to other sequence possibilities. Thus, the scanning apparatus could be set up to work its way along a sequence from a given contained oligonucleotide to only look at those positions on the substrate which are expected to have a positive signal.

It is seen that given a sequence, it can be de-constructed into n-mers to produce a set of internal contiguous subsequences. From any given target sequence, we would be able to determine what fragments would result. The hybridization sequence method depends, in part, upon being able to work in the reverse, from a set of fragments of known sequences to the full sequence. In simple cases, one is able to start at a single position and work in either or both directions towards the ends of the sequence as illustrated in the example.

The number of possible sequences of a given length increases very quickly with the length of that sequence. Thus, a 10-mer of zeros and ones has 1024 possibilities, a 12-mer has 4096. A 20-mer has over a million possibilities, and a 30-mer has over a billion. However, a given 30-mer has, at most, 26 different internal 5-mer sequences. Thus, a 30 character target sequence having over a million possible sequences can be substantially defined by only 26 different 5-mers. It will be recognized that the probe oligonucleotides will preferably, but need not necessarily, be of identical length, and that the probe sequences need not necessarily be contiguous in that the overlapping subsequences need not differ by only a single subunit. Moreover, each position of the matrix pattern need not be homogeneous, but may actually contain a plurality of probes of known sequence. In addition, although all of the possible subsequence specifications would be preferred, a less than full set of sequences specifications could be used. In particular, although a substantial fraction will preferably be at least about 70%, it may be less than that. About 20% would be preferred, more preferably at least about 30% would be desired. Higher percentages would be especially preferred.

2. Example of Four Letter Alphabet

A four letter alphabet may be conceptualized in at least two different ways from the two letter alphabet. One way is to consider the four possible values at each position and to analogize in a similar fashion to the binary example each of the overlaps. A second way is to group the binary digits into groups.

Using the first means, the overlap comparisons are performed with a four letter alphabet rather than a two letter alphabet. Then, in contrast to the binary system with 10 positions where $2^{10}$=1024 possible sequences, in a 4-character alphabet with 10 positions, there will actually be $4^{10}=1,048,576$ possible sequences. Thus, the complexity of a four character sequence has a much larger number of possible sequences compared to a two character sequence. Note, however, that there are still only 6 different internal 5-mers. For simplicity, we shall examine a 5 character string with 3 character subsequences. Instead of only 1 and 0, the characters may be designated, e.g., A, C, G, and T. Let us take the sequence GGCTA. The 3-mer subsequences are:

GGC
 GCT
  CTA

Given these subsequences, there is one sequence, or at most only a few sequences which would produce that combination of subsequences, i.e., GGCTA.

Alternatively, with a four character universe, the binary system can be looked at in pairs of digits. The pairs would be 00, 01, 10, and 11. In this manner, the earlier used sequence 1010011100 is looked at as 10,10,01,11,00. Then the first character of two digits is selected from the possible universe of the four representations 00, 01, 10, and 11. Then a probe would be in an even number of digits, e.g., not five digits, but, three pairs of digits or six digits. A similar comparison is performed and the possible overlaps determined. The 3-pair subsequences are:

10,10,01
 10,01,11
  01,11,00 and the overlap reconstruction produces 10,10,01,11,00.

The latter of the two conceptual views of the 4 letter alphabet provides a representation which is similar to what would be provided in a digital computer. The applicability to a four nucleotide alphabet is easily seen by assigning, e.g., 00 to A, 01 to C, 10 to G, and 11 to T. And, in fact, if such a correspondence is used, both examples for the 4 character sequences can be seen to represent the same target sequence. The applicability of the hybridization method and its analysis for determining the ultimate sequence is easily seen if A is the representation of adenine, C is the representation of cytosine, G is the representation of guanine, and T is the representation of thymine or uracil.

3. Generalization to m-letter Alphabet

This reconstruction process may be applied to polymers of virtually any number of possible characters in the alphabet, and for virtually any length sequence to be sequenced, though limitations, as discussed below, will limit its efficiency at various extremes of length. It will be recognized that the theory can be applied to a large diversity of systems where sequence is important.

For example, the method could be applied to sequencing of a polypeptide. A polypeptide can have any of twenty natural amino acid possibilities at each position. A twenty letter alphabet is amenable to sequencing by this method so long as reagents exist for recognizing shorter subsequences therein. A preferred reagent for achieving that goal would be a set of monoclonal antibodies each of which recognizes a specific three contiguous amino acid subsequence. A complete set of antibodies which recognize all possible subsequences of a given length, e.g., 3 amino acids, and preferably with a uniform affinity, would be $20^3$=8000 reagents.

It will also be recognized that each target sequence which is recognized by the specific reagents need not have homogeneous termini. Thus, fragments of the entire target sequence will also be useful for hybridizing appropriate subsequences. It is, however, preferable that there not be a significant amount of labeled homogeneous contaminating extraneous sequences. This constraint does usually require the purification of the target molecule to be sequenced, but a specific label technique would dispense with a purification requirement if the unlabeled extraneous sequences do not interfere with the labeled sequences.

In addition, conformational effects of target polypeptide folding may, in certain embodiments, be negligible if the polypeptide is fragmented into sufficiently small peptides, or if the interaction is performed under conditions where conformation, but not specific interaction, is disrupted.

B. Complications

Two obvious complications exist with the method of sequence analysis by hybridization. The first results from a probe of inappropriate length while the second relates to internally repeated sequences.

The first obvious complication is a problem which arises from an inappropriate length of recognition sequence, which causes problems with the specificity of recognition. For example, if the recognized sequence is too short, every sequence which is utilized will be recognized by every probe sequence. This occurs, e.g., in a binary system where the probes are each of sequences which occur relatively frequently, e.g., a two character probe for the binary system. Each possible two character probe would be expected to appear ¼ of the time in every single two character position. Thus, the above sequence example would be recognized by each of the 00, 10, 01, and 11. Thus, the sequence information is virtually lost because the resolution is too low and each recognition reagent specifically binds at multiple sites on the target sequence.

The number of different probes which bind to a target depends on the relationship between the probe length and the target length. At the extreme of short probe length, the just mentioned problem exists of excessive redundancy and lack of resolution. The lack of stability in recognition will also be a problem with extremely short probes. At the extreme of long probe length, each entire probe sequence is on a different position of a substrate. However, a problem arises from the number of possible sequences, which goes up dramatically with the length of the sequence. Also, the specificity of recognition begins to decrease as the contribution to binding by any particular subunit may become sufficiently low that the system fails to distinguish the fidelity of recognition. Mismatched hybridization may be a problem with the polynucleotide sequencing applications, though the fingerprinting and mapping applications may not be so strict in their fidelity requirements. As indicated above, a thirty position binary sequence has over a million possible sequences, a number which starts to become unreasonably large in its required number of different sequences, even though the target length is still very short. Preparing a substrate with all sequence possibilities for a long target may be extremely difficult due to the many different oligomers which must be synthesized.

The above example illustrates how a long target sequence may be reconstructed with a reasonably small number of shorter subsequences. Since the present day resolution of the regions of the substrate having defined oligomer probes attached to the substrate approaches about 10 microns by 10 microns for resolvable regions, about $10^6$, or 1 million, positions can be placed on a one centimeter square substrate. However, high resolution systems may have particular disadvantages which may be outweighed using the lower density substrate matrix pattern. For this reason, a sufficiently large number of probe sequences can be utilized so that any given target sequence may be determined by hybridization to a relatively small number of probes.

A second complication relates to convergence of sequences to a single subsequence. This will occur when a particular subsequence is repeated in the target sequence. This problem can be addressed in at least two different ways. The first, and simpler way, is to separate the repeat sequences onto two different targets. Thus, each single target will not have the repeated sequence and can be analyzed to its end. This solution, however, complicates the analysis by requiring that some means for cutting at a site between the repeats can be located. Typically a careful sequencer would want to have two intermediate cut points so that the intermediate region can also be sequenced in both directions across each of the cut points. This problem is inherent in the hybridization method for sequencing but can be minimized by using a longer known probe sequence so that the frequency of probe repeats is decreased.

Knowing the sequence of flanking sequences of the repeat will simplify the use of polymerase chain reaction (PCR) or a similar technique to further definitively determine the sequence between sequence repeats. Probes can be made to hybridize to those known sequences adjacent the repeat sequences, thereby producing new target sequences for analysis. See, e.g., Innis et al. (eds.) (1990) *PCR Protocols: A Guide to Methods and Applications*, Academic Press; and methods for synthesis of oligonucleotide probes, see, e.g., Gait (1984) *Oligonucleotide Synthesis: A Practical Approach*, IRL Press, Oxford.

Other means for dealing with convergence problems include using particular longer probes, and using degeneracy reducing analogues, see, e.g., Macevicz, S. (1990) PCT publication number WO 90/04652, which is hereby incorporated herein by reference. By use of stretches of the degeneracy reducing analogues with other probes in particular combinations, the number of probes necessary to fully saturate the possible oligomer probes is decreased. For example, with a stretch of 12-mers having the central 4-mer of degenerate nucleotides, in combination with all of the possible 8-mers, the collection numbers twice the number of possible 8-mers, e.g. 65,536+65,536=131,072, but the population provides screening equivalent to all possible 12-mers.

By way of further explanation, all possible oligonucleotide 8-mers may be depicted in the fashion:

N1-N2-N3-N4-N5-N6-N7-N8, in which there are $4^8$=65,536 possible 8-mers. As described in Ser. No. 07/624,120, now abandoned, producing all possible 8-mers requires 4×8=32 chemical binary synthesis steps to produce the entire matrix pattern of 65,536 8-mer possibilities. By incorporating degeneracy reducing nucleotides, D's, which hybridize nonselectively to any corresponding complementary nucleotide, new oligonucleotides 12-mers can be made in the fashion:

N1-N2-N3-N4-D-D-D-D-N5-N6-N7-N8, in which there are again, as above, only $4^8$=65,536 possible "12-mers", which in reality only have 8 different nucleotides.

However, it can be seen that each possible 12-mer probe could be represented by a group of the two 8-mer types. Moreover, repeats of less than 12 nucleotides would not converge, or cause repeat problems in the analysis. Thus, instead of requiring a collection of probes corresponding to all 12-mers, or $4^{12}$=16,777,216 different 12-mers, the same information can be derived by making 2 sets of "8-mers" consisting of the typical 8-mer collection of $4^8$=65,536 and the "12-mer" set with the degeneracy reducing analogues, also requiring making $4^8$=65,536. The combination of the two sets, requires making 65,536+65,536=131,072 different molecules, but giving the information of 16,777,216 molecules. Thus, incorporating the degeneracy reducing analogue decreases the number of molecules necessary to get 12-mer resolution by a factor of about 128-fold.

C. Non-polynucleotide Embodiments

The above example is directed towards a polynucleotide embodiment. This application is relatively easily achieved because the specific reagents will typically be complementary oligonucleotides, although in certain embodiments other specific reagents may be desired. For example, there may be circumstances where other than complementary base pairing will be utilized. The polynucleotide targets, will usually be single strand, but may be double or triple stranded in various applications. However, a triple stranded specific interaction might be sometimes desired, or a protein or other specific binding molecule may be utilized. For example, various promoter or DNA sequence specific binding proteins might be used, including, e.g., restriction enzyme binding domains, other binding domains, and antibodies. Thus, specific recognition reagents besides oligonucleotides may be utilized.

For other polymer targets, the specific reagents will often be polypeptides. These polypeptides may be protein binding domains from enzymes or other proteins which display specificity for binding. Usually an antibody molecule may be used, and monoclonal antibodies may be particularly desired. Classical methods may be applied for preparing antibodies, see, e.g., Harlow and Lane (1988) *Antibodies: A Laboratory Manual* Cold Spring Harbor Press, New York; and Goding (1986) *Monoclonal Antibodies: Principles and Practice* (2d Ed.) Academic Press, San Diego. Other suitable techniques for in vitro exposure of lymphocytes to the antigens or selection of libraries of antibody binding sites are described, e.g., in Huse et al. (1989) *Science* 246:1275–1281; and Ward et al. 91989) *Nature* 341:544–546, each of which is hereby incorporated herein by reference. Unusual antibody production methods are also described, e.g., in Hendricks et al. (1989) *BioTechnology* 7:1271–1274; and Hiatt et al. (1989) *Nature* 342:76–78, each of which is hereby incorporated herein by reference. Other molecules which may exhibit specific binding interaction may be useful for attachment to a VLSIPS substrate by various methods, including the caged biotin methods, see, e.g., Ser. No. 07/435,316, now abandoned, and Barrett et al. (1993) U.S. Pat. No. 5,252,743.

The antibody specific reagents should be particularly useful for the polypeptide, carbohydrate, and synthetic polymer applications. Individual specific reagents might be generated by an automated process to generate the number of reagents necessary to advantageously use the high density positional matrix pattern. In an alternative approach, a plurality of hybridoma cells may be screened for their ability to bind to a VLSIPS matrix possessing the desired sequences whose binding specificity is desired. Each cell might be individually grown up and its binding specificity determined by VLSIPS apparatus and technology. An alternative strategy would be to expose the same VLSIPS matrix to a polyclonal serum of high titer. By a successively large volume of serum and different animals, each region of the VLSIPS substrate would have attached to it a substantial number of antibody molecules with specificity of binding. The substrate, with non-covalently bound antibodies could be derivatized and the antibodies transferred to an adjacent second substrate in the matrix pattern in which the antibody molecules had attached to the first matrix. If the sensitivity of detection of binding interaction is sufficiently high, such a low efficiency transfer of antibody molecules may produce a sufficiently high signal to be useful for many purposes, including the sequencing applications.

In another embodiment, capillary forces may be used to transfer the selected reagents to a new matrix, to which the reagents would be positionally attached in the pattern of the recognized sequences. Or, the reagents could be transversely electrophoresed, magnetically transferred, or otherwise transported to a new substrate in their retained positional pattern.

III. Polynucleotide Sequencing

In principle, the making of a substrate having a positionally defined matrix pattern of all possible oligonucleotides of a given length involves a conceptually simple method of synthesizing each and every different possible oligonucleotide, and affixing them to a definable position. Oligonucleotide synthesis is presently mechanized and enabled by current technology, see, e.g., Ser. No. 07/362,901, now abandoned; Pirrung et al. (1992) U.S. Pat. No. 5,143,854; and instruments supplied by Applied Biosystems, Foster City, Calif.

A. Preparation of Substrate Matrix

The production of the collection of specific oligonucleotides used in polynucleotide sequencing may be produced in at least two different ways. Present technology certainly allows production of ten nucleotide oligomers on a solid phase or other synthesizing system. See, e.g., instrumentation provided by Applied Biosystems, Foster City, Calif. Although a single oligonucleotide can be relatively easily made, a large collection of them would typically require a fairly large amount of time and investment. For example, there are $4^{10}$=1,048,576 possible ten nucleotide oligomers. Present technology allows making each and every one of them in a separate purified form though such might be costly and laborious.

Once the desired repertoire of possible oligomer sequences of a given length have been synthesized, this collection of reagents may be individually positionally attached to a substrate, thereby allowing a batchwise hybridization step. Present technology also would allow the possibility of attaching each and every one of these 10-mers to a separate specific position on a solid matrix. This attachment could be automated in any of a number of ways, particularly through the use of a caged biotin type linking. This would produce a matrix having each of different possible 10-mers.

A batchwise hybridization is much preferred because of its reproducibility and simplicity. An automated process of attaching various reagents to positionally defined sites on a substrate is provided in Pirrung et al. (1992) U.S. Pat. No. 5,143,854; Ser. No. 07/624,120, now abandoned; and Barrett et al. (1993) U.S. Pat. No. 5,252,743; each of which is hereby incorporated herein by reference.

Instead of separate synthesis of each oligonucleotide, these oligonucleotides are conveniently synthesized in parallel by sequential synthetic processes on a defined matrix pattern as provided in Pirrung et al. (1992) U.S. Pat. No. 5,143,854; and Ser. No. 07/624,120, now abandoned, which are incorporated herein by reference. Here, the oligonucleotides are synthesized stepwise on a substrate at positionally separate and defined positions. Use of photosensitive blocking reagents allows for defined sequences of synthetic steps over the surface of a matrix pattern. By use of the binary masking strategy, the surface of the substrate can be positioned to generate a desired pattern of regions, each having a defined sequence oligonucleotide synthesized and immobilized thereto.

Although the prior art technology can be used to generate the desired repertoire of oligonucleotide probes, an efficient and cost effective means would be to use the VLSIPS technology described in Pirrung et al. (1992) U.S. Pat. No. 5,143,854 and Ser. No. 07/624,120, now abandoned. In this embodiment, the photosensitive reagents involved in the production of such a matrix are described below.

The regions for synthesis may be very small, usually less than about 100 $\mu$m×100 $\mu$m, more usually less than about 50 $\mu$m×50 $\mu$m. The photolithography technology allows synthetic regions of less than about 10 $\mu$m×10 $\mu$m, about 3 $\mu$m×3 $\mu$m, or less. The detection also may detect such sized regions, though larger areas are more easily and reliably measured.

At a size of about 30 microns by 30 microns, one million regions would take about 11 centimeters square or a single wafer of about 4 centimeters by 4 centimeters. Thus the present technology provides for making a single matrix of that size having all one million plus possible oligonucleotides. Region size is sufficiently small to correspond to densities of at least about 5 regions/cm$^2$, 20 regions/cm$^2$, 50 regions/cm$^2$, 100 regions/cm$^2$, and greater, including 300. regions/cm$^2$, 1000 regions/cm$^2$, 3K regions/cm$^2$, 10K regions/cm$^2$, 30K regions/cm$^2$, 100K regions/cm$^2$, 300K regions/cm$^2$ or more, even in excess of one million regions/cm$^2$.

Although the pattern of the regions which contain specific sequences is theoretically not important, for practical reasons certain patterns will be preferred in synthesizing the oligonucleotides. The application of binary masking algorithms for generating the pattern of known oligonucleotide probes is described in related Ser. No. 07/624,120, now abandoned, which was filed simultaneously with this application. By use of these binary masks, a highly efficient means is provided for producing the substrate with the desired matrix pattern of different sequences. Although the binary masking strategy allows for the synthesis of all lengths of polymers, the strategy may be easily modified to provide only polymers of a given length. This is achieved by omitting steps where a subunit is not attached.

The strategy for generating a specific pattern may take any of a number of different approaches. These approaches are well described in related application Ser. No. 07/624,120, now abandoned, and include a number of binary masking approaches which will not be exhaustively discussed herein. However, the binary masking and binary synthesis approaches provide a maximum of diversity with a minimum number of actual synthetic steps.

The length of oligonucleotides used in sequencing applications will be selected on criteria determined to some extent by the practical limits discussed above. For example, if probes are made as oligonucleotides, there will be 65,536 possible eight nucleotide sequences. If a nine subunit oligonucleotide is selected, there are 262,144 possible permeations of sequences. If a ten-mer oligonucleotide is selected, there are 1,048,576 possible permeations of sequences. As the number gets larger, the required number of positionally defined subunits necessary to saturate the possibilities also increases. With respect to hybridization conditions, the length of the matching necessary to confer stability of the conditions selected can be compensated for. See, e.g., Kanehisa, M. (1984) *Nuc. Acids Res.* 12:203–213, which is hereby incorporated herein by reference.

Although not described in detail here, but below for oligonucleotide probes, the VLSIPS technology would typically use a photosensitive protective group on an oligonucleotide. Sample oligonucleotides are shown in FIG. 1. In particular, the photoprotective group on the nucleotide molecules may be selected from a wide variety of positive light reactive groups preferably including nitro aromatic compounds such as o-nitro-benzyl derivatives or benzylsulfonyl.

See, e.g., Gait (1984) *Oligonucleotide Synthesis: A Practical Approach*, IRL Press, Oxford, which is hereby incorporated herein by reference. In a preferred embodiment, 6-nitroveratryl oxycarbony (NVOC), 2-nitrobenzyl oxycarbonyl (NBOC), or α,α-dimethyl-dimethoxybenzyl oxycarbonyl (DEZ) is used. Photoremovable protective groups are described in, e.g., Patchornik (1970) *J. Amer. Chem. Soc.* 92:6333–6335; and Amit et al. (1974) *J. Organic Chem.* 39:192–196; each of which is hereby incorporated herein by reference.

A preferred linker for attaching the oligonucleotide to a silicon matrix is illustrated in FIG. 2. A more detailed description is provided below. A photosensitive blocked nucleotide may be attached to specific locations of unblocked prior cycles of attachments on the substrate and can be successively built up to the correct length oligonucleotide probe.

It should be noted that multiple substrates may be simultaneously exposed to a single target sequence where each substrate is a duplicate of one another or where, in combination, multiple substrates together provide the complete or desired subset of possible subsequences. This provides the opportunity to overcome a limitation of the density of positions on a single substrate by using multiple substrates. In the extreme case, each probe might be attached to a single bead or substrate and the beads sorted by whether there is a binding interaction. Those beads which do bind might be encoded to indicate the subsequence specificity of reagents attached thereto.

Then, the target may be bound to the whole collection of beads and those beads that have appropriate specific reagents on them will bind to the target. Then a sorting system may be utilized to sort those beads that actually bind the target from those that do not. This may be accomplished by presently available cell sorting devices or a similar apparatus. After the relatively small number of beads which have bound the target have been collected, the encoding scheme may be read off to determine the specificity of the reagent on the bead. An encoding system may include a magnetic system, a shape encoding system, a color encoding system, or a combination of any of these, or any other encoding system. Once again, with the collection of specific interactions that have occurred, the binding may be analyzed for sequence information, fingerprint information, or mapping information.

The parameters of polynucleotide sizes of both the probes and target sequences are determined by the applications and other circumstances. The length of the oligonucleotide probes used will depend in part upon the limitations of the VLSIPS technology to provide the number of desired probes. For example, in an absolute sequencing application, it is often useful to have virtually all of the possible oligonucleotides of a given length. As indicated above, there are 65,536 8-mers, 262,144 9-mers, 1,048,576 10-mers, 4,194,304 11-mers, etc. As the length of the oligomer increases the number of different probes which must be synthesized also increases at a rate of a factor of 4 for every additional nucleotide. Eventually the size of the matrix and the limitations in the resolution of regions in the matrix will reach the point where an increase in number of probes becomes disadvantageous. However, this sequencing procedure requires that the system be able to distinguish, by appropriate selection of hybridization and washing conditions, between binding of absolute fidelity and binding of complementary sequences containing mismatches. On the other hand, if the fidelity is unnecessary, this discrimination is also unnecessary and a significantly longer probe may be used. Significantly longer probes would typically be useful in fingerprinting or mapping applications.

The length of the probe is selected for a length that will allow the probe to bind with specificity to possible targets. The hybridization conditions are also very important in that they will determine how closely the homology of complementary binding will be detected. In fact, a single target may be evaluated at a number of different conditions to determine its spectrum of specificity for binding particular probes. This may find use in a number of other applications besides the polynucleotide sequencing fingerprinting or mapping. For example, it will be desired to determine the spectrum of binding affinities and specificities of cell surface antigens with binding by particular antibodies immobilized on the substrate surface, particularly under different interaction conditions. In a related fashion, different regions with reagents having differing affinities or levels of specificity may allow such a spectrum to be defined using a single incubation, where various regions, at a given hybridization condition, show the binding affinity. For example, fingerprint probes of various lengths, or with specific defined non-matches may be used. Unnatural nucleotides or nucleotides exhibiting modified specificity of complementary binding are described in greater detail in Macevicz (1990) PCT pub. No. WO 90/04652; and see the section on modified nucleotides in the Sigma Chemical Company catalogue.

B. Labeling Target Nucleotide

The label used to detect the target sequences will be determined, in part, by the detection methods being applied. Thus, the labeling method and label used are selected in combination with the actual detecting systems being used.

Once a particular label has been selected, appropriate labeling protocols will be applied, as described below for specific embodiments. Standard labeling protocols for nucleic acids are described, e.g., in Sambrook et al.; Kambara, H. et al. (1988) *BioTechnology* 6:816–821; Smith, L. et al. (1985) *Nuc. Acids Res.* 13:2399–2412; for polypeptides, see, e.g., Allen G. (1989) *Sequencing of Proteins and Peptides*, Elsevier, New York, especially chapter 5, and Greenstein and Winitz (1961) *Chemistry of the Amino Acids*, Wiley and Sons, New York. Carbohydrate labeling is described, e.g., in Chaplin and Kennedy (1986) *Carbohydrate Analysis: A Practical Approach*, IRL Press, Oxford. Labeling of other polymers will be performed by methods applicable to them as recognized by a person having ordinary skill in manipulating the corresponding polymer.

In some embodiments, the target need not actually be labeled if a means for detecting where interaction takes place is available. As described below, for a nucleic acid embodiment, such may be provided by an intercalating dye which intercalates only into double stranded segments, e.g., where interaction occurs. See, e.g., Sheldon et al. U.S. Pat. No. 4,582,789.

In many uses, the target sequence will be absolutely homogeneous, both with respect to the total sequence and with respect to the ends of each molecule. Homogeneity with respect to sequence is important to avoid ambiguity. It is preferable that the target sequences of interest not be contaminated with a significant amount of labeled contaminating sequences. The extent of allowable contamination will depend on the sensitivity of the detection system and the inherent signal to noise of the system. Homogeneous contamination sequences will be particularly disruptive of the sequencing procedure.

However, although the target polynucleotide must have a unique sequence, the target molecules need not have identical ends. In fact, the homogeneous target molecule preparation may be randomly sheared to increase the numerical number of molecules. Since the total information content remains the same, the shearing results only in a higher number of distinct sequences which may be labeled and bind to the probe. This fragmentation may give a vastly superior signal relative to a preparation of the target molecules having homogeneous ends. The signal for the hybridization is likely to be dependent on the numerical frequency of the target-probe interactions. If a sequence is individually found on a larger number of separate molecules a better signal will result. In fact, shearing a homogeneous preparation of the target may often be preferred before the labeling procedure is performed, thereby producing a large number of labeling groups associated with each subsequence.

C. Hybridization Conditions

The hybridization conditions between probe and target should be selected such that the specific recognition interaction, i.e., hybridization, of the two molecules is both sufficiently specific and sufficiently stable. See, e.g., Hames and Higgins (1985) *Nucleic Acid Hybridisation: A Practical Approach*, IRL Press, Oxford. These conditions will be dependent both on the specific sequence and often on the guanine and cytosine (GC) content of the complementary hybrid strands. The conditions may often be selected to be universally equally stable independent of the specific sequences involved. This typically will make use of a reagent such as an alkylammonium buffer. See, Wood et al. (1985) "Base Composition-independent Hybridization in Tetramethylammonium Chloride: A Method for Oligonucleotide Screening of Highly Complex Gene Libraries," *Proc. Natl. Acad. Sci. USA*, 82:1585–1588; and Krupov et al. (1989) "An Oligonucleotide Hybridization Approach to DNA Sequencing," *FEBS Letters*, 256:118–122; each of which is hereby incorporated herein by reference. An alkylammonium buffer tends to minimize differences in hybridization rate and stability due to GC content. By virtue of the fact that sequences then hybridize with approximately equal affinity and stability, there is relatively little bias in strength or kinetics of binding for particular sequences. Temperature and salt conditions along with other buffer parameters should be selected such that the kinetics of renaturation should be essentially independent of the specific target subsequence or oligonucleotide probe involved. In order to ensure this, the hybridization reactions will usually be performed in a single incubation of all the substrate matrices together exposed to the identical same target probe solution under the same conditions.

Alternatively, various substrates may be individually treated differently. Different substrates may be produced, each having reagents which bind to target subsequences with substantially identical stabilities and kinetics of hybridization. For example, all of the high GC content probes could be synthesized on a single substrate which is treated accordingly. In this embodiment, the arylammonium buffers could be unnecessary. Each substrate is then treated in a manner such that the collection of substrates show essentially uniform binding and the hybridization data of target binding to the individual substrate matrix is combined with the data from other substrates to derive the necessary subsequence binding information. The hybridization conditions will usually be selected to be sufficiently specific such that the fidelity of base matching will be properly discriminated. Of course, control hybridizations should be included to determine the stringency and kinetics of hybridization.

D. Detection; VLSIPS™ Technolonogy Scanning

The next step of the sequencing process by hybridization involves labeling of target polynucleotide molecules. A quickly and easily detectable signal is preferred. The VLSIPS™ Technology apparatus is designed to easily detect a fluorescent label, so fluorescent tagging of the target sequence is preferred. Other suitable labels include heavy metal labels, magnetic probes, chromogenic labels (e.g., phosphorescent labels, dyes, and fluorophores) spectroscopic labels, enzyme linked labels, radioactive labels, and labeled binding proteins. Additional labels are described in U.S. Pat. No. 4,366,241, which is incorporated herein by reference.

The detection methods used to determine where hybridization has taken place will typically depend upon the label selected above. Thus, for a fluorescent label a fluorescent detection step will typically be used. Pirrung et al. (1992) U.S. Pat. No. 5,143,854 and Ser. No. 07/624,120, now abandoned, describe apparatus and mechanisms for scanning a substrate matrix using fluorescence detection, but a similar apparatus is adaptable for other optically detectable labels.

The detection method provides a positional localization of the region where hybridization has taken place. However, the position is correlated with the specific sequence of the probe since the probe has specifically been attached or synthesized at a defined substrate matrix position. Having collected all of the data indicating the subsequences present in the target sequence, this data may be aligned by-overlap to reconstruct the entire sequence of the target, as illustrated above.

It is also possible to dispense with actual labeling if some means for detecting the positions of interaction between the sequence specific reagent and the target molecule are available. This may take the form of an additional reagent which can indicate the sites either of interaction, or the sites of lack of interaction, e.g., a negative label. For the nucleic acid embodiments, locations of double strand interaction may be detected by the incorporation of intercalating dyes, or other reagents such as antibody or other reagents that recognize helix formation, see, e.g., Sheldon, et al. (1986) U.S. Pat. No. 4,582,789, which is hereby incorporated herein by reference.

E. Analysis

Although the reconstruction can be performed manually as illustrated above, a computer program will typically be used to perform the overlap analysis. A program may be written and run on any of a large number of different computer hardware systems. The variety of operating systems and languages useable will be recognized by a computer software engineer. Various different languages may be used, e.g., BASIC; C; PASCAL; etc. A simple flow chart of data analysis is illustrated in FIG. 1.

F. Substrate Reuse

Finally, after a particular sequence has been hybridized and the pattern of hybridization analyzed, the matrix substrate should be reusable and readily prepared for exposure to a second or subsequent target polynucleotides. In order to do so, the hybrid duplexes are disrupted and the matrix treated in a way which removes all traces of the original target. The matrix may be treated with various detergents or solvents to which the substrate, the oligonucleotide probes, and the linkages to the substrate are inert. This treatment may include an elevated temperature treatment, treatment with organic or inorganic solvents, modifications in pH, and other means for disrupting specific interaction. Thereafter, a second target may actually be applied to the recycled matrix and analyzed as before.

G. Non-Polynucleotide Aspects

Although the sequencing, fingerprinting, and mapping functions will make use of the natural sequence recognition property of complementary nucleotide sequences, the non-polynucleotide sequences typically require other sequence recognition reagents. These reagents will take the form, typically, of proteins exhibiting binding specificity, e.g., enzyme binding sites or antibody binding sites.

Enzyme binding sites may be derived from promoter proteins, restriction enzymes, and the like. See, e.g., Stryer, L. (1988) *Biochemistry*, W. H. Freeman, Palo Alto. Antibodies will typically be produced using standard procedures, see, e.g., Harlow and Lane (1988) *Antibodies: A Laboratory Manual*, Cold Spring Harbor Press, New York; and Goding (1986) *Monoclonal Antibodies: Principles and Practice*, (2d Ed.) Academic Press, San Diego.

Typically, an antigen, or collection of antigens are presented to an immune system. This may take the form of synthesized short polymers produced by the VLSIPS technology, or by the other synthetic means, or from isolation of natural products. For example, antigen for the polypeptides may be made by the VLSIPS technology, by standard peptide synthesis, by isolation of natural proteins with or without degradation to shorter segments, or by expression of a collection of short nucleic acids of random or defined sequences. See, e.g., Tuerk and Gold (1990) *Science* 249:505–510, for generation of a collection of randomly mutagenized oligonucleotides useful for expression.

The antigen or collection is presented to an appropriate immune system, e.g., to a whole animal as in a standard immunization protocol, or to a collection of immune cells or equivalent. In particular, see Ward et al. (1989) *Nature* 341:544–546; and Huse et al. (1989) *Science* 246:1275–1281, each of which is hereby incorporated herein by reference.

A large diversity of antibodies will be generated, some of which have specificities for the desired sequences. Antibodies may be purified having the desired sequence specificities by isolating the cells producing them. For example, a VLSIPS substrate with the desired antigens synthesized thereon may be used to isolate cells with cell surface reagents which recognize the antigens. The VLSIPS substrate may be used as an affinity reagent to select and recover the appropriate cells. Antibodies from those cells may be attached to a substrate using the caged biotin methodology, or by attaching a targeting molecule, e.g., an oligonucleotide. Alternatively, the supernatants from antibody producing cells can be easily assayed using a VLSIPS substrate to identify the cells producing the appropriate antibodies.

Although cells may be isolated, specific antibody molecules which perform the sequence recognition will also be sufficient. Preferably populations of antibody with a known specificity can be isolated. Supernatants from a large population of producing cells may be passed over a VLSIPS substrate to bind to the desired antigens attached to the substrate. When a sufficient density of antibody molecules are attached, they may be removed by an automated process, preferably as antibody populations exhibiting specificity of binding.

In one particular embodiment, a VLSIPS substrate, e.g., with a large plurality of fingerprint antigens attached thereto, is used to isolate antibodies from a supernatant of a population of cells producing antibodies to the antigens. Using the substrate as an affinity reagent, the antibodies will attach to the appropriate positionally defined antigens. The antibodies may be carefully removed therefrom, preferably by an automated system which retains their homogeneous specificities. The isolated antibodies can be attached to a new substrate in a positionally defined matrix pattern.

In a further embodiment, these spatially separated antibodies may be isolated using a specific targeting method for isolation. In this embodiment, a linker molecule which attaches to a particular portion of the antibody, preferably away from the binding site, can be attached to the antibodies. Various reagents will be used, including staphylococcus protein A or antibodies which bind to domains remote from the binding site. Alternatively, the antibodies in the population, before affinity purification, may be derivatized with an appropriate reagent compatible with new VLSIPS synthesis. A preferred reagent is a nucleotide which can serve as a linker to synthetic VLSIPS steps for synthesizing a specific sequence thereon. Then, by successive VLSIPS cycles, each of the antibodies attached to the defined antigen regions can have a defined oligonucleotide synthesized thereon and corresponding in area to the region of the substrate having each antigen attached. These defined oligonucleotides will be useful as targeting reagents to attach those antibodies possessing the same target sequence specificity at defined positions on a new substrate, by virtue of having bound to the antigen region, to a new VLSIPS substrate having the complementary target oligonucleotides positionally located on it. In this fashion, a VLSIPS substrate having the desired antigens attached thereto can be used to generate a second VLSIPS substrate with positionally defined reagents which recognize those antigens.

The selected antigens will typically be selected to be those which define particular functionalities or properties, so as to be useful for fingerprinting and other uses. They will also be useful for mapping and sequencing embodiments.

IV. Fingerprinting

A. General

Many of the procedures and techniques used in the polynucleotide sequencing section are also appropriate for fingerprinting applications. See, e.g., Poustka, et al. (1986) *Cold Spring Harbor Symposia on Ouant. Biol.*, vol. LI, 131–139, Cold Spring Harbor Press, New York; which is hereby incorporated herein by reference. The fingerprinting method provided herein is based, in part, upon the ability to positionally localize a large number of different specific probes onto a single substrate. This high density matrix pattern provides the ability to screen for, or detect, a very large number of different sequences simultaneously. In fact, depending upon the hybridization conditions, fingerprinting to the resolution of virtually absolute matching of sequence is possible thereby approaching an absolute sequencing embodiment. And the sequencing embodiment is very useful in identifying the probes useful in further fingerprinting uses. For example, characteristic features of genetic sequences will be identified as being diagnostic of the entire sequence. However, in most embodiments, longer probe and target will be used, and for which slight mismatching may not need to be resolved.

B. Preparation of Substrate Matrix

A collection of specific probes may be produced by either of the methods described above in the section on sequencing. Specific oligonucleotide probes of desired lengths may be individually synthesized on a standard oligonucleotide synthesizer. The length of these probes is limited only by the ability of the synthesizer to continue to accurately synthesize a molecule. Oligonucleotides or sequence fragments may also be isolated from natural sources. Biological amplification methods may be coupled with synthetic synthesizing procedures such as, e.g., polymerase chain reaction.

In one embodiment, the individually isolated probes may be attached to the matrix at defined positions. These probe reagents may be attached by an automated process making use of the caged biotin methodology described in Ser. No. 07/612,671, or using photochemical reagents, see, e.g., Dattagupta et al. (1985) U.S. Pat. No. 4,542,102 and (1987) U.S. Pat. No. 4,713,326. Each individually purified reagent can be attached individually at specific locations on a substrate.

In another embodiment, the VLSIPS synthesizing technique may be used to synthesize the desired probes at specific positions on a substrate. The probes may be synthesized by successively adding appropriate monomer subunits, e.g., nucleotides, to generate the desired sequences.

In another embodiment, a relatively short specific oligonucleotide is used which serves as a targeting-reagent for positionally directing the sequence recognition reagent. For example, the sequence specific reagents having a separate additional sequence recognition segment (usually of a different polymer from the target sequence) can be directed to target oligonucleotides attached to the substrate. By use of non-natural targeting reagents, e.g., unusual nucleotide analogues which pair with other unnatural nucleotide analogues and which do not interfere with natural nucleotide interactions, the natural and non-natural portions can coexist on the same molecule without interfering with their individual functionalities. This can combine both a synthetic and biological production system analogous to the technique for targeting monoclonal antibodies to locations on a VLSIPS substrate at defined positions. Unnatural optical isomers of nucleotides may be useful unnatural reagents subject to similar chemistry, but incapable of interfering with the natural biological polymers. See also, Ser. No. 07/626,730, which is hereby incorporated herein by reference.

After the separate substrate attached reagents are attached to the targeting segment, the two are crosslinked, thereby permanently attaching them to the substrate. Suitable crosslinking reagents are known, see, e.g., Dattagupta et al. (1985) U.S. Pat. No. 4,542,102 and (1987) "Coupling of nucleic acids to solid support by photochemical methods," U.S. Pat. No. 4,713,326, each of which is hereby incorporated herein by reference. Similar linkages for attachment of proteins to a solid substrate are provided, e.g., in Merrifield (1986) *Science* 232:341–347, which is hereby incorporated herein by reference.

C. Labeling Target Nucleotides

The labeling procedures used in the sequencing embodiments will also be applicable in the fingerprinting embodiments. However, since the fingerprinting embodiments often will involve relatively large target molecules and relatively short oligonucleotide probes, the amount of signal necessary to incorporate into the target sequence may be less critical than in the sequencing applications. For example, a relatively long target with a relatively small number of labels per molecule may be easily amplified or detected because of the relatively large target molecule size.

In various embodiments, it may be desired to cleave the target into smaller segments as in the sequencing embodiments. The labeling procedures and cleavage techniques described in the sequencing embodiments would usually also be applicable here.

D. Hybridization Conditions

The hybridization conditions used in fingerprinting embodiments will typically be less critical than for the sequencing embodiments. The reason is that the amount of mismatching which may be useful in providing the fingerprinting information would typically be far greater than that necessary in sequencing uses. For example, Southern hybridizations do not typically distinguish between slightly mismatched sequences. Under these circumstances, important and valuable information may be arrived at with less stringent hybridization conditions while providing valuable fingerprinting information. However, since the entire substrate is typically exposed to the target molecule at one time, the binding affinity of the probes should usually be of approximately comparable levels. For this reason, if oligonucleotide probes are being used, their lengths should be approximately comparable and will be selected to hybridize under conditions which are common for most of the probes on the substrate. Much as in a Southern hybridization, the target and oligonucleotide probes are of lengths typically greater than about 25 nucleotides. Under appropriate hybridization conditions, e.g., typically higher salt and lower temperature, the probes will hybridize irrespective of imperfect complementarity. In fact, with probes of greater than, e.g., about fifty nucleotides, the difference in stability of different sized probes will be relatively minor.

Typically the fingerprinting is merely for probing similarity or homology. Thus, the stringency of hybridization can usually be decreased to fairly low levels. See, e.g., Wetmur and Davidson (1968) "Kinetics of Renaturation of DNA," *J. Mol. Biol.*, 31:349–370; and Kanehisa, M. (1984) *Nuc. Acids Res.*, 12:203–213.

E. Detection; VLSIPS™ Technology Scanning

Detection methods will be selected which are appropriate for the selected label. The scanning device need not necessarily be digitized or placed into a specific digital database, though such would most likely be done. For example, the analysis in fingerprinting could be photographic. Where a standardized fingerprint substrate matrix is used, the pattern of hybridizations may be spatially unique and may be compared photographically. In this manner, each sample may have a characteristic pattern of interactions and the likelihood of identical patterns will preferably be such low frequency that the fingerprint pattern indeed becomes a characteristic pattern virtually as unique as an individual's fingertip fingerprint. With a standardized substrate, every individual could be, in theory, uniquely identifiable on the basis of the pattern of hybridizing to the substrate.

Of course, the VLSIPS™ Technology scanning apparatus may also be useful to generate a digitized version of the fingerprint pattern. In this way, the identification pattern can be provided in a linear string of digits. This sequence could also be used for a standardized identification system providing significant useful medical transferability of specific data. In one embodiment, the probes used are selected to be of sufficiently high resolution to measure the antigens of the major histo compatibility complex. It might even be possible to provide transplantation matching data in a linear stream of data. The fingerprinting data may provide a condensed version, or summary, of the linear genetic data, or any other information data base.

F. Analysis

The analysis of the fingerprint will often be much simpler than a total sequence determination. However, there may be particular types of analysis which will be substantially simplified by a selected group of probes. For example, probes which exhibit particular populational heterogeneity may be selected. In this way, analysis may be simplified and practical utility enhanced merely by careful selection of the specific probes and a careful matrix layout of those probes.

G. Substrate Reuse

As with the sequencing application, the fingerprinting usages may also take advantage of the reusability of the substrate. In this way, the interactions can be disrupted, the substrate treated, and the renewed substrate is equivalent to an unused substrate.

H. Non-polynucleotide Aspects

Besides polynucleotide applications, the fingerprinting analysis may be applied to other polymers, especially polypeptides, carbohydrates, and other polymers, both organic and inorganic. Besides using the fingerprinting method for analyzing a particular polymer, the fingerprinting method may be used to characterize various samples. For example, a cell or population of cells may be tested for their expression of specific antigens or their mRNA sequence intent. For example, a T-cell may be classified by virtue of its combination of expressed surface antigens. With specific reagents which interact with these antigens, a cell or a population of cells or a lysed cell may be exposed to a VLSIPS substrate. The biological sample may be classified or characterized by analyzing the pattern of specific interaction. This may be applicable to a cell or tissue type, to the messenger RNA population expressed by a cell to the genetic content of a cell, or to virtually any sample which can be classified and/or identified by its combination of specific molecular properties.

The ability to generate a high density means for screening the presence or absence of specific interactions allows for the possibility of screening for, if not saturating, all of a very large number of possible interactions. This is very powerful in providing the means for testing the combinations of molecular properties which can define a class of samples. For example, a species of organism may be characterized by its DNA sequences, e.g., a genetic fingerprint. By using a fingerprinting method, it may be determined that all members of that species are sufficiently similar in specific sequences that they can be easily identified as being within a particular group. Thus, newly defined classes may be resolved by their similarity in fingerprint patterns. Alternatively, a non-member of that group will fail to share those many identifying characteristics. However, since the technology allows testing of a very large number of specific interactions, it also provides the ability to more finely distinguish between closely related different cells or samples. This will have important applications in diagnosing viral, bacterial, and other pathological on nonpathological infections.

In particular, cell classification may be defined by any of a number of different properties. For example, a cell class may be defined by its DNA sequences contained therein. This allows species identification for parasitic or other infections. For example, the human cell is presumably genetically distinguishable from a monkey cell, but different human cells will share many genetic markers. At higher resolution, each individual human genome will exhibit unique sequences that can define it as a single individual.

Likewise, a developmental stage of a cell type may be definable by its pattern of expression of messenger RNA. For example, in particular stages of cells, high levels of ribosomal RNA are found whereas relatively low levels of other types of messenger RNAs may be found. The high resolution distinguishability provided by this fingerprinting method allows the distinction between cells which have relatively minor differences in its expressed mRNA population. Where a pattern is shown to be characteristic of a stage, a stage may be defined by that particular pattern of messenger RNA expression.

In a similar manner, the antigenic determinants found on a protein may very well define the cell class. For example, immunological T-cells are distinguishable from B-cells because, in part, the cell surface antigens on the cell types are distinguishable. Different T-cell subclasses can be also distinguished from one another by whether they contain particular T-cell antigens. The present invention provides the possibility for high resolution testing of many different interactions simultaneously, and the definition of new cell types will be possible.

The high resolution VLSIPS™ substrate may also be used as a very powerful diagnostic tool to test the combination of presence, of a plurality of different assays from a biological sample. For example, a cancerous condition may be indicated by a combination of various different properties found in the blood. For example, a cancerous condition may be indicated by a combination of expression of various soluble antigens found in the blood along with a high number of various cellular antigens found on lymphocytes and/or particular cell degradation products. With a substrate as provided herein, a large number of different features can be simultaneously performed on a biological sample. In fact, the high resolution of the test will allow more complete characterization of parameters which define particular diseases. Thus, the power of diagnostic tests may be limited by the extent of statistical correlation with a particular condition rather than with the number of antigens or interactions which are tested. The present invention provides the means to generate this large universe of possible reagents and the ability to actually accumulate that correlative data.

In another embodiment, a substrate as provided herein may be used for genetic screening. This would allow for simultaneous screening of thousands of genetic markers. As the density of the matrix is increased, many more molecules can be simultaneously tested. Genetic screening then becomes a simpler method as the present invention provides the ability to screen for thousands, tens of thousands, and hundreds of thousands, even millions of different possible genetic features. However, the number of high correlation genetic markers for conditions numbers only in the hundreds. Again, the possibility for screening a large number of sequences provides the opportunity for generating the data which can provide correlation between sequences and specific conditions or susceptibility. The present invention provides the means to generate extremely valuable correlations useful for the genetic detection of the causative mutation leading to medical conditions. In still another embodiment, the present invention would be applicable to distinguishing two individuals having identical genetic compositions. The antibody population within an individual is dependent both on genetic and historical factors. Each individual experiences a unique exposure to various infectious agents, and the combined antibody expression is partly determined thereby. Thus, individuals may also be fingerprinted by their immunological content, either of actively expressed antibodies, or their immunological memory. Similar sorts of immunological and environmental histories may be useful for fingerprinting, perhaps in combination with other screening properties. In particular, the present invention may be useful for screening allergic reactions or susceptibilities, and a simple IgE specificity test may be useful in determining a spectrum of allergies.

With the definition of new classes of cells, a cell sorter will be used to purify them. Moreover, new markers for defining that class of cells will be identified. For example, where the class is defined by its RNA content, cells may be screened by antisense probes which detect the presence or absence of specific sequences therein. Alternatively, cell lysates may provide information useful in correlating intracellular properties with extracellular markers which indicate functional differences. Using standard cell sorter technology with a fluorescence or labeled antisense probe which recognizes the internal presence of the specific sequences of interest, the cell sorter will be able to isolate a relatively homogeneous population of cells possessing the particular marker. Using successive probes the sorting process should be able to select for cells having a combination of a large number of different markers.

In a non-polynucleotide embodiment, cells may be defined by the presence of other markers. The markers may be carbohydrates, proteins, or other molecules. Thus, a substrate having particular specific reagents, e.g., antibodies, attached to it should be able to identify cells having particular patterns of marker expression. Of course, combinations of these made be utilized and a cell class may be defined by a combination of its expressed mRNA, its carbohydrate expression, its antigens, and other properties. This fingerprinting should be useful in determining the physiological state of a cell or population of cells.

Having defined a cell type whose function or properties are defined by the reagents attachable to a VLSIPS substrate, such as cellular antigens, these structural manifestations of function may be used to sort cells to generate a relatively homogeneous population of that class of cells. Standard cell sorter technology may be applied to purify such a population, see, e.g., Dangl, J. and Herzenberg (1982) "Selection of hybridomas and hybridoma variants using the fluorescence activated cell sorter," *J. Immunological Methods* 52:1–14; and Becton Dickinson, Fluorescence Activated Cell Sorter Division, San Jose, Calif., and Coulter Diagnostics, Hialeah, Fla.

With the fingerprinting method an identification means arises from mosaicism problems in an organism. A mosaic organism is one whose genetic content in different cells is significantly different. Various clonal populations should have similar genetic fingerprints, though different clonal populations may have different genetic contents. See, for example, Suzuki et al. *An Introduction to Genetic Analysis* (4th Ed.), Freeman and Co., New York, which is hereby incorporated herein by reference. However, this problem should be a relatively rare problem and could be more carefully evaluated with greater experience using the fingerprinting methods.

The invention will also find use in detecting changes, both genetic and antigenic, e.g., in a rapidly "evolving" protozoa infection, or similarly changing organism.

V. Mapping

A. General

The use of the present invention for mapping parallels its use for fingerprinting and sequencing. Where a polymer is a linear molecule, the mapping provides the ability to locate particular segments along the length of the polymer. Branched polymers can be treated as a series of individual linear polymers. The mapping provides the ability to locate, in a relative sense, the order of various subsequences. This may be achieved using at least two different approaches.

The first approach is to take the large sequence and fragment it at specific points. The fragments are then ordered and attached to a solid substrate. For example, the clones resulting from a chromosome walking process may be individually attached to the substrate by methods, e.g., caged biotin techniques, indicated earlier. Segments of unknown map position will be exposed to the substrate and will hybridize to the segment which contains that particular sequence. This procedure allows the rapid determination of a number of different labeled segments, each mapping requiring only a single hybridization step once the substrate is generated. The substrate may be regenerated by removal of the interaction, and the next mapping segment applied.

In an alternative method, a plurality of subsequences can be attached to a substrate. Various short probes may be applied to determine which segments may contain particular overlaps. The theoretical basis and a description of this mapping procedure is contained in, e.g., Evans et al. 1989 "Physical Mapping of Complex Genomes by Cosmid Multiplex Analysis," *Proc. Natl. Acad. Sci. USA* 86:5030–5034, and other references cited above in the Section labeled "Overall Description." Using this approach, the details of the mapping embodiment are very similar to those used in the fingerprinting embodiment.

B. Preparation of Substrate Matrix

The substrate may be generated in either of the methods generally applicable in the sequencing and fingerprinting embodiments. The substrate may be made either synthetically, or by attaching otherwise purified probes or sequences to the matrix. The probes or sequences may be derived either from synthetic or biological means. As indicated above, the solid phase substrate synthetic methods may be utilized to generate a matrix with positionally defined sequences. In the mapping embodiment, the importance of saturation of all possible subsequences of a preselected length is far less important than in the sequencing embodiment, but the length of the probes used may be desired to be much longer. The processes for making a substrate which has longer oligonucleotide probes should not be significantly different from those described for the sequencing embodiments, but the optimization parameters may be modified to comply with the mapping needs.

C. Labeling

The labeling methods will be similar to those applicable in sequencing and fingerprinting embodiments. Again, it may be desirable to fragment the target sequences.

D. Hybridization/Specific Interaction

The specificity of interaction between the targets and probe would typically be closer to those used for fingerprinting embodiments, where homology is more important than absolute distinguishability of high fidelity complementary hybridization. Usually, the hybridization conditions will be such that merely homologous segments will interact and provide a positive signal. Much like the fingerprinting embodiment, it may be useful to measure the extent of homology by successive incubations at higher stringency conditions. Or, a plurality of different probes, each having various levels of homology may be used. In either way, the spectrum of homologies can be measured.

Where non-nucleic acid hybridization is involved, the specific interactions may also be compared in a fingerprint-like manner. The specific reagents may have less specificity, e.g., monoclonal antibodies which recognize a broader spectrum of sequences may be utilized relative to a sequencing embodiment. Again, the specificity of interaction may be measured under various conditions of increasing stringency to determine the spectrum of matching across the specific probes selected, or a number of different stringency reagents may be included to indicate the binding affinity.

E. Detection

The detection methods used in the mapping procedure will be virtually identical to those used in the fingerprinting embodiment. The detection methods will be selected in combination with the labeling methods.

F. Analysis

The analysis of the data in a mapping embodiment will typically be somewhat different from that in fingerprinting. The fingerprinting embodiment will test for the presence or absence of specific or homologous segments. However, in the mapping embodiment, the existence of an interaction is coupled with some indication of the location of the interaction. The interaction is mapped in some manner to the physical polymer sequence. Some means for determining the relative positions of different probes is performed. This may be achieved by synthesis of the substrate in pattern, or may result from analysis of sequences after they have been attached to the substrate.

For example, the probes may be randomly positioned at various locations on the substrate. However, the relative positions of the various reagents in the original polymer may be determined by using short fragments, e.g., individually, as target molecules which determine the proximity of different probes. By an automated system of testing each different short fragment of the original polymer, coupled with proper analysis, it will be possible to determine which probes are adjacent one another on the original target sequence and correlate that with positions on the matrix. In this way, the matrix is useful for determining the relative locations of various new segments in the original target molecule. This sort of analysis is described in Evans, and the related references described above.

G. Substrate Reuse

The substrate should be reusable in the manner described in the fingerprinting section. The substrate is renewed by removal of the specific interactions and is washed and prepared for successive cycles of exposure to new target sequences.

H. Non-polynucleotide Aspects

The mapping procedure may be used on other molecules than polynucleotides. Although hybridization is one type of specific interaction which is clearly useful for use in this mapping embodiment, antibody reagents may also be very useful. In the same way that polypeptide sequencing or other polymers may be sequenced by the reagents and techniques described in the sequencing section and fingerprinting section, the mapping embodiment may also be used similarly.

In another form of mapping, as described above in the fingerprinting section, the developmental map of a cell or biological system may be measured using fingerprinting type technology. Thus, the mapping may be along a temporal dimension rather than along a polymer dimension. The mapping or fingerprinting embodiments may also be used in determining the genetic rearrangements which may be genetically important, as in lymphocyte and B-cell development. In another example, various rearrangements or chromosomal dislocations may be tested by either the fingerprinting or mapping methods. These techniques are similar in many respects and the fingerprinting and mapping embodiments may overlap in many respects.

VI. Additional Screening and Applications

A. Specific Interactions

As originally indicated in the parent filing of VLSIPS™ Technology, the production of a high density plurality of spatially segregated polymers provides the ability to generate a very large universe or repertoire of individually and distinct sequence possibilities. As indicated above, particular oligonucleotides may be synthesized in automated fashion at specific locations on a matrix. In fact, these oligonucleotides may be used to direct other molecules to specific locations by linking specific oligonucleotides to other reagents which are in batch exposed to the matrix and hybridized in a complementary fashion to only those locations where the complementary oligonucleotide has been synthesized on the matrix. This allows for spatially attaching a plurality of different reagents onto the matrix instead of individually attaching each separate reagent at each specific location. Although the caged biotin method allows automated attachment, the speed of the caged biotin attachment process is relatively slow and requires a separate reaction for each reagent being attached. By use of the oligonucleotide method, the specificity of position can be done in an automated and parallel fashion. As each reagent is produced, instead of directly attaching each reagent at each desired position, the reagent may be attached to a specific desired complementary oligonucleotide which will ultimately be specifically directed toward locations on the matrix having a complementary oligonucleotide attached thereat.

In addition, the technology allows screening for specificity of interaction with particular reagents. For example, the oligonucleotide sequence specificity of binding of a potential reagent may be tested by presenting to the reagent all of the possible subsequences available for binding. Although secondary or higher order sequence specific features might not be easily screenable using this technology, it does provide a convenient, simple, quick, and thorough screen of interactions between a reagent and its target recognition sequences. See, e.g., Pfeifer et al. (1989) *Science* 246:810–812.

For example, the interaction of a promoter protein with its target binding sequence may be tested for many different, or all, possible binding sequences. By testing the strength of interactions under various different conditions, the interaction of the promoter protein with each of the different potential binding sites may be analyzed. The spectrum of strength of interactions with each different potential binding site may provide significant insight into the types of features which are important in determining specificity.

An additional example of a sequence specific interaction between reagents is the testing of binding of a double stranded nucleic acid structure with a single stranded oligonucleotide. Often, a triple stranded structure is produced which has significant aspects of sequence specificity. Testing of such interactions with either sequences comprising only natural nucleotides, or perhaps the testing of nucleotide analogs may be very important in screening for particularly useful diagnostic or therapeutic reagents. See, e.g., Häner and Dervan (1990) *Biochemistry* 29:9761–6765, and references therein.

B. Sequence Comparisons

Once a gene is sequenced, the present invention provides a means to compare alleles or related sequences to locate and identify differences from the control sequence. This would be extremely useful in further analysis of genetic variability at a specific gene locus.

C. Categorizations

As indicated above in the fingerprinting and mapping embodiments, the present invention is also useful in defining specific stages in the temporal sequence of cells, e.g., development, and the resulting tissues within an organism. For example, the developmental stage of a cell, or population of cells, can be dependent upon the expression of particular messenger RNAs or cellular antigens. The screening procedures provided allow for high resolution definition of new classes of cells. In addition, the temporal development of particular cells will be characterized by the presence or expression of various mRNAs. Means to simultaneously screen a plurality or very large number of different sequences are provided. The combination of different markers made available dramatically increases the ability to distinguish fairly closely related cell types. Other markers may be combined with markers and methods made available herein to define new classifications of biological samples, e.g., based upon new combinations of markers.

The presence or absence of particular marker sequences will be used to define temporal developmental stages. Once the stages are defined, fairly simple methods can be applied to actually purify those particular cells. For example, antisense probes or recognition reagents may be used with a cell sorter to select those cells containing or expressing the critical markers. Alternatively, the expression of those sequences may result in specific antigens which may also be used in defining cell classes and sorting those cells away from others. In this way, for example, it should be possible to select a class of omnipotent immune system cells which are able to completely regenerate a human immune system. Based upon the cellular classes defined by the parameters made available by this technology, purified classes of cells having identifiable differences, structural or functional, are made available.

In an alternative embodiment, a plurality of antigens or specific binding proteins attached to the substrate may be used to define particular cell types. For example, subclasses of T-cells are defined, in part, by the combination of expressed cell surface antigens. The present invention allows for the simultaneous screening of a large plurality of different antigens together. Thus, higher resolution classification of different T-cell subclasses becomes possible and, with the definitions and functional differences which correlate with those antigenic or other parameters, the ability to purify those cell types becomes available. This is applicable not only to T-cells, but also to lymphocyte cells, or even to freely circulating cells. Many of the cells for which this would be most useful will be immobile cells found in particular tissues or organs. Tumor cells will be diagnosed or detected using these fingerprinting techniques. Coupled with a temporal change in structure, developmental classes may also be selected and defined using these technologies. The present invention also provides the ability not only to define new classes of cells based upon functional or structural differences, but it also provides the ability to select or purify populations of cells which share these particular properties. Standard cell sorting procedures using antibody markers may be used to detect extracellular features. Intracellular features would also be detectable by introducing the label reagents into the cell. In particular, antisense DNA or RNA molecules may be introduced into a cell to detect RNA sequences therein. See, e.g., Weintraub (1990) *Scientific American* 262:40–46.

D. Statistical Correlations

In an additional embodiment, the present invention also allows for the high resolution correlation of medical conditions with various different markers. For example, the presently available technology, when applied to amniocentesis or other genetic screening methods, typically screens for tens of different markers at most. The present invention allows simultaneous screening for tens, hundreds, thousands, tens of thousands, hundreds of thousands, and even millions of different genetic sequences. Thus, applying the fingerprinting methods of the present invention to a sufficiently large population allows detailed statistical analysis to be made, thereby correlating particular medical conditions with particular markers, typically antigenic or genetic. Tumor specific antigens will be identified using the present invention.

Various medical conditions may be correlated against an enormous data base of the sequences within an individual. Genetic propensities and correlations then become available and high resolution genetic predictability and correlation become much more easily performed. With the enormous data base, the reliability of the predictions is also better tested. Particular markers which are partially diagnostic of particular medical conditions or medical susceptibilities will be identified and provide direction in further studies and more careful analysis of the markers involved. Of course, as indicated above in the sequencing embodiment, the present invention will find much use in intense sequencing projects. For example, sequencing of the entire human genome in the human genome project will be greatly simplified and enabled by the present invention.

VI. Formation of Substrate

The substrate is provided with a pattern of specific reagents which are positionally localized on the surface of the substrate. This matrix of positions is defined by the automated system which produces the substrate. The instrument will typically be one similar to that described in Pirrung et al. (1992) U.S. Pat. No. 5,143,854, and Ser. No. 07/624,120, now abandoned. The instrumentation described therein is directly applicable to the applications used here. In particular, the apparatus comprises a substrate, typically a silicon containing substrate, on which positions on the surface may be defined by a coordinate system of positions. These positions can be individually addressed or detected by the VLSIPS™ Technology apparatus.

Typically, the VLSIPS™ Technology apparatus uses optical methods used in semiconductor fabrication applications. In this way, masks may be used to photo-activate positions for attachment or synthesis of specific sequences on the substrate. These manipulations may be automated by the types of apparatus described in Pirrung et al. (1992) U.S. Pat. No. 5,143,854 and Ser. No. 07/624,120, now abandoned.

Selectively removable protecting groups allow creation of well defined areas of substrate surface having differing reactivities. Preferably, the protecting groups are selectively removed from the surface by applying a specific activator, such as electromagnetic radiation of a specific wavelength and intensity. More preferably, the specific activator exposes selected areas of surface to remove the protecting groups in the exposed areas.

Protecting groups of the present invention are used in conjunction with solid phase oligomer syntheses, such as peptide syntheses using natural or unnatural amino acids, nucleotide syntheses using deoxyribonucleic and ribonucleic acids, oligosaccharide syntheses, and the like. In addition to protecting the substrate surface from unwanted reaction, the protecting groups block a reactive end of the monomer to prevent self-polymerization. For instance, attachment of a protecting group to the amino terminus of an activated amino acid, such as the N-hydroxysuccinimide-activated ester of the amino acid prevents the amino terminus of one monomer from reacting with the activated ester portion of another during peptide synthesis.

Alternatively, the protecting group may be attached to the carboxyl group of an amino acid to prevent reaction at this site. Most protecting groups can be attached to either the amino or the carboxyl group of an amino acid, and the nature of the chemical synthesis will dictate which reactive group will require a protecting group. Analogously, attachment of a protecting group to the 5'-hydroxyl group of a nucleoside during synthesis using for example, phosphate-triester coupling chemistry, prevents the 5'-hydroxyl of one nucleoside from reacting with the 3'-activated phosphate-triester of another.

Regardless of the specific use, protecting groups are employed to protect a moiety on a molecule from reacting with another reagent. Protecting groups of the present invention have the following characteristics: they prevent selected reagents from modifying the group to which they are attached; they are stable (that is, they remain attached) to the synthesis reaction conditions; they are removable under conditions that do not adversely affect the remaining structure; and once removed, do not react appreciably with the surface or surface-bound oligomer. The selection of a suitable protecting group will depend, of course, on the chemical nature of the monomer unit and oligomer, as well as the specific reagents they are to protect against.

In a preferred embodiment, the protecting groups will be photoactivatable. The properties and uses of photoreactive protecting compounds have been reviewed. See, McCray et al., *Ann. Rev. of Biophys. and Biophys. Chem.* (1989) 18:239–270, which is incorporated herein by reference. Preferably, the photosensitive protecting groups will be removable by radiation in the ultraviolet (UV) or visible portion of the electromagnetic spectrum. More preferably, the protecting groups will be removable by radiation in the near UV or visible portion of the spectrum. In some embodiments, however, activation may be performed by other methods such as localized heating, electron beam lithography, laser pumping, oxidation or reduction with microelectrodes, and the like. Sulfonyl compounds are suitable reactive groups for electron beam lithography. Oxidative or reductive removal is accomplished by exposure of the protecting group to an electric current source, preferably using microelectrodes directed to the predefined regions of the surface which are desired for activation. A more detailed description of these protective groups is provided in Ser. No. 07/624,120, now abandoned, which is hereby incorporated herein by reference.

The density of reagents attached to a silicon substrate may be varied by standard procedures. The surface area for attachment of reagents may be increased by modifying the silicon surface. For example, a matte surface may be machined or etched on the substrate to provide more sites for attachment of the particular reagents. Another way to increase the density of reagent binding sites is to increase the derivitization density of the silicon. Standard procedures for achieving this are described, below.

One method to control the derivatization density is to highly derivatize the substrate with photochemical groups at high density. The substrate is then photolyzed for various predetermined times, which photoactivate the groups at a measurable rate, and react them with a capping reagent. By this method, the density of linker groups may be modulated by using a desired time and intensity of photoactivation.

In many applications, the number of different sequences which may be provided may be limited by the density and the size of the substrate on which the matrix pattern is generated. In situations where the density is insufficiently high to allow the screening of the desired number of sequences, multiple substrates may be used to increase the number of sequences tested. Thus, the number of sequences tested may be increased by using a plurality of different substrates. Because the VLSIPS apparatus is almost fully automated, increasing the number of substrates does not lead to a significant increase in the number of manipulations which must be performed by humans. This again leads to greater reproducibility and speed in the handling of these multiple substrates.

A. Instrumentation

The concept of using VLSIPS™ Technology generally allows a pattern or a matrix of reagents to be generated. The procedure for making the pattern is performed by any of a number of different methods. An apparatus and instrumentation useful for generating a high density VLSIPS substrate is described in detail in Pirrung et al. (1992) U.S. Pat. No. 5,143,854 and Ser. No. 07/624,120, now abandoned.

B. Binary Masking

The details of the binary masking are described in an accompanying application filed simultaneously with this, Ser. No. 07/624,120, now abandoned, whose specification is incorporated herein by reference.

For example, the binary masking technique allows for producing a plurality of sequences based on the selection of either of two possibilities at any particular location. By a series of binary masking steps, the binary decision may be the determination, on a particular synthetic cycle, whether or not to add any particular one of the possible subunits. By treating various regions of the matrix pattern in parallel, the binary masking strategy provides the ability to carry out spatially addressable parallel synthesis.

C. Synthetic Methods

The synthetic methods in making a substrate are described in the parent application, Pirrung et al. (1992) U.S. Pat. No. 5,143,854. The construction of the matrix pattern on the substrate will typically be generated by the use of photosensitive reagents. By use of photo-lithographic optical methods, particular segments of the substrate can be irradiated with light to activate or deactivate blocking agents, e.g., to protect or deprotect particular chemical groups. By an appropriate sequence of photo-exposure steps at appropriate times with appropriate masks and with appropriate reagents, the substrates can have known polymers synthesized at positionally defined regions on the substrate. Methods for synthesizing various substrates are described in Pirrung et al. (1992) U.S. Pat. No. 5,143,854 and Ser. No. 07/624,120, now abandoned. By a sequential series of these photo-exposure and reaction manipulations, a defined matrix pattern of known sequences may be generated, and is typically referred to as a VLSIPS™ Technology substrate. In the nucleic acid synthesis embodiment, nucleosides used in the synthesis of DNA by photolytic methods will typically be one of the two forms shown below:

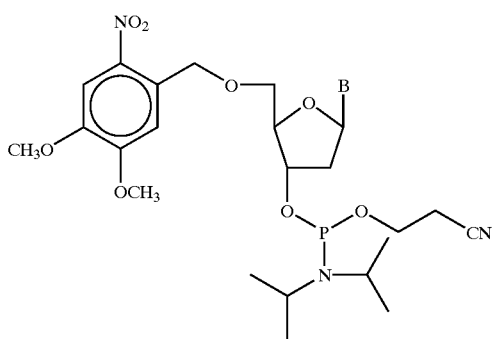

I

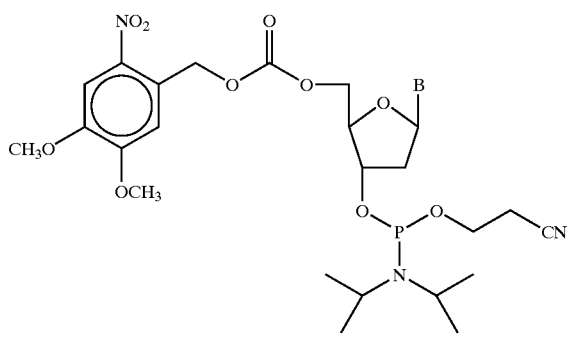

B=Adenine, Cytosine, Guanine, or Thymine

In I, the photolabile group at the 5' position is abbreviated NV (nitroveratryl) and in II, the group is abbreviated NVOC (nitroveratryl oxycarbonyl). Although not shown in FIG. C, the bases (adenine, cytosine, and guanine) contain exocyclic $NH_2$ groups which must be protected during DNA synthesis. Thymine contains no exocyclic $NH_2$ and therefore requires no protection. The standard protecting groups for these amines are shown below:

(A)

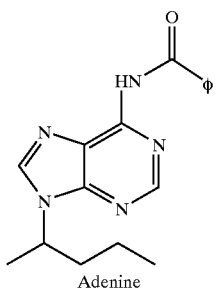

Adenine (C)

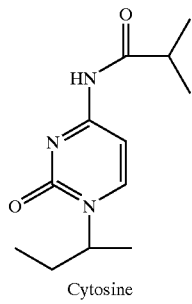

Cytosine (G)

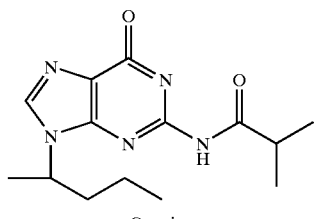

Guanine

Other amides of the general formula

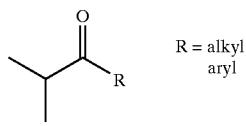

where R may be alkyl or aryl have been used.

Another type of protecting group FMOC (9-fluorenyl methoxycarbonyl) is currently being used to protect the exocyclic amines of the three bases:

(A)

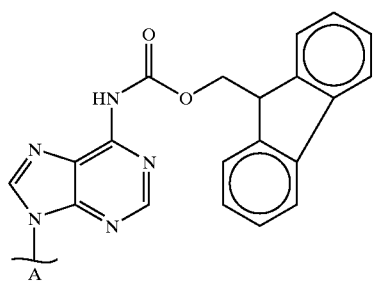

Adenine (C)

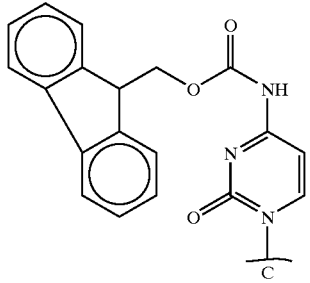

Cytosine (G)

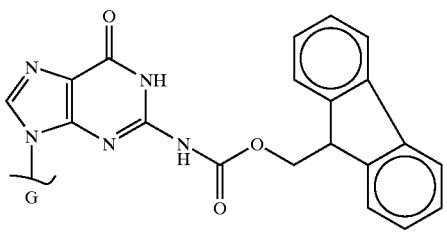

Guanine

The advantage of the FMOC group is that it is removed under mild conditions (dilute organic bases) and can be used for all three bases. The amide protecting groups require more harsh conditions to be removed ($NH_3$/MeOH with heat).

Nucleosides used as 5'-OH probes, useful in verifying correct VLSIPS synthetic function, include, for example, the following:

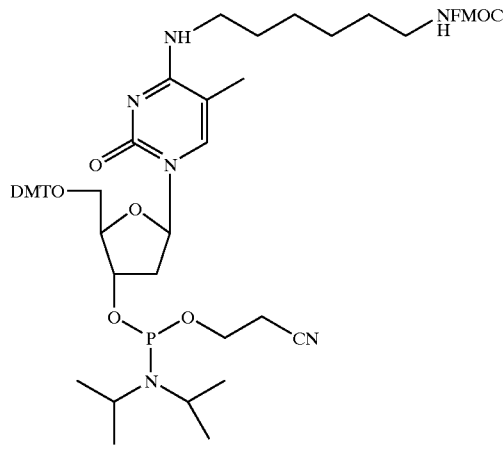

III

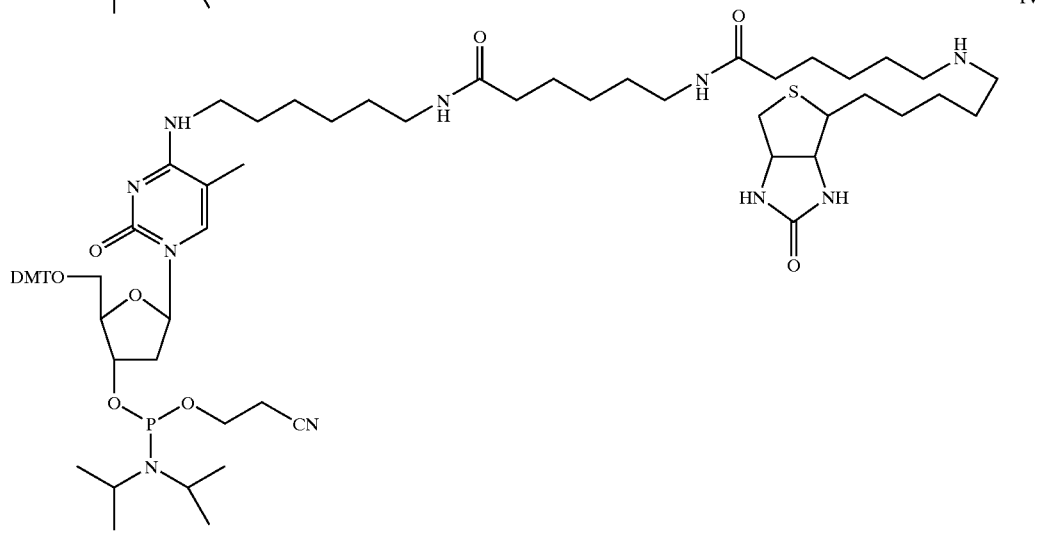

IV

These compounds are used to detect where on a substrate photolysis has occurred by the attachment of either III or V to the newly generated 5'-OH. In the case of III, after the phosphate attachment is made, the substrate is treated with a dilute base to remove the FMOC group. The resulting amine can be reacted with FITC and the substrate examined by fluorescence microscopy. This indicates the proper generation of a 5'-OH. In the case of compound IV, after the phosphate attachment is made, the substrate is treated with FITC labeled streptavidin and the substrate again may be examined by fluorescence microscopy. Other probes, although not nucleoside based, have included the following:

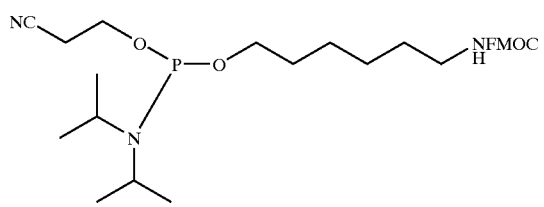

V

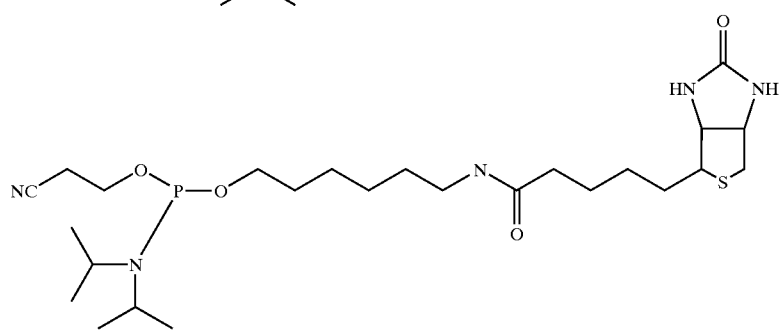

VI

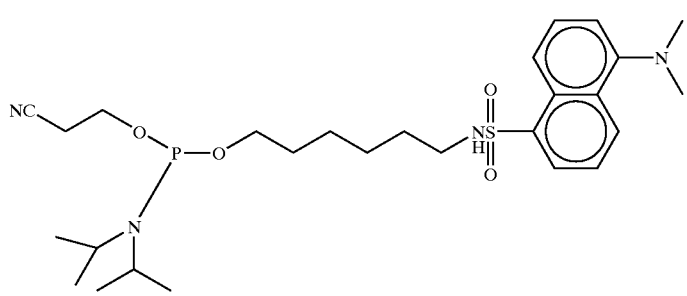

VII

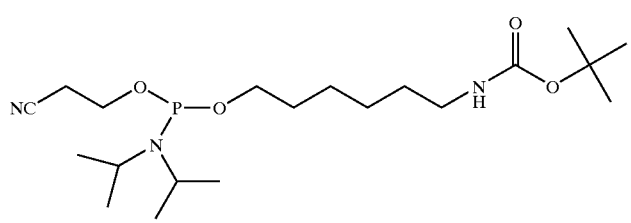

VIII

The method of attachment of the first nucleoside to the surface of the substrate depends on the functionality of the groups at the substrate surface. If the surface is amine functionalized, an amide bond is made (see example below).

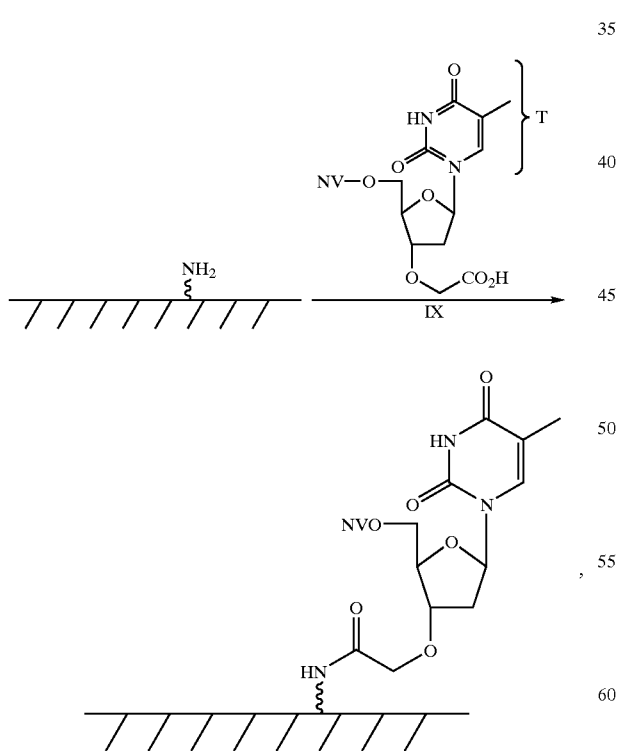

If the surface is hydroxy functionalized, a phosphate bond is made (see example below):

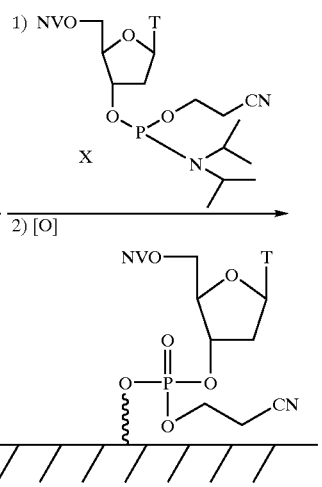

In both cases, the thymidine example is illustrated, but any one of the four phosphoramidite activated nucleosides can be used in the first step.

Photolysis of the photolabile group NV or NVOC on the 5' positions of the nucleosides is carried out at ~362 nm with an intensity of 14 mW/cm$^2$ for 10 minutes with the substrate side (side containing the photolabile group) immersed in dioxane. After the coupling of the next nucleoside is complete, the photolysis is repeated followed by another coupling until the desired oligomer is obtained.

One of the most common 3'-O-protecting groups is the ester, in particular the acetate:

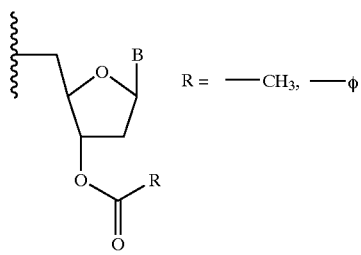

The groups can be removed by mild base treatment 0.1N NaOH/MeOH or $K_2CO_3/H_2O/MeOH$.

Another group used most often is the silyl ether:

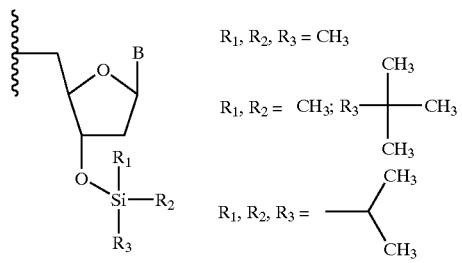

These groups can be removed by neutral conditions using 1 M tetra-n-butylammonium fluoride in THF or under acid conditions.

With respect to photodeprotection, the nitroveratryl group could also be used to protect the 3'-position.

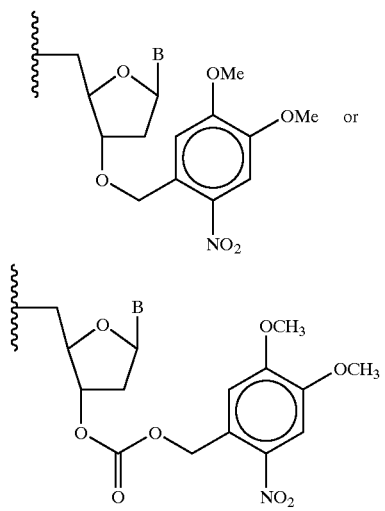

Here, light (photolysis) would be used to remove these protecting groups.

A variety of ethers can also be used in the protection of the 3'-O-position:

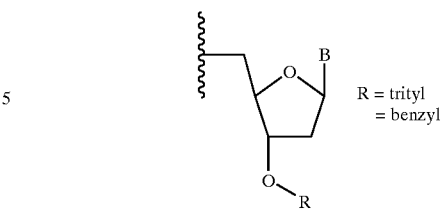

Removal of these groups usually involves acid or catalytic methods.

Note that corresponding linkages and photoblocked amino acids are described in detail in Ser. No. 07/624,120, now abandoned, which is hereby incorporated herein by reference.

Although the specificity of interactions at particular locations will usually be homogeneous due to a homogeneous polymer being synthesized at each defined location, for certain purposes, it may be useful to have mixed polymers with a commensurate mixed collection of interactions occurring at specific defined locations, or degeneracy reducing analogues, which have been discussed above and show broad specificity in binding. Then, a positive interaction signal may result from any of a number of sequences contained therein.

As an alternative method of generating a matrix pattern on a substrate, preformed polymers may be individually attached at particular sites on the substrate. This may be performed by individually attaching reagents one at a time to specific positions on the matrix, a process which may be automated. See, e.g., Ser. No. 07/435,316, now abandoned, and Barrett et al. (1993) U.S. Pat. No. 5,252,743. Another way of generating a positionally defined matrix pattern on a substrate is to have individually specific reagents which interact with each specific position on the substrate. For example, oligonucleotides may be synthesized at defined locations on the substrate. Then the substrate would have on its surface a plurality of regions having homogeneous oligonucleotides attached at each position.

In particular, at least four different substrate preparation procedures are available for treating a substrate surface. They are the standard VLSIPS™ Technology method, polymeric substrates, Durapore™, and synthetic beads or fibers. The treatment labeled "standard VLSIPS™ Technology" method is described in Ser. No. 07/624,120, now abandoned, and involves applying amino-propyltriethoxysilane to a glass surface.

The polymeric substrate approach involves either of two ways of generating a polymeric substrate. The first uses a high concentration of aminopropyltriethoxysilane (2–20%) in an aqueous ethanol solution (95%). This allows the silane compound to polymerize both in solution and on the substrate surface, which provides a high density of amines on the surface of the glass. This density is contrasted with the standard VLSIPS method. This polymeric method allows for the deposition on the substrate surface of a monolayer due to the anhydrous method used with the aforementioned silane.

The second polymeric method involves either the coating or covalent binding of an appropriate acrylic acid polymer onto the substrate surface. In particular, e.g., in DNA synthesis, a monomer such as a hydroxypropylacrylate is used to generate a high density of hydroxyl groups on the substrate surface, allowing for the formation of phosphate bonds. An example of such a compound is shown:

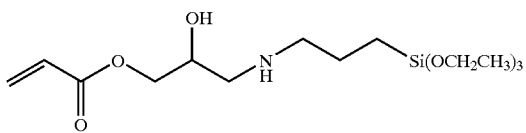

The method using a Durapore™ membrane (Millipore) consists of a polyvinylidine difluoride coating with crosslinked polyhydroxylpropyl acrylate [PVDF-HPA]:

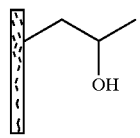

Here the building up of, e.g., a DNA oligomer, can be started immediately since phosphate bonds to the surface can be accomplished in the first step with no need for modification. A nucleotide dimer (5'-C-T-3') has been successfully made on this substrate.

The fourth method utilizes synthetic beads or fibers. This would use another substrate, such as a teflon copolymer graft bead or fiber, which is covalently coated with an organic layer (hydrophilic) terminating in hydroxyl sites (commercially available from Molecular Biosystems, Inc.) This would offer the same advantage as the Durapore™ membrane, allowing for immediate phosphate linkages, but would give additional contour by the 3-dimensional growth of oligomers.

A matrix pattern of new reagents may be targeted to each specific oligonucleotide position by attaching a complementary oligonucleotide to which the substrate bound form is complementary. For instance, a number of regions may have homogeneous oligonucleotides synthesized at various locations. Oligonucleotide sequences complementary to each of these can be individually generated and linked to a particular specific reagents. Often these specific reagents will be antibodies. As each of these is specific for finding its complementary oligonucleotide, each of the specific reagents will bind through the oligonucleotide to the appropriate matrix position. A single step having a combination of different specific reagents being attached specifically to a particular oligonucleotide will thereby bind to its complement at the defined matrix position. The oligonucleotides will typically then be covalently attached, using, e.g., an acridine dye, for photocrosslinking. Psoralen is a commonly used acridine dye for photocrosslinking purposes, see, e.g., Song et al. (1979) *Photochem. Photobiol.* 29:1177–1197; Cimino et al. (1985) *Ann. Rev. Biochem.* 54:1151–1193; Parsons (.1980) *Photochem. Photobiol.* 32:813–821; and Dattagupta et al. (1985) U.S. Pat. No. 4,542,102, and (1987) U.S. Pat. No. 4,713,326; each of which is hereby incorporated herein by reference. This method allows a single attachment manipulation to attach all of the specific reagents to the matrix at defined positions and results in the specific reagents being homogeneously located at defined positions. In many embodiments, the specific reagents will be antibodies.

In an alternative embodiment, antibody molecules may be used to specifically direct binding to defined positions on a substrate. The VLSIPS technology may be used to generate specific epitopes at each position on the substrate. Antibody molecules having specificity of interaction may be used to attach oligonucleotides, thereby avoiding the interference of internal polynucleotide sequences from binding to the substrate complementary oligonucleotides. In fact, the specificity of interaction for positional targeting may be achieved by use of nucleotide analogues which do not interact with the natural nucleotides. For example, other synthetic nucleotides have been made which undergo base pairing, thereby providing the specificity of targeting, but the synthetic nucleotides also do not interact with the natural biological nucleotides. Thus, synthetic oligonucleotides would be useful for attachment to biological nucleotides and specific targeting. Moreover, the VLSIPS synthetic processes would be useful in generating the VLSIPS substrate, and standard oligonucleotide synthesis could be applied, with minor modifications, to produce the complementary sequences which would be attached to other specific reagents.

D. Surface Immobilization

1. Caged Biotin

An alternative method of attaching reagents in a positionally defined matrix pattern is to use a caged biotin system. See Barrett et al. (1993) U.S. Pat. No. 5,252,743, which is hereby incorporated herein by reference, for additional details on the chemistry and application of caged biotin embodiments. In short, the caged biotin has a photosensitive blocking moiety which prevents the combination of avidin to biotin. At positions where the photo-lithographic process has removed the blocking group, high affinity biotin sites are generated. Thus, by a sequential series of photolithographic deblocking steps interspersed with exposure of those regions to appropriate biotin containing reagents, only those locations where the deblocking takes place will form an avidin-biotin interaction. Because the avidin-biotin binding is very tight, this will usually be virtually irreversible binding.

2. Crosslinked Interactions

The surface immobilization may also take place by photo crosslinking of defined oligonucleotides linked to specific reagents. After hybridization of the complementary oligonucleotides, the oligonucleotides may be crosslinked by a reagent by psoralen or another similar type of acridine dye. Other useful cross linking reagents are described in Dattagupta et al. (1985) U.S. Pat. No. 4,542,102, and (1987) U.S. Pat. No. 4,713,326.

In another embodiment, colony or phage plaque transfer of biological polymers may be transferred directly onto a silicon substrate. For example, a colony plate may be transferred onto a substrate having a generic oligonucleotide sequence which hybridizes to another generic complementary sequence contained on all of the vectors into which inserts are cloned. This will specifically only bind those molecules which are actually contained in the vectors containing the desired complementary sequence. This immobilization allows for producing a matrix onto which a sequence specific reagent can bind, or for other purposes. In a further embodiment, a plurality of different vectors each having a specific oligonucleotide attached to the vector may be specifically attached to particular regions on a matrix having a complementary oligonucleotide attached thereto.

VIII. Hybridization/Specific Interaction

A. General

As discussed previously in the VLSIPS™ Technology parent applications, the VLSIPS™ technology substrates may be used for screening for specific interactions with sequence specific targets or probes.

In addition, the availability of substrates having the entire repertoire of possible sequences of a defined length opens up the possibility of sequencing by hybridization. This sequence may be de novo determination of an unknown sequence, particularly of nucleic acid, verification of a sequence determined by another method, or an investigation of changes in a previously sequenced gene, locating and identifying specific changes. For example, often Maxam and Gilbert sequencing techniques are applied to sequences which have been determined by Sanger and Coulson. Each of those sequencing technologies have problems with resolving particular types of sequences. Sequencing by hybridization may serve as a third and independent method for verifying other sequencing techniques. See, e.g., (1988) *Science* 242:1245.

In addition, the ability to provide a large repertoire of particular sequences allows use of short subsequences and hybridization as a means to fingerprint a sample. This may be used in a nucleic acid, as well as other polymer embodiments. For example, fingerprinting to a high degree of specificity of sequence matching may be used for identifying highly similar samples, e.g., those exhibiting high homology to the selected probes. This may provide a means for determining classifications of particular sequences. This should allow determination of whether particular genomes of bacteria, phage, or even higher cells might be related to one another.

In addition, fingerprinting may be used to identify an individual source of biological sample. See, e.g., Lander, E. (1989) *Nature*, 339:501–505, and references therein. For example, a DNA fingerprint may be used to determine whether a genetic sample arose from another individual. This would be particularly useful in various sorts of forensic tests to determine, e.g., paternity or sources of blood samples. Significant detail on the particulars of genetic fingerprinting for identification purposes are described in, e.g., Morris et al. (1989) "Biostatistical evolution of evidence from continuous allele frequency distribution DNA probes in reference to disputed paternity of identity," *J. Forensic Science* 34:1311–1317; and Neufeld et al. (1990) *Scientific American* 262:46–53; each of which is hereby incorporated herein by reference.

In another embodiment, a fingerprinting-like procedure may be used for classifying cell types by analyzing a pattern of specific nucleic acids present in the cell. A series of antibodies may be used to identify cell markers, e.g., proteins, usually on the cell surface, but intracellular markers may also be used. Antigens which are extracellularly expressed are preferred so cell lysis is unnecessary in the screening, but intracellular markers may also be useful. The markers will usually be proteins, but may be nucleic acids, lipids, metabolites, carbohydrates, or other cellular components. See, e.g., Winkelgren, I. (1990) *Science News* 136:234–237, which indicates extracellular DNA may be common, and suggesting that such might be characteristic of cell types, stage, or physiology. This may also be useful in defining the temporal stage of development of cells, e.g., stem cells or other cells which undergo temporal changes in development. For example, the stage of a cell, or group of cells, may be tested or defined by isolating a sample of mRNA from the population and testing to see what sequences are present in messenger populations. Direct samples, or amplified samples, may be used. Where particular mRNA or other nucleic acid sequences may be characteristic of or shown to be characteristic of particular developmental stages, physiological states, or other conditions, this fingerprinting method may define them. Similar sorts of fingerprinting may be used for determining T-cell classes or perhaps even to generate classification schemes for such proteins as major histocompatibility complex antigens. Thus, the ability to make these substrates allows both the generation of reagents which will be used for defining subclasses or classes of cells or other biological materials, but also provides the mechanisms for selecting those cells which may be found in defined population groups.

In addition to cell classification defined by such a combination of properties, typically expression of extracellular antigens, the present invention also provides the means for isolating homogeneous population of cells. Once the antigenic determinants which define a cell class have been identified, these antigens may be used in a sequential selection process to isolate only those cells which exhibit the combination of defining structural properties.

The present invention may also be used for mapping sequences within a larger segment. This may be performed by at least two methods, particularly in reference to nucleic acids. Often, enormous segments of DNA are subcloned into a large plurality of subsequences. Ordering these subsequences may be important in determining the overlaps of sequences upon nucleotide determinations. Mapping may be performed by immobilizing particularly large segments onto a matrix using the VLSIPS™ Technology. Alternatively, sequences may be ordered by virtue of subsequences shared by overlapping segments. See, e.g., Craig et al. (1990) *Nuc. Acids Res.* 18:2653–2660; Michiels et al. (1987) *CABIOS* 3:203–210; and Olson et al. (1986) *Proc. Natl. Acad. Sci. USA* 83:7826–7830.

B. Important Parameters

The extent of specific interaction between reagents immobilized to the VLSIPS™ Technology substrate and another sequence specific reagent may be modified by the conditions of the interaction. Sequencing embodiments typically require high fidelity hybridization and the ability to discriminate perfect matching from imperfect matching. Fingerprinting and mapping embodiments may be performed using less stringent conditions, depending upon the circumstances.

For example, the specificity of antibody/antigen interaction may depend upon such parameters as pH, salt concentration, ionic composition, solvent composition, detergent composition and concentration, and chaotropic agent concentration. See, e.g., Harlow and Lane (1988) *Antibodies: A Laboratory Manual*, Cold Spring Harbor Press, New York. By careful control of these parameters, the affinity of binding may be mapped across different sequences.

In a nucleic acid hybridization embodiment, the specificity and kinetics of hybridization have been described in detail by, e.g., Wetmur and Davidson (1968) *J. Mol. Biol.*, 31:349–370, Britten and Kohne (1968) *Science* 161:529–530, and Kanehisa, (1984) *Nuc. Acids Res.* 12:203–213, each of which is hereby incorporated herein by reference. Parameters which are well known to affect specificity and kinetics of reaction include salt conditions, ionic composition of the solvent, hybridization temperature, length of oligonucleotide matching sequences, guanine and cytosine (GC) content, presence of hybridization accelerators, pH, specific bases found in the matching sequences, solvent conditions, and addition of organic solvents.

In particular, the salt conditions required for driving highly mismatched sequences to completion typically include a high salt concentration. The typical salt used is sodium chloride (NaCl), however, other ionic salts may be utilized, e.g., KCl. Depending on the desired stringency hybridization, the salt concentration will often be less than about 3 molar, more often less than 2.5 molar, usually less than about 2 molar, and more usually less than about 1.5 molar. For applications directed towards higher stringency matching, the salt concentrations would typically be lower.

Ordinary high stringency conditions will utilize salt concentration of less than about 1 molar, more often less then about 750 millimolar, usually less than about 500 millimolar, and may be as low as about 250 or 150 millimolar.

The kinetics of hybridization and the stringency of hybridization both depend upon the temperature at which the hybridization is performed and the temperature at which the washing steps are performed. Temperatures at which steps for low stringency hybridization are desired would typically be lower temperatures, e.g., ordinarily at least about 15° C., more ordinarily at least about 20° C., usually at least about 25° C., and. more usually at least about 30° C. For those applications requiring high stringency hybridization, or fidelity of hybridization and sequence matching, temperatures at which hybridization and washing steps are performed would typically be high. For example, temperatures in excess of about 35° C. would often be used, more often in excess of about 40° C., usually at least about 45° C., and occasionally even temperatures as high as about 50° C. or 60° C. or more. Of course, the hybridization of oligonucleotides may be disrupted by even higher temperatures. Thus, for stripping of targets from substrates, as discussed below, temperatures as high as 80° C., or even higher may be used.

The base composition of the specific oligonucleotides involved in hybridization affects the temperature of melting, and the stability of hybridization as discussed in the above references. However, the bias of GC rich sequences to hybridize faster and retain stability at higher temperatures can be compensated for by the inclusion in the hybridization incubation or wash steps of various buffers. Sample buffers which accomplish this result include the triethly-and trimethyl ammonium buffers. See, e.g., Wood et al. (1987) *Proc. Natl. Acad. Sci. USA*, 82:1585–1588, and Khrapko, K. et al. (1989) *FEBS Letters* 256:118–122.

The rate of hybridization can also be affected by the inclusion of particular hybridization accelerators. These hybridization accelerators include the volume exclusion agents characterized by dextran sulfate, or polyethylene glycol (PEG). Dextran sulfate is typically included at a concentration of between 1% and 40% by weight. The actual concentration selected depends upon the application, but typically a faster hybridization is desired in which the concentration is optimized for the system in question. Dextran sulfate is often included at a concentration of between 0.5% and 2% by weight or dextran sulfate at a concentration between about 0.5% and 5%. Alternatively, proteins which accelerate hybridization may be added, e.g., the recA protein found in *E. coli* or other homologous proteins.

With respect to those embodiments where specific reagents are not oligonucleotides, the conditions of specific interaction would depend on the affinity of binding between the specific reagent and its target. Typically parameters which would be of particular importance would be pH, salt concentration anion and cation compositions, buffer concentration, organic solvent inclusion, detergent concentration, and inclusion of such reagents such as chaotropic agents. In particular, the affinity of binding may be tested over a variety of conditions by multiple washes and repeat scans or by using reagents with differences in binding affinity to determine which reagents bind or do not bind under the selected binding and washing conditions. The spectrum of binding affinities may provide an additional dimension of information which may be very useful in identification purposes and mapping.

Of course, the specific hybridization conditions will be selected to correspond to a discriminatory condition which provides a positive signal where desired but fails to show a positive signal at affinities where interaction is not desired. This may be determined by a number of titration steps or with a number of controls which will be run during the hybridization and/or washing steps to determine at what point the hybridization conditions have reached the stage of desired specificity.

IX. Detection Methods

Methods for detection depend upon the label selected. The criteria for selecting an appropriate label are discussed below, however, a fluorescent label is preferred because of its extreme sensitivity and simplicity. Standard labeling procedures are used to determine the positions where interactions between a sequence and a reagent take place. For example, if a target sequence is labeled and exposed to a matrix of different probes, only those locations where probes do interact with the target will exhibit any signal. Alternatively, other methods may be used to scan the matrix to determine where interaction takes place. Of course, the spectrum of interactions may be determined in a temporal manner by repeated scans of interactions which occur at each of a multiplicity of conditions. However, instead of testing each individual interaction separately, a multiplicity of sequence interactions may be simultaneously determined on a matrix.

A. Labeling Technioues

The target polynucleotide may be labeled by any of a number of convenient detectable markers. A fluorescent label is preferred because it provides a very strong signal with low background. It is also optically detectable at high resolution and sensitivity through a quick scanning procedure. Other potential labeling moieties include, radioisotopes, chemiluminescent compounds, labeled binding proteins, heavy metal atoms, spectroscopic markers, magnetic labels, and linked enzymes.

Another method for labeling may bypass any label of the target sequence. The target may be exposed to the probes, and a double strand hybrid is formed at those positions only. Addition of a double strand specific reagent will detect where hybridization takes place. An intercalative dye such as ethidium bromide may be used as long as the probes themselves do not fold back on themselves to a significant extent forming hairpin loops. See, e.g., Sheldon et al. (1986) U.S. Pat. No. 4,582,789. However, the length of the hairpin loops in short oligonucleotide probes would typically be insufficient to form a stable duplex.

In another embodiment, different targets may be simultaneously sequenced where each target has a different label. For instance, one target could have a green fluorescent label and a second target could have a red fluorescent label. The scanning step will distinguish sites of binding of the red label from those binding the green fluorescent label. Each sequence can be analyzed independently from one another.

Suitable chromogens will include molecules and compounds which absorb light in a distinctive range of wavelengths so that a color may be observed, or emit light when irradiated with radiation of a particular wave length or wave length range, e.g., fluorescers. Biliproteins, e.g., phycoerythrin, may also serve as labels.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triaryl-methanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidyle-thanolamine; N,N'-dioctadecyl oxacarbocyanine; N,N'-dihexyl oxacarbocyanine; merocyanine, 4-(3' pyrenyl) butyrate; d-3-aminodesoxy equilenin; 12-(9'-anthroyl) stearate; 2-methylanthracene; 9-vinylanthracene; 2,2'-(vinylene-p-phenylene)bisbenzoxazole; p-bis[2-(4-methyl-5-phenyl-oxazolyl)]benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-[p-(2-benzimidazolyl)-phenyl] maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye may differ from the unbound dye. Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

B. Scanning System

With the automated detection apparatus, the correlation of specific positional labeling is converted to the presence on the target of sequences for which the reagents have specificity of interaction. Thus, the positional information is directly converted to a database indicating what sequence interactions have occurred. For example, in a nucleic acid hybridization application, the sequences which have interacted between the substrate matrix and the target molecule can be directly listed from the positional information. The detection system used is described in Pirrung et al. (1992) U.S. Pat. No. 5,143,854; and Ser. No. 07/624,120, now abandoned. Although the detection described therein is a fluorescence detector, the detector may be replaced by a spectroscopic or other detector. The scanning system may make use of a moving detector relative to a fixed substrate, a fixed detector with a moving substrate, or a combination. Alternatively, mirrors or other apparatus can be used to transfer the signal directly to the detector. See, e.g, Ser. No. 07/624,120, now abandoned, which is hereby incorporated herein by reference.

The detection method will typically also incorporate some signal processing to determine whether the signal at a particular matrix position is a true positive or may be a spurious signal. For example, a signal from a region which has actual positive signal may tend to spread over and provide a positive signal in an adjacent region which actually should not have one. This may occur, e.g., where the scanning system is not properly discriminating with sufficiently high resolution in its pixel density to separate the two regions. Thus, the signal over the spatial region may be evaluated pixel by pixel to determine the locations and the actual extent of positive signal. A true positive signal should, in theory, show a uniform signal at each pixel location. Thus, processing by plotting number of pixels with actual signal intensity should have a clearly uniform signal intensity. Regions where the signal intensities show a fairly wide dispersion, may be particularly suspect and the scanning system may be programmed to more carefully scan those positions.

In another embodiment, as the sequence of a target is determined at a particular location, the overlap for the sequence would necessarily have a known sequence. Thus, the system can compare the possibilities for the next adjacent position and look at these in comparison with each other. Typically, only one of the possible adjacent sequences should give a positive signal and the system might be programmed to compare each of these possibilities and select that one which gives a strong positive. In this way, the system can also simultaneously provide some means of measuring the reliability of the determination by indicating what the average signal to background ratio actually is.

More sophisticated signal processing techniques can be applied to the initial determination of whether a positive signal exists or not. See, e.g., Ser. No. 07/624,120, now abandoned.

From a listing of those sequences which interact, data analysis may be performed on a series of sequences. For example, in a nucleic acid sequence application, each of the sequences may be analyzed for their overlap regions and the original target sequence may be reconstructed from the collection of specific subsequences obtained therein. Other sorts of analyses for different applications may also be performed, and because the scanning system directly interfaces with a computer the information need not be transferred manually. This provides for the ability to handle large amounts of data with very little human intervention. This, of course, provides significant advantages over manual manipulations. Increased throughput and reproducibility is thereby provided by the automation of a vast majority of steps in any of these applications.

XI. Data Analysis

A. General

Data analysis will typically involve aligning the proper sequences with their overlaps to determine the target sequence. Although the target "sequence" may not specifically correspond to any specific molecule, especially where the target sequence is broken and fragmented in the sequencing process, the sequence corresponds to a contiguous sequence of the subfragments.

The data analysis can be performed by a computer using an appropriate program. See, e.g., Drmanac, R. et al. (1989) *Genomics* 4:114–128; and a commercially available analysis program available from the Genetic Engineering Center, P.O. Box 794, 11000 Belgrade, Yugoslavia. Although the specific manipulations necessary to reassemble the target sequence from fragments may take many forms, one embodiment uses a sorting program to sort all of the subsequences using a defined hierarchy. The hierarchy need not necessarily correspond to any physical hierarchy, but provides a means to determine, in order, which subfragments have actually been found in the target sequence. In this manner, overlaps can be checked and found directly rather than having to search throughout the entire set after each selection process. For example, where the oligonucleotide probes are 10-mers, the first 9 positions can be sorted. A particular subsequence can be selected as in the examples, to determine where the process starts. As analogous to the theoretical example provided above, the sorting procedure provides the ability to immediately find the position of the subsequence which contains the first 9 positions and can compare whether there exists more than 1 subsequence during the first 9 positions. In fact, the computer can easily generate all of the possible target sequences which contain given combination of subsequences. Typically there will be only one, but in various situations, there will be more.

An exemplary flow chart for a sequencing program is provided in FIG. 1. In general terms, the program provides for automated scanning of the substrate to determine the positions of probe and target interaction. Simple processing of the intensity of the signal may be incorporated to filter out clearly spurious signals. The positions with positive interaction are correlated with the sequence specificity of specific matrix positions, to generate the set of matching subsequences. This information is further correlated with other target sequence information, e.g., restriction fragment analysis. The sequences are then aligned using overlap data, thereby leading to possible corresponding target sequences which will, optimally, correspond to a single target sequence.

B. Hardware

A variety of computer systems may be used to run a sequencing program. The program may be written to provide both the detecting and scanning steps together and will typically be dedicated to a particular scanning apparatus. However, the components and functional steps may be separated and the scanning system may provide an output, e.g., through tape or an electronic connection into a separate computer which separately runs the sequencing analysis program. The computer may be any of a number of machines provided by standard computer manufacturers, e.g., IBM compatible machines, Apple™ machines, VAX machines, and others, which may often use a UNIX™ operating system. Of course, the hardware used to run the analysis program will typically determine what programming language would be used.

C. Software

Software would be easily developed by a person of ordinary skill in the programming art, following the flow chart provided, or based upon the input provided and the desired result.

Of course, an exemplary embodiment is a polynucleotide sequence system. However, the theoretical and mathematical manipulations necessary for data analysis of other linear molecules, such as polypeptides, carbohydrates, and various other polymers are conceptually similar. Simple branching polymers will usually also be sequencable using similar technology. However, where there is branching, it may be desired that additional recognition reagents be used to determine the nature and location of branches. This can easily be provided by use of appropriate specific reagents which would be generated by methods similar to those used to produce specific reagents for linear polymers.

XII. Substrate Reuse

Where a substrate is made with specific reagents that are relatively insensitive to the handling and processing steps involved in a single cycle of use, the substrate may often be reused. The target molecules are usually stripped off of the solid phase specific recognition molecules. Of course, it is preferred that the manipulations and conditions be selected as to be mild and to not affect the substrate. For example, if a substrate is acid labile, a neutral pH would be preferred in all handling steps. Similar sensitivities would be carefully respected where recycling is desired.

A. Removal of Label

Typically for a recycling, the previously attached specific interaction would be disrupted and removed. This will typically involve exposing the substrate to conditions under which the interaction between probe and target is disrupted. Alternatively, it may be exposed to conditions where the target is destroyed. For example, where the probes are oligonucleotides and the target is a polynucleotide, a heating and low salt wash will often be sufficient to disrupt the interactions. Additional reagents may be added such as detergents, and organic or inorganic solvents which disrupt the interaction between the specific reagents and target. In an embodiment where the specific reagents are antibodies, the substrate may be exposed to a gentle detergent which will denature the specific binding between the antibody and its target. The conditions are selected to avoid severe disruption or destruction of the structure of the antibody and to maintain the specificity of the antibody binding site. Conditions with specific pH, detergent concentration, salt concentration, ionic concentration, and other parameters may be selected which disrupt the specific interactions.

B. Storage and Preservation

As indicated above, the matrix will typically be maintained under conditions where the matrix itself and the linkages and specific reagents are preserved. Various specific preservatives may be added which prevent degradation. For example, if the reagents are acid or base labile, a neutral pH buffer will typically be added. It is also desired to avoid destruction of the matrix by growth of organisms which may destroy organic reagents attached thereto. For this reason, a preservative such as cyanide or azide may be added. However, the chemical preservative should also be selected to preserve the chemical nature of the linkages and other components of the substrate. Typically, a detergent may also be included.

C. Processes to Avoid Degradation of Oligomers

In particular, a substrate comprising a large number of oligomers will be treated in a fashion which is known to maintain the quality and integrity of oligonucleotides. These include storing the substrate in a carefully controlled environment under conditions of lower temperature, cation depletion (EDTA and EGTA), sterile conditions, and inert argon or nitrogen atmosphere.

XIII. Integrated Sequencing Strategy

A. Initial Mapping Strategy

As indicated above, although the VLSIPS™ technology may be applied to sequencing embodiments, it is often useful to integrate other concepts to simplify the sequencing. For example, nucleic acids may be easily sequenced by careful selection of the vectors and hosts used for amplifying and generating the specific target sequences. For example, it may be desired to use specific vectors which have been designed to interact most efficiently with the VLSIPS substrate. This is also important in fingerprinting and mapping strategies. For example, vectors may be carefully selected having particular complementary sequences which are designed to attach to a genetic or specific oligomer on the substrate. This is also applicable to situations where it is desired to target particular sequences to specific locations on the matrix.

In one embodiment, unnatural oligomers may be used to target natural probes to specific locations on the VLSIPS substrate. In addition, particular probes may be generated for the mapping embodiment which are designed to have specific combinations of characteristics. For example, the construction of a mapping substrate may depend upon use of another automated apparatus which takes clones isolated from a chromosome walk and attaches them individually or in bulk to the VLSIPS substrate.

In another embodiment, a variety of specific vectors having known and particular "targeting" sequences adjacent to the cloning sites may be individually used to clone a selected probe, and the isolated probe will then be targetable to a site on the VLSIPS substrate with a sequence complementary to the "target" sequence.

B. Selection of Smaller Clones

In the fingerprinting and mapping embodiments, the selection of probes may be very important. Significant mathematical analysis may be applied to determine which specific sequences should be used as those probes. Of course, for fingerprinting use, these sequences would be most desired that show significant heterogeneity across the human population. Selection of the specific sequences which would most favorably be utilized will tend to be single copy sequences within the genome.

Various hybridization selection procedures may be applied to select sequences which tend not to be repeated within a genome, and thus would tend to be conserved across individuals. For example, hybridization selections may be made for non-repetitive and single copy sequences. See, e.g., Britten and Kohne (1968) "Repeated Sequences in DNA," *Science* 161:529–540. On the other hand, it may be desired under certain circumstances to use repeated sequences. For example, where a fingerprint may be used to identify or distinguish different species, or where repetitive sequences may be diagnostic of specific species, repetitive sequences may be desired for inclusion in the fingerprinting probes. In either case, the sequencing capability will greatly assist in the selection of appropriate sequences to be used as probes.

Also as indicated above, various means for constructing an appropriate substrate may involve either mechanical or automated procedures. The standard VLSIPS automated procedure involves synthesizing oligonucleotides or short polymers directly on the substrate. In various other embodiments, it is possible to attach separately synthesized reagents onto the matrix in an ordered array. Other circumstances may lend themselves to transfer a pattern from a petri plate onto a solid substrate. Also, there are methods for site specifically directing collections of reagents to specific locations using unnatural nucleotides or equivalent sorts of targeting molecules.

While a brute force manual transfer process may be utilized sequentially for attaching various samples to successive positions, instrumentation for automating such procedures may also be devised. The automated system for performing such would preferably be relatively easily designed and conceptually easily understood.

XIV. Commercial Applications

A. Sequencing

As indicated above, sequencing may be performed either de novo or as a verification of another sequencing method. The present hybridization technology provides the ability to sequence nucleic acids and polynucleotides de novo, or as a means to verify either the Maxam and Gilbert chemical sequencing technique or Sanger and Coulson dideoxy-sequencing techniques. The hybridization method is useful to verify sequencing determined by any other sequencing technique and to closely compare two similar sequences, e.g., to identify and locate sequence differences.

Besides polynucleotide sequencing, the present invention also provides means for sequencing other polymers. This includes polypeptides, carbohydrates, synthetic organic polymers, and other polymers. Again, the sequencing may be either verification or de novo.

Of course, sequencing can be very important in many different sorts of environments. For example, it will be useful in determining the genetic sequence of particular markers in various individuals. In addition, polymers may be used as markers or for information containing molecules to encode information. For example, a short polynucleotide sequence may be included in large bulk production samples indicating the manufacturer, date, and location of manufacture of a product. For example, various drugs may be encoded with this information with a small number of molecules in a batch. For example, a pill may have somewhere from 10 to 100 to 1,000 or more very short and small molecules encoding this information. When necessary, this information may be decoded from a sample of the material using a polymerase chain reaction (PCR) or other amplification method. This encoding system may be used to provide the origin of large bulky samples without significantly affecting the properties of those samples. For example, chemical samples may also be encoded by this method thereby providing means for identifying the source and manufacturing details of lots. The origin of bulk hydrocarbon samples may be encoded. Production lots of organic compounds such as benzene or plastics may be encoded with a short molecule polymer. Food stuffs may also be encoded using similar marking molecules. Even toxic waste samples can be encoded determining the source or origin. In this way, proper disposal can be traced or more easily enforced.

Similar sorts of encoding may be provided by fingerprinting-type analysis. Whether the resolution is absolute or less so, the concept of coding information on molecules such as nucleic acids, which can be amplified and later decoded, may be a very useful and important application.

This technology also provides the ability to include markers for origins of biological materials. For example, a patented animal line may be transformed with a particular unnatural sequence which can be traced back to its origin. With a selection of multiple markers, the likelihood could be negligible that a combination of markers would have independently arisen from a source other than the patented or specifically protected source. This technique may provide a means for tracing the actual origin of particular biological materials. Bacteria, plants, and animals will be subject to marking by such encoding sequences.

B. Fingerprinting

As indicated above, fingerprinting technology may also be used for data encryption. Moreover, fingerprinting allows for significant identification of particular individuals. Where the fingerprinting technology is standardized, and used for identification of large numbers of people, related equipment and peripheral processing will be developed to accompany the underlying technology. For example, specific equipment may be developed for automatically taking a biological sample and generating or amplifying the information molecules within the sample to be used in fingerprinting analysis. Moreover, the fingerprinting substrate may be mass produced using particular types of automatic equipment. Synthetic equipment may produce the entire matrix simultaneously by stepwise synthetic methods as provided by the VLSIPS™ technology. The attachment of specific probes onto a substrate may also be automated, e.g., making use of the caged biotin technology. See, e.g., Barrett et al. (1993) U.S. Pat. No. 5,252,743. As indicated above, there are automated methods for actually generating the matrix and substrate with distinct sequence reagents positionally located at each of the matrix positions. Where such reagents are, e.g., unnatural amino acids, a targeting function may be utilized which does not interfere with a natural nucleotide functionality.

In addition, peripheral processing may be important and may be dedicated to this specific application. Thus, automated equipment for producing the substrates may be designed, or particular systems which take in a biological sample and output either a computer readout or an encoded instrument, e.g., a card or document which indicates the information and can provide that information to others. An identification having a short magnetic strip with a few million bits may be used to provide individual identification and important medical information useful in a medical emergency.

In fact, data banks may be set up to correlate all of this information of fingerprinting with medical information. This may allow for the determination of correlations between various medical problems and specific DNA sequences. By collating large populations of medical records with genetic information, genetic propensities and genetic susceptibilities to particular medical conditions may be developed. Moreover, with standardization of substrates, the micro encoding data may be also standardized to reproduce the information from a centralized data bank or on an encoding device carried on an individual person. On the other hand, if the fingerprinting procedure is sufficiently quick and routine, every hospital may routinely perform a fingerprinting operation and from that determine many important medical parameters for an individual.

In particular industries, the VLSIPS sequencing, fingerprinting, or mapping technology will be particularly appropriate. As mentioned above, agricultural livestock suppliers may be able to encode and determine whether their particular strains are being used by others. By incorporating particular markers into their genetic stocks, the markers will indicate origin of genetic material. This is applicable to seed producers, livestock producers, and other suppliers of medical or agricultural biological materials.

This may also be useful in identifying individual animals or plants. For example, these markers may be useful in determining whether certain fish return to their original breeding grounds, whether sea turtles always return to their original birthplaces, or to determine the migration patterns and viability of populations of particular endangered species. It would also provide means for tracking the sources of particular animal products. For example, it might be useful for determining the origins of controlled animal substances such as elephant ivory or particular bird populations whose importation or exportation is controlled.

As indicated above, polymers may be used to encode important information on source and batch and supplier. This is described in greater detail, e.g., "Applications of PCR to industrial problems," (1990) in *Chemical and Engineering News* 68:145, which is hereby incorporated herein by reference. In fact, the synthetic method can be applied to the storage of enormous amounts of information. Small substrates may encode enormous amounts of information, and its recovery will make use of the inherent replication capacity. For example, on regions of 10 $\mu$m×10 $\mu$m, 1 cm$^2$ has 10$^6$ regions. In theory, the entire human genome could be attached in 1000 nucleotide segments on a 3 cm$^2$ surface. Genomes of endangered species may be stored on these substrates.

Fingerprinting may also be used for genetic tracing or for identifying individuals for forensic science purposes. See, e.g., Morris, J. et al. (1989) "Biostatistical Evaluation of Evidence From Continuous Allele Frequency Distribution DNA Probes in Reference to Disputed Paternity and Identity," *J. Forensic Science* 34:1311–1317, and references provided therein; each of which is hereby incorporated herein by reference.

In addition, the high resolution fingerprinting allows the distinguishability to high resolution of particular samples. As indicated above, new cell classifications may be defined based on combinations of a large number of properties. Similar applications will be found in distinguishing different species of animals or plants. In fact, microbial identification may become dependent on characterization of the genetic content. Tumors or other cells exhibiting abnormal physiology will be detectable by use of the present invention. Also, knowing the genetic fingerprint of a microorganism may provide very useful information on how to treat an infection by such organism.

Modifications of the fingerprint embodiments may be used to diagnose the condition of the organism. For example, a blood sample is presently used for diagnosing any of a number of different physiological conditions. A multi-dimensional fingerprinting method made available by the present invention could become a routine means for diagnosing an enormous number of physiological features simultaneously. This may revolutionize the practice of medicine in providing information on an enormous number of parameters together at one time. In another way, the genetic predisposition may also revolutionize the practice of medicine providing a physician with the ability to predict the likelihood of particular medical conditions arising at any particular moment. It also provides the ability to apply preventive medicine.

The present invention might also find application in use for screening new drugs and new reagents which may be very important in medical diagnosis or other applications. For example, a description of generating a population of monoclonal antibodies with defined specificities may be very useful for producing various drugs or diagnostic reagents.

Also available are kits with the reagents useful for performing sequencing, fingerprinting, and mapping procedures. The kits will have various compartments with the desired necessary reagents, e.g., substrate, labeling reagents for target samples, buffers, and other useful accompanying products.

C. Mapping

The present invention also provides the means for mapping sequences within enormous stretches of sequence. For example, nucleotide sequences may be mapped within enormous chromosome size sequence maps. For example, it would be possible to map a chromosomal location within the chromosome which contains hundreds of millions of nucleotide base pairs. In addition, the mapping and fingerprinting embodiments allow for testing of chromosomal translocations, one of the standard problems for which amniocentesis is performed.

Thus, the present invention provides a powerful tool and the means for performing sequencing, fingerprinting, and mapping functions on polymers. Although most easily and directly applicable to polynucleotides, polypeptides, carbohydrates, and other sorts of molecules can be advantageously utilized using the present technology.

The present invention will be better understood by reference to the following illustrative examples. The following examples are offered by way of illustration and not by way of limitation.

EXPERIMENTAL

I. Sequencing
  A. polynucleotide
  B. polypeptide
  C. short peptide 1. Herz antibody identification
II. Fingerprinting
  A. polynucleotide fingerprint
  B. peptide fingerprint
  C. cell classification scheme
  D. temporal development scheme 1. developmental antigens 2. developmental mRNA expression
  E. diagnostic test 1. viral identification 2. bacterial identification 3. other microbiological identifications 4. allergy test (immobilized antigens)
  F. individual (animal/plant) identification 1. genetic 2. immunological
  G. genetic screen 1. test alleles with markers 2. amniocentesis
III. Mapping
  A. positionally located clones (caged biotin) 1. short probes, long targets 2. long targets, short probes
  B. positionally defined clones
IV. Conclusion Relevant applications whose techniques are incorporated herein by reference are Pirrung, et al., Ser. No. 07/362,901, filed Jun. 7, 1989, now abandoned; Pirrung et al. (1992) U.S. Pat. No. 5,143,854; Barrett, et al., Ser. No. 07/435,316 filed Nov. 13, 1989, now abandoned; Barrett, et al. (1993) U.S. Pat. No. 5,252,743; and commonly assigned and simultaneously filed applications Ser. No. 07/624,120, now abandoned, and Ser. No. 07/626,730.

Also, additional relevant techniques are described, e.g., in Sambrook, J., et al. (1989) *Molecular Cloning: a Laboratory Manual*, 2d Ed., vols 1–3, Cold Spring Harbor Press, New York; Greenstein and Winitz (1961) *Chemistry of the Amino Acids*, Wiley and Sons, New York; Bodzansky, M. (1988) *Peptide Chemistry: a Practical Textbook*, Springer-Verlag, New York; Harlow and Lane (1988) *Antibodies: A Laboratory Manual*, Cold Spring Harbor Press, New York; Glover, D. (ed.) (1987) *DNA Cloning: A Practical Approach*, vols 1–3, IRL Press, Oxford; Bishop and Rawlings (1987) *Nucleic Acid and Protein Sequence Analysis: A Practical Approach*, IRL Press, Oxford; Hames and Higgins (1985) *Nucleic Acid Hybridisation: A Practical Approach*, IRL Press, Oxford; Wu et al. (1989) *Recombinant DNA Methodology*, Academic Press, San Diego; Goding (1986) *Monoclonal Antibodies: Principles and Practice*, (2d ed.), Academic Press, San Diego; Finegold and Barron (1986) *Bailey and Scott's Diagnostic Microbiology*, (7th ed.), Mosby Co., St. Louis; Collins et al. (1989) *Microbiological Methods*, (6th ed.), Butterworth, London; Chaplin and Kennedy (1986) *Carbohydrate Analysis: A Practical Approach*, IRL Press, Oxford; Van Dyke (ed.) (1985) *Bioluminescence and Chemiluminescence: Instruments and Applications*, vol 1, CRC Press, Boca Rotan; and Ausubel et al. (ed.) (1990) *Current Protocols in Molecular Biology*, Greene Publishing and Wiley-Interscience, New York; each of which is hereby incorporated herein by reference.

The following examples are provided to illustrate the efficacy of the inventions herein. All operations were conducted at about ambient temperatures and pressures unless indicated to the contrary.

I. Sequencing

A. Polynucleotide

1. HPLC of the Photolysis of 5'-O-Nitroveratryl-thymidine.

In order to determine the time for photolysis of 5'-O-nitroveratryl thymidine to thymidine a 100 $\mu$M solution of NV-Thym-OH (5'-O-nitroveratryl thymidine) in dioxane was made and ~200 $\mu$l aliquots were irradiated (in a quartz cuvette 1 cm×2 mm) at 362.3 nm for 20 sec, 40 sec, 60 sec, 2 min, 5 min, 10 min, 15 min, and 20 min. The resulting irradiated mixtures were then analyzed by HPLC using a Varian MicroPak SP column ($C_{18}$ analytical) at a flow rate of 1 ml/min and a solvent system of 40% $CH_3CN$ and 60% water. Thymidine has a retention time of 1.2 min and NVO-Thym-OH has a retention time of 2.1 min. It was seen that after 10 min of exposure the deprotection was complete.

2. Preparation and Detection of Thymidine-Cytidine dimer (FITC)

The reaction is illustrated:

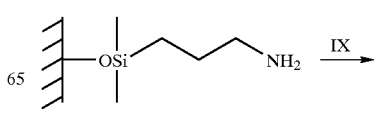

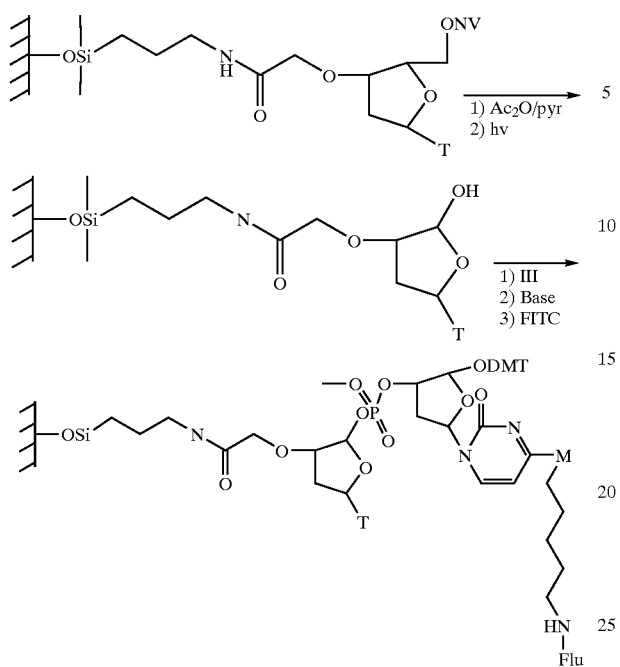

To an aminopropylated glass slide (standard VLSIPS™ Technology) was added a mixture of the following:

12.2 mg of NVO-Thym-CO$_2$H (IX)

3.4 mg of HOBT (N-hydroxybenztriazal)

8.8 μl DIEA (Diisopropylethylamine)

11.1 mg BOP reagent 2.5 ml DMF

After 2 h coupling time (standard VLSIPS) the plate was washed, acetylated with acetic anhydride/pyridine, washed, dried, and photolyzed in dioxane at 362 nm at 14 mW/cm$^2$ for 10 min using a 500 μm checkerboard mask. The slide was then taken and treated with a mixture of the following:

107 mg of FMOC-amine modified C (III)

21 mg of tetrazole 1 ml anhydrous CH$_3$CN

After being treated for approximately 8 min, the slide was washed off with CH$_3$CN, dried, and oxidized with I$_2$/H$_2$O/THF/lutidine for 1 min. The slide was again washed, dried, and treated for 30 min with a 20% solution of DBU in DMF. After thorough rinsing of the slide, it was next exposed to a FITC solution (1 mM fluorescein isothiocyanate [FITC] in DMF) for 50 min, then washed, dried, and examined by fluorescence microscopy. This reaction is illustrated:

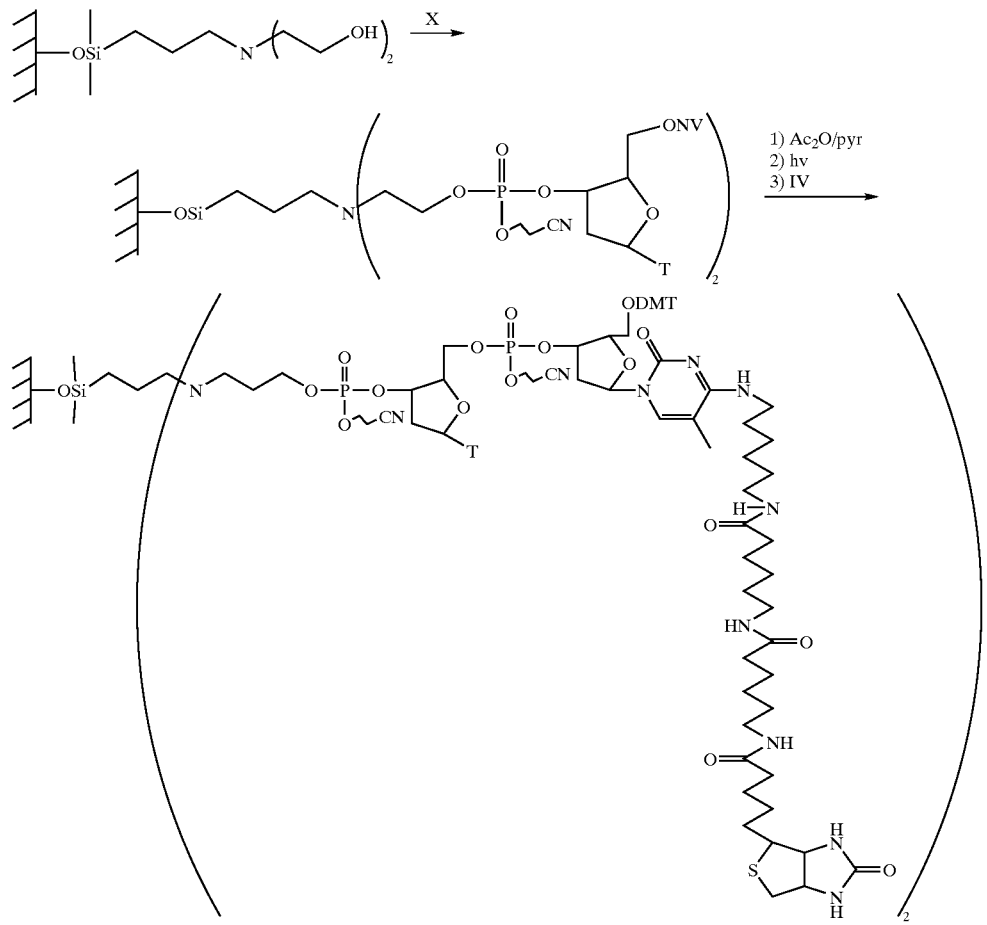

3. Preparation and Detection of Thymidine-Cytidine dimer (Biotin)

An aminopropyl glass slide, was soaked in a solution of ethylene oxide (20% in DMF) to generate a hydroxylated surface. The slide was added to a mixture of the following:

32 mg of NVO-T-OCED (X)

11 mg of tetrazole 0.5 ml of anhydrous $CH_3CN$

After 8 min the plate was then rinsed with acetonitrile, then oxidized with $I_2/H_2O/THF/lutidine$ for 1 min, washed and dried. The slide was then exposed to a 1:3 mixture of acetic anhydride:pyridine for 1 h, then washed and dried. The substrate was then photolyzed in dioxane at 362 nm at 14 $mW/cm^2$ for 10 min using a 500 $\mu$m checkerboard mask, dried, and then treated with a mixture of the following:

65 mg of biotin modified C (IV)

11 mg of tetrazole 0.5 ml anhydrous $CH_3CN$

After 8 min the slide was washed with $CH_3CN$ then oxidized with $I_2/H_2O/THF/lutidine$ for 1 min, washed, and then dried. The slide was then soaked for 30 min in a PBS/0.05% Tween 20 buffer and the solution then shaken off. The slide was next treated with FITC-labeled streptavidin at 10 $\mu$g/ml in the same buffer system for 30 min. After this time the streptavidin-buffer system was rinsed off with fresh PBS/0.05% Tween 20 buffer and then the slide was finally agitated in distilled water for about ½ h. After drying, the slide was examined by fluorescence microscopy.

4. Substrate Preparation

Before attachment of reactive groups it is preferred to clean the substrate which is, in a preferred embodiment, a glass substrate such as a microscope slide or cover slip. A roughened surface will be useable but a plastic or other solid substrate is also appropriate. According to one embodiment the slide is soaked in an alkaline bath consisting of, e.g., 1 liter of 95% ethanol with 120 ml of water and 120 grams of sodium hydroxide for 12 hours. The slides are washed with a buffer and under running water, allowed to air dry, and rinsed with a solution of 95% ethanol.

The slides are then aminated with, e.g., aminopropyltriethoxysilane for the purpose of attaching amino groups to the glass surface on linker molecules, although other omega functionalized silanes could also be used for this purpose. In one embodiment 0.1% aminopropyltriethoxysilane is utilized, although solutions with concentrations from $10^{-7}$% to 10% may be used, with about $10^{-3}$% to 2% preferred. A 0.1% mixture is prepared by adding to 100 ml of a 95% ethanol/5% water mixture, 100 microliters ($\mu$l) of aminopropyltriethoxysilane. The mixture is agitated at about ambient temperature on a rotary shaker for an appropriate amount of time, e.g., about 5 minutes. 500 $\mu$l of this mixture is then applied to the surface of one side of each cleaned slide. After 4 minutes or more, the slides are decanted of this solution and thoroughly rinsed three times or more by dipping in 100% ethanol.

After the slides dry, they are heated in a 110–120° C. vacuum oven for about 20 minutes, and then allowed to cure at room temperature for about 12 hours in an argon environment. The slides are then dipped into DMF (dimethylformamide) solution, followed by a thorough washing with methylene chloride.

5. Linker Attachment, Blocking of Free Sites

The aminated surface of the slide is then exposed to about 500 $\mu$l of, for example, a 30 millimolar (mM) solution of NVOC-nucleotide- NHS (N-hydroxysuccinimide) in DMF for attachment of a NVOC-nucleotide to each of the amino groups. See, e.g., SIGMA Chemical Company for various nucleotide derivatives. The surface is washed with, for example, DMF, methylene chloride, and ethanol.

Any unreacted aminopropyl silane on the surface, i.e., those amino groups which have not had the NVOC-nucleotide attached, are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

6. Synthesis of Eight Trimers of C and T

FIG. 2 illustrates a possible synthesis of the eight trimers of the two-monomer set: cytosine and thymine (represented by C and T, respectively). A glass slide bearing silane groups terminating in 6-nitroveratryloxycarboxamide (NVOC-NH) residues is prepared as a substrate. Active esters (pentafluorophenyl, OBt, ect.) of cytosine and thymine protected at the 5' hydroxyl group with NVOC are prepared as reagents. While not pertinent to this example, if side chain protecting groups are required for the monomer set, these must not be photoreactive at the wavelength of light used to protect the primary chain.

For a monomer set of size n, n×1 cycles are required to synthesize all possible sequences of length 1. A cycle consists of:

1. Irradiation through an appropriate mask to expose the 5'-OH groups at the sites where the next residue is to be added, with appropriate washes to remove the by-products of the deprotection.
2. Addition of a single activated and protected (with the same photochemically-removable group) monomer, which will react only at the sites addressed in step 1, with appropriate washes to remove the excess reagent from the surface.

The above cycle is repeated for each member of the monomer set until each location on the surface has been extended by one residue in one embodiment. In other embodiments, several residues are sequentially added at one location before moving on to the next location. Cycle times will generally be limited by the coupling reaction rate, now as short as about 10 min in automated oligonucleotide synthesizers. This step is optionally followed by addition of a protecting group to stabilize the array for later testing. For some types of polymers (e.g., peptides), a final deprotection of the entire surface (removal of photoprotective side chain groups) may be required.

More particularly, as shown in FIG. 2A, the glass 20 is provided with regions 22, 24, 26, 28, 30, 32, 34, and 36. Regions 30, 32, 34, and 36 are masked, indicated by the hatched regions, as shown in FIG. 2B and the glass is irradiated by the bright regions 22, 24, 26, and 28, and exposed to a reagent containing a photosensitive blocked C (e.g., cytosine derivative), with the resulting structure shown in FIG. 2C. The substrate is carefully washed and the reactants removed. Thereafter, regions 22, 24, 26, and 28 are masked, as indicated by the hatched region, the glass is irradiated (as shown in FIG. 2D), as indicated by the bright regions, at 30, 32, 34, and 36, and exposed to a photosensitive blocked reagent containing T (e.g., thymine derivative), with the resulting structure shown in FIG. 2E. The process proceeds, consecutively masking and exposing the sections as shown until the structure shown in FIG. 2M is obtained. The glass is irradiated and the terminal groups are, optionally, capped by acetylation. As shown, all possible trimers of cytosine/thymine are obtained.

In this example, no side chain protective group removal is necessary, as might be common in modified nucleotides. If it is desired, side chain deprotection may be accomplished by treatment with ethanedithiol and trifluoroacetic acid.

In general, the number of steps needed to obtain a particular polymer chain is defined by:

$$n \times l \quad (1)$$

where:
n=the number of monomers in the basis set of monomers, and
l=the number of monomer units in a polymer chain.

Conversely, the synthesized number of sequences of length l will be:

$$n^l. \quad (2)$$

Of course, greater diversity is obtained by using masking strategies which will also include the synthesis of polymers having a length of less than l. If, in the extreme case, all polymers having a length less than or equal to l are synthesized, the number of polymers synthesized will be:

$$n^l + n^{l-1} + \ldots + n^1. \quad (3)$$

The maximum number of lithographic steps needed will generally be n for each "layer" of monomers, i.e., the total number of masks (and, therefore, the number of lithographic steps) needed will be n×l. The size of the transparent mask regions will vary in accordance with the area of the substrate available for synthesis and the number of sequences to be formed. In general, the size of the synthesis areas will be:

$$\text{size of synthesis areas} = (A)/(S)$$

where:
A is the total area available for synthesis; and
S is the number of sequences desired in the area.

It will be appreciated by those of skill in the art that the above method could readily be used to simultaneously produce thousands or millions of oligomers on a substrate using the photolithographic techniques disclosed herein. Consequently, the method results in the ability to practically test large numbers of, for example, di, tri, tetra, penta, hexa, hepta, octa, nona, deca, even dodecanucleotides, or larger polynucleotides (or correspondingly, polypeptides).

The above example has illustrated the method by way of a manual example. It will of course be appreciated that automated or semi-automated methods could be used. The substrate would be mounted in a flow cell for automated addition and removal of reagents, to minimize the volume of reagents needed, and to more carefully control reaction conditions. Successive masks will be applicable manually or automatically. See, e.g., Pirrung et al. (1992) U.S. Pat. No. 5,143,854 and Ser. No. 07/624,120, now abandoned.

7. Labeling of Target

The target oligonucleotide can be labeled using standard procedures referred to above. As discussed, for certain situations, a reagent which recognizes interaction, e.g., ethidium bromide, may be provided in the detection step. Alternatively, fluorescence labeling techniques may be applied, see, e.g., Smith, et al. (1986) *Nature*, 321: 674–679; and Prober, et al. (1987) *Science*, 238:336–341. The techniques described therein will be followed with minimal modifications as appropriate for the label selected.

8. Dimers of A, C, G, and T

The described technique may be applied, with photosensitive blocked nucleotides corresponding to adenine, cytosine, guanine, and thymine, to make combinations of polynucleotides consisting of each of the four different nucleotides. All 16 possible dimers would be made using a minor modification of the described method.

9. 10-mers of A, C, G, and T

The described technique for making dimers of A, C, G, and T may be further extended to make longer oligonucleotides. The automated system described, e.g., in Pirrung et al. (1992) U.S. Pat. No. 5,143,854, and Ser. No. 07/624,120, now abandoned, can be adapted to make all possible 10-mers composed of the 4 nucleotides A, C, G, and T. The photosensitive, blocked nucleotide analogues have been described above, and would be readily adaptable to longer oligonucleotides.

10. Specific Recognition Hybridization to 10-mers

The described hybridization conditions are directly applicable to the sequence specific recognition reagents attached to the substrate, produced as described immediately above. The 10-mers have an inherent property of hybridizing to a complementary sequence. For optimum discrimination between full matching and some mismatch, the conditions of hybridization should be carefully selected, as described above. Careful control of the conditions, and titration of parameters should be performed to determine the optimum collective conditions.

11. Hybridization

Hybridization conditions are described in detail, e.g., in Hames and Higgins (1985) *Nucleic Acid Hybridisation: A Practical Approach*; and the considerations for selecting particular conditions are described, e.g., in Wetmur and Davidson, (1988) *J. Mol. Biol.* 31:349–370, and Wood et al. (1985) *Proc. Natl. Acad. Sci. USA* 82:1585–1588. As described above, conditions are desired which can distinguish matching along the entire length of the probe from where there is one or more mismatched bases. The length of incubation and conditions will be similar, in many respects, to the hybridization conditions used in Southern blot transfers. Typically, the GC bias may be minimized by the introduction of appropriate concentrations of the alkylammonium buffers, as described above.

Titration of the temperature and other parameters is desired to determine the optimum conditions for specificity and distinguishability of absolutely matched hybridization from mismatched hybridization.

A fluorescently labeled target or set of targets are generated, as described in Prober, et al. (1987) *Science* 238:336–341, or Smith, et al. (1986) *Nature* 321:674–679. Preferably, the target or targets are of the same length as, or slightly longer, than the oligonucleotide probes attached to the substrate and they will have known sequences. Thus, only a few of the probes hybridize perfectly with the target, and which particular ones did would be known.

The substrate and probes are incubated under appropriate conditions for a sufficient period of time to allow hybridization to completion. The time is measured to determine when the probe-target hybridizations have reached completion. A salt buffer which minimizes GC bias is preferred, incorporating, e.g., buffer, such as tetramethyl ammonium or tetraethyl ammonium ion at between about 2.4 and 3.0 M. See Wood, et al. (1985) *Proc. Nat'l Acad. Sci. USA* 82:1585–1588. This time is typically at least about 30 min, and may be as long as about 1–5 days. Typically very long matches will hybridize more quickly, very short matches will hybridize less quickly, depending upon relative target and probe concentrations. The hybridization will be performed under conditions where the reagents are stable for that time duration.

Upon maximal hybridization, the conditions for washing are titrated. Three parameters initially titrated are time, temperature, and cation concentration of the wash step. The matrix is scanned at various times to determine the conditions at which the distinguishability between true perfect hybrid and mismatched hybrid is optimized. These conditions will be preferred in the sequencing embodiments.

12. Positional Detection of Specific Interaction

As indicated above, the detection of specific interactions may be performed by detecting the positions where the labeled target sequences are attached. Where the label is a fluorescent label, the apparatus described, e.g., in Pirrung et al. (1992) U.S. Pat. No. 5,143,854; and Ser. No. 07/624,120, now abandoned, may be advantageously applied. In particular, the synthetic processes described above will result in a matrix pattern of specific sequences attached to the substrate, and a known pattern of interactions can be converted to corresponding sequences.

In an alternative embodiment, a separate reagent which differentially interacts with the probe and interacted probe/targets can indicate where interaction occurs or does not occur. A single-strand specific reagent will indicate where no interaction has taken place, while a double-strand specific reagent will indicate where interaction has taken place. An intercalating dye, e.g., ethidium bromide, may be used to indicate the positions of specific interaction.

13. Analysis

Conversion of the positional data into sequence specificity will provide the set of subsequences whose analysis by overlap segments, may be performed, as described above. Analysis is provided by the methodology described above, or using, e.g., software available from the Genetic Engineering Center, P.O. Box 794, 11000 Belgrade, Yugoslavia (Yugoslav group). See, also, Macevicz, PCT publication no. WO 90/04652, which is hereby incorporated herein by reference.

B. Polypeptide

The description of the preparation of short peptides on a substrate incorporates by reference sections in Pirrung et al. (1992) U.S. Pat. No. 5,143,854, and described below.

1. Slide Preparation

Preparation of the substrate follows that described above for nucleotides.

2. Linker Attachment, Blocking of Free Sites

The aminated surface of the slide is exposed to about 500 $\mu$l of, e.g., a 30 millimolar (mM) solution of NVOC-GABA (gamma amino butyric acid) NHS (N-hydroxysuccinimide) in DMF for attachment of a NVOC-GABA to each of the amino groups. The surface is washed with, for example, DMF, methylene chloride, and ethanol. See Ser. No. 07,624, 120, now abandoned, for details on amino acid chemistry.

Any unreacted aminopropyl silane on the surface, i.e., those amino groups which have not had the NVOC-GABA attached, are now capped with acetyl groups (to prevent further reaction) by exposure to a 1:3 mixture of acetic anhydride in pyridine for 1 hour. Other materials which may perform this residual capping function include trifluoroacetic anhydride, formicacetic anhydride, or other reactive acylating agents. Finally, the slides are washed again with DMF, methylene chloride, and ethanol.

3. Synthesis of 8 Trimers of "A" and "B"

See Pirrung et al. (1992) U.S. Pat. No. 5,143,854 which describes the preparation of glycine and phenylalanine trimers. The technique is similar to the method described above for making triners of C and T, but substituting photosensitive blocked glycine for the C derivative and photosensitive blocked phenylalanine for the T derivative.

4. Synthesis of a Dimer of an Aminopropyl Group and a Fluorescent Group

In synthesizing the dimer of an aminopropyl group and a fluorescent group, a functionalized Durapore™ membrane was used as a substrate. The Durapore™ membrane was a polyvinylidine difluoride with aminopropyl groups. The aminopropyl groups were protected with the DDZ group by reaction of the carbonyl chloride with the amino groups, a reaction readily known to those of skill in the art. The surface bearing these groups was placed in a solution of THF and contacted with a mask bearing a checkerboard pattern of 1 mm opaque and transparent regions. The mask was exposed to ultraviolet light having a wavelength down to at least about 280 nm for about 5 minutes at ambient temperature, although a wide range of exposure times and temperatures may be appropriate in various embodiments of the invention. For example, in one embodiment, an exposure time of between about 1 and 5000 seconds may be used at process temperatures of between −70 and +50° C.

In one preferred embodiment, exposure times of between about 1 and 500 seconds at about ambient pressure are used. In some preferred embodiments, pressure above ambient is used to prevent evaporation.

The surface of the membrane was then washed for about 1 hour with a fluorescent label which included an active ester bound to a chelate of a lanthanide. Wash times will vary over a wide range of values from about a few minutes to a few hours. These materials fluoresce in the red and the green visible region. After the reaction with the active ester in the fluorophore was complete, the locations in which the fluorophore was bound could be visualized by exposing them to ultraviolet light and observing the red and the green fluorescence. It was observed that the derivatized regions of the substrate closely corresponded to the original pattern of the mask.

5. Demonstration of Signal Capability

Signal detection capability was demonstrated using a low-level standard fluorescent bead kit manufactured by Flow Cytometry Standards and having model no. 824. This kit includes 5.8 $\mu$m diameter beads, each impregnated with a known number of fluorescein molecules.

One of the beads was placed in the illumination field on the scan stage in a field of a laser spot which was initially shuttered. After being positioned in the illumination field, the photon detection equipment was turned on. The laser beam was unblocked and it interacted with the particle bead, which then fluoresced. Fluorescence curves of beads impregnated with 7,000 and 29,000 fluorescein molecules, are shown in FIGS. 11A and 11B, respectively of Pirrung et al. (1992) U.S. Pat. No. 5,143,854. On each curve, traces for beads without fluorescein molecules are also shown. These experiments were performed with 488 nm excitation, with 100 $\mu$W of laser power. The light was focused through a 40 power 0.75 NA objective.

The fluorescence intensity in all cases started off at a high value and then decreased exponentially. The fall-off in intensity is due to photobleaching of the fluorescein molecules. The traces of beads without fluorescein molecules are used for background subtraction. The difference in the initial exponential decay between labeled and nonlabeled beads is integrated to give the total number of photon counts, and this number is related to the number of molecules per bead. Therefore, it is possible to deduce the number of photons per fluorescein molecule that can be detected. This calculation indicates the radiation of about 40 to 50 photons per fluorescein molecule are detected.

6. Determination of the Number of Molecules Per Unit Area

Aminopropylated glass microscope slides prepared according to the methods discussed above were utilized in order to establish the density of labeling of the slides. The free amino termini of the slides were reacted with FITC (fluorescein isothiocyanate) which forms a covalent linkage with the amino group. The slide is then scanned to count the number of fluorescent photons generated in a region which, using the estimated 40–50 photons per fluorescent molecule, enables the calculation of the number of molecules which are on the surface per unit area.

A slide with aminopropyl silane on its surface was immersed in a 1 mM solution of FITC in DMF for 1 hour at about ambient temperature. After reaction, the slide was washed twice with DMF and then washed with ethanol, water, and then ethanol again. It was then dried and stored in the dark until it was ready to be examined.

Through the use of curves similar to those shown in FIG. 11 of Pirrung et al. (1992) U.S. Pat. No. 5,143,854, and by integrating the fluorescent counts under the exponentially decaying signal, the number of free amino groups on the surface after derivitization was determined. It was determined that slides with labeling densities of 1 fluorescein per $10^3 \times 10^3$ to ~2×2 nm could be reproducibly made as the concentration of aminopropyltriethoxysilane varied from $10^{-5}\%$ to $10^{-1}\%$.

7. Removal of NVOC and Attachment of a Fluorescent Marker

NVOC-GABA groups were attached as described above. The entire surface of one slide was exposed to light so as to expose a free amino group at the end of the gamma amino butyric acid. This slide, and a duplicate which was not exposed, were then exposed to fluorescein isothiocyanate (FITC).

FIG. 12A of Pirrung et al. (1992) U.S. Pat. No. 5,143,854 illustrates the slide which was not exposed to light, but which was exposed to FITC. The units of the x axis are time and the units of the y axis are counts. The trace contains a certain amount of background fluorescence. The duplicate slide was exposed to 350 nm broadband illumination for about 1 minute (12 mW/cm$^2$, ~350 nm illumination), washed and reacted with FITC. A large increase in the level of fluorescence is observed, which indicates photolysis has exposed a number of amino groups on the surface of the slides for attachment of a fluorescent marker.

8. Use of a Mask in Removal of NVOC

The next experiment was performed with a 0.1% aminopropylated slide. Light from a Hg-Xe arc lamp was imaged onto the substrate through a laser-ablated chrome-on-glass mask in direct contact with the substrate.

The slide was illuminated for approximately 5 minutes, with 12 mW of 350 nm broadband light and then reacted with the 1 nM FITC solution. It was put on the laser detection scanning stage and a graph was plotted as a two-dimensional representation of position color-coded for fluorescence intensity. The experiment was repeated a nuber of times through various masks. The fluorescence patterns for a 100×100 µm mask, a 50 µm mask, a 20 µm mask, and a 10 µm mask indicate that the mask pattern is distint down to at least about 10 µm squares using this lithographic technique.

9. Attachment of YGGFL and Subsequent Exposure to Herz Antibody and Goat Anti-mouse Antibody In order to establish that receptors to a particular polypeptide sequence would bind to a surface-bound peptide and be detected, Leu enkephalin was coupled to the surface and recognized by an antibody. A slide was derivatized with 0.1% amino propyl-triethoxysilande and protected with NVOC. A 500 µm checkerboard mask was used to expose the slide in a flow cell using backside contact printing. The Leu enkephalin sequence (H$_2$N-tyrosine, glycine, glycine, phenylalanine, leucine-COOH, otherwise referred to herein as YGGFL) was attached via its carboxy end to the exposed amino groups on the surface of the slide. The peptide was added in DMF solution with the BOP/HOBT/DIEA coupling reagents and recirculated through the flow cell for 2 hours at room temperature.

A first antibody, known as the Herz antibody, was applied to the surface of the slide for 45 minutes at 2 µg/ml in a supercocktail (containing 1% BSA and 1% ovalbumin also in this case). A second antibody, goat anti-mouse fluorescein conjugate, was then added at 2 µg/ml in the supercocktail buffer, and allowed to incubate for 2 hours.

The results of this experiment were plotted as fluorescence intensity as a function of position. This image was taken at 10 µm steps and showed that not only can deprotection be carried out in a well defined pattern, but also that (1) the method provided for successful coupling of peptides to the surface of the substrate, (2) the surface of a bound peptide was available for binding with an antibody, and (3) the detection apparatus capabilities were sufficient to detect binding of a receptor. Moreover, the Herz antibody is a sequence specific reagent which may be used advantageously as a sequence specific recognition reagent. It may be used, if specificity is high, for sequencing purposes, and, at least, for fingerprinting and mapping uses.

10. Monomer-by-monomer Formation of YGGFL and Subsequent Exposure to Labeled Antibody Monomer-by-monomer synthesis of YGGFL and GGFL in alternate squares was performed on a slide in a checkerboard pattern and the resulting slide was exposed to the Herz antibody.

A slide is derivatized with the aminopropyl group, protected in this case with t-BOC (t-butoxycarbonyl). The slide was treated with TFA to remove the t-BOC protecting group. E-aminocaproic acid, which was t-BOC protected at its amino group, was then coupled onto the aminopropyl groups. The aminocaproic acid serves as a spacer between the aminopropyl group and the peptide to be synthesized. The amino end of the spacer was deprotected and coupled to NVOC-leucine. The entire slide was then illuminated with 12 mW of 325 nm broadband illumination. The slide was then coupled with NVOC-phenylalanine and washed. The entire slide was again illuminated, then coupled to NVOC-glycine and washed. The slide was again illuminated and coupled to NVOC-glycine to form the sequence shown in the last portion of FIG. 13A of Pirrung et al. (1992) U.S. Pat. No. 5,143,854.

Alternating regions of the slide were then illuminated using a projection print using a 500×500 µm checkerboard mask; thus, the amino group of glycine was exposed only in the lighted areas. When the next coupling chemistry step was carried out, NVOC-tyrosine was added, and it coupled only at those spots which had received illumination. The entire slide was then illuminated to remove all the NVOC groups, leaving a checkerboard of YGGFL in the lighted areas and in the other areas, GGFL. The Herz antibody (which recognizes the YGGFL, but not GGFL) was then added, followed by goat anti-mouse fluorescein conjugate.

The resulting fluorescence scan showed dark areas containing the tetrapeptide GGFL, which is not recognized by the Herz antibody (and thus there is no binding of the goat anti-mouse antibody with fluorescein conjugate), and red areas in which YGGFL was present. The YGGFL pentapeptide is recognized by the Herz antibody and, therefore, there is antibody in the lighted regions for the fluorescein-conjugated goat anti-mouse to recognize.

Similar patterns for a 50 um mask used in direct contact ("proximity print") with the substrate provided a pattern which was more distinct and the corners of the checkerboard pattern were touching as a result of the mask being placed in direct contact with the substrate (which reflects the increase in resolution using this technique).

11. Monomer-by-monomer Synthesis of YGGFL and PGGFL

A synthesis using a 50 µm checkerboard mask was conducted. However, P was added to the GGFL sites on the substrate through an additional coupling step. P was added by exposing protected GGFL to light through a mask, and subsequence exposure to P in the manner set forth above. Therefore, half of the regions on the substrate contained YGGFL and the remaining half contained PGGFL.

The fluorescence plot for this experiment showed the regions are again readily discernable between those in which binding did and did not occur. This experiment demonstrated that antibodies are able to recognize a specific sequence and that the recognition is not length-dependent.

12. Monomer-by-monomer Synthesis of YGGFL and YPGGFL

In order to further demonstrate the operability of the invention, a 50 µm checkerboard pattern of alternating YGGFL and YPGGFL was synthesized on a substrate using techniques like those set forth above. The resulting fluorescence plot showed that the antibody was clearly able to recognize the YGGFL sequence and did not bind significantly at the YPGGFL regions.

13. Synthesis of an Array of Sixteen Different Amino Acid Sequences and Estimation of Relative Binding Affinity to Herz Antibody Using techniques similar to those set forth above, an array of 16 different amino acid sequences (replicated four times) was synthesized on each of two glass substrates. The sequences were synthesized by attaching the sequence NVOC-GFL across the entire surface of the slides. Using a series of masks, two layers of amino acids were then selectively applied to the substrate. Each region had dimensions of 0.25 cm×0.0625 cm. The first slide contained amino acid sequences containing only L- amino acids while the second slide contained selected D- amino acids. Various regions on the first and second slides, were duplicated four times on each slide. The slides were then exposed to the Herz antibody and fluorescein-labeled goat anti-mouse antibodies.

A fluorescence plot of the first slide, which contained only L- amino acids showed red areas (indicating strong binding, i.e., 149,000 counts or more) and black areas (indicating little or no binding of the Herz antibody, i.e., 20,000 counts or less). The sequence YGGFL was clearly most strongly recognized. The sequences YAGFL and YSGFL also exhibited strong recognition of the antibody. By contrast, most of the remaining sequences showed little or no binding. The four duplicate portions of the slide were extremely consistent in the amount of binding shown therein.

A fluorescence plot of the D- amino acid slide indicated that strongest binding was exhibited by the YGGFL sequence. Significant binding was also detected to YaGFL, YsGFL, and YpGFL. The remaining sequences showed less binding with the antibody. Low binding efficiency of the sequence yGGFL was observed.

Table 6 lists the various sequences tested in order of relative fluorescence, which provides information regarding relative binding affinity.

TABLE 6

Apparent Binding to Herz Ab

| L- a.a. Set | D- a.a. Set |
| --- | --- |
| YGGFL | YGGFL |
| YAGFL | YaGFL |
| YSGFL | YsGFL |
| LGGFL | YpGFL |
| FGGFL | fGGFL |
| YPGFL | yGGFL |
| LAGFL | faGFL |
| FAGFL | wGGFL |
| WGGFL | yaGFL |
|  | fpGFL |
|  | waGFL |

14. Illustrative Alternative Embodiment

According to an alternative embodiment of the invention, the methods provide for attaching to the surface a caged binding member which, in its caged form, has a relatively low affinity for other potentially binding species, such as receptors and specific binding substances. Such techniques are more fully described in copending application Ser. No. 404,920, filed Sep. 8, 1989, and incorporated herein by reference for all purposes. See also Ser. No. 07/435,316, now abandoned, and Barrett et al. (1993) U.S. Pat. No. 5,252,743, each of which is hereby incorporated herein by reference.

According to this alternative embodiment, the invention provides methods for forming predefined regions on a surface of a solid support, wherein the predefined regions are capable of immobilizing receptors. The methods make use of caged binding members attached to the surface to enable selective activation of the predefined regions. The caged binding members are liberated to act as binding members ultimately capable of binding receptors upon selective activation of the predefined regions. The activated binding members are then used to immobilize specific molecules such as receptors on the predefined region of the surface. The above procedure is repeated at the same or different sites on the surface so as to provide a surface prepared with a plurality of regions on the surface containing, for example, the same or different receptors. When receptors immobilized in this way have a differential affinity for one or more ligands, screenings and assays for the ligands can be conducted in the regions of the surface containing the receptors.

The alternative embodiment may make use of novel caged binding members attached to the substrate. Caged (unactivated) members have a relatively low affinity for receptors of substances that specifically bind to uncaged binding members when compared with the corresponding affinities of activated binding members. Thus, the binding members are protected from reaction until a suitable source of energy is applied to the regions of the surface desired to be activated. Upon application of a suitable energy source, the caging groups labilize, thereby presenting the activated binding member. A typical energy source will be light.

Once the binding members on the surface are activated they may be attached to a receptor. The receptor chosen may be a monoclonal antibody, a nucleic acid sequence, a drug receptor, etc. The receptor will usually, though not always, be prepared so as to permit attaching it, directly or indirectly, to a binding member. For example, a specific binding substance having a strong binding affinity for the binding member and a strong affinity for the receptor or a conjugate of the receptor may be used to act as a bridge between binding members and receptors if desired. The method uses a receptor prepared such that the receptor retains its activity toward a particular ligand.

Preferably, the caged binding member attached to the solid substrate will be a photoactivatable biotin complex, i.e., a biotin molecule that has been chemically modified with photoactivatable protecting groups so that it has a significantly reduced binding affinity for avidin or avidin analogs than does natural biotin. In a preferred embodiment, the protecting groups localized in a predefined region of the surface will be removed upon application of a suitable source of radiation to give binding members, that is biotin or a functionally analogous compound having substantially the same binding affinity for avidin or avidin analogs as does biotin.

In another preferred embodiment, avidin or an avidin analog is incubated with activated binding members on the surface until the avidin binds strongly to the binding members. The avidin so immobilized on predefined regions of the surface can then be incubated with a desired receptor or conjugate of a desired receptor. The receptor will preferably be biotinylated, e.g., a biotinylated antibody, when avidin is immobilized on the predefined regions of the surface. Alternatively, a preferred embodiment will present an avidin/biotinylated receptor complex, which has been previously prepared, to activated binding members on the surface.

II. Fingerprinting

The above section on generation of reagents for sequencing provides specific reagents useful for fingerprinting applications. Fingerprinting embodiments may be applied towards polynucleotide fingerprinting, polypeptide fingerprinting, cell and tissue classification, cell and tissue temporal development stage classification, diagnostic tests, forensic uses for individual identification, classification of organisms, and genetic screening of individuals. Mapping applications are also described below.

A. Polynucleotide Fingerprint

Polynucleotide fingerprinting may use reagents similar to those described above for probing a sequence for the presence of specific subsequences found therein. Typically, the subsequences used for fingerprinting will be longer than the sequences used in oligonucleotide sequencing. In particular, specific long segments may be used to determine the similarity of different samples of nucleic acids. They may also be used to fingerprint whether specific combinations of information are provided therein. Particular probe sequences are selected and attached in a positional manner to a substrate. The means for attachment may be either using a caged biotin method described, e.g., in Barrett et al. (1993) U.S. Pat. No. 5,242,743, or by another method using targeting molecules. For example, a short polypeptide of specific sequence may be attached to an oligonucleotide and targeted to specific positions on a substrate having antibodies attached thereto, the antibodies exhibiting specificity for binding to those short peptide sequences. In another embodiment, an unnatural nucleotide or similar complementary binding molecule may be attached to the fingerprinting probe and the probe thereby directed towards complementary sequences on-a VLSIPS substrate. Typically, unnatural nucleotides would be preferred, e.g., unnatural optical isomers, which would not interfere with natural nucleotide interactions.

Having produced a substrate with particular fingerprint probes attached thereto at positionally defined regions, the substrate may be used in a manner quite similar to the sequencing embodiment to provide information as to whether the fingerprint probes are detecting the corresponding sequence in a target sequence. This will often provide information similar to a Southern blot hybridization.

B. Polypeptide Fingerprint

A polypeptide fingerprint may be performed using antibodies which recognize specific antigens on the polypeptide. For example, monoclonal antibodies which recognize specific sequences or antigens on a polypeptide may be used to determine whether those epitopes are found on a particular protein. For example, particular patterns of epitopes would be found on various types of proteins. This will lead to the discovery that specific epitopes, or antigenic determinants, which are characteristic of, e.g., beta sheet segments, will be identified as will particular different types of domains in various protein types. Thus, a screening method may be devised which can classify polypeptides, either native or denatured, into various new classes defined by the epitopes existing thereon.

In addition, once the substrate is generated in the manners described above, a target peptide is exposed to the substrate. The target may be either native or denatured, though the conditions used to denature the polypeptide may interfere with the specific interaction between the polypeptide and the recognition reagent. This method is not dependent on the fact that the polypeptide is a single chain, thus protein complexes may also be fingerprinted using this methodology. Structures such as multi-subunit proteins, associations of proteins, ribosomes, nucleosomes, and other small cellular structures may also be fingerprinted and classified according to the presence of specific recognizable features thereon.

Peptide fingerprinting may be useful, for example, in correlating with particular physiological conditions or developmental stages of a cell or organism. Thus, a biological sample may be fingerprinted to determine the presence in that sample of a plurality of different polypeptides which are each individually fingerprinted. In an alternative embodiment, a polypeptide itself is not fingerprinted but a biological sample is fingerprinted searching for specific epitopes, e.g., polypeptide, carbohydrate, nucleic acid, or any of a number of other specific recognizable structural features.

The conditions for the interactions using antibodies is described, e.g., in Harlow and Lane (1988) *Antibodies: A Laboratory Manual*, Cold Spring Harbor Press, New York. The conditions should be titrated for temperature, buffer composition, time, and other important parameters in an antibody interaction.

C. Cell Classification Scheme

The present invention can be used for cell classification using fingerprinting type technology as described above in the polypeptide fingerprint. Classes of cells are typically defined by the presence of common functions which are usually reflected by structural features. Thus, a plant cell is classified differently from an animal cell by a number of structural features. Given an unknown cell, the present invention provides improved means for distinguishing the different cell types. Once a cell classification scheme is developed and the structural features which define it are identified using the present invention, homogeneous cell population expressing these features may be separated from others. Standard cell sorters may be coupled with recognition reagents and labels which can distinguish various cell types.

a. T-Cell Classes

T-cell classes are defined on the basis of expression of particular antigens characteristic of each class. For example, mouse T-cell differentiation markers include the LY antigens. With the plurality of different antigens which may be tested using antibody or other recognition reagents, new populations and classes of cells may be defined. For example, different neural cell types may be defined on the basis of cell surface antigens. Different tissue types will be defined on the basis of tissue specific antigens. Developmental cell classes will be similarly defined. All of these screenings can make use of the VLSIPS substrates with specific recognition molecules attached thereto. The substrates are exposed to the cell types directly, assaying for attachment of cells to specific regions, or are exposed to products of a population of cells, e.g., a supernatant, or a cell lysate.

Once a cell classification scheme has been correlated with specific structural markers therein, reagents which recognize those features may be developed and used in a fluorescence activated cell sorter as described, e.g., in Dangl, J. and Herzenberg (1982) *J. Immunological Methods* 52: 1–14; and Becton Dickinson, Fluorescence Activated Cell Sorters Division, San Jose, Calif. This will provide a homogeneous population of cells whose function has been defined by structure.

b. B-Cell Classes

The present cell classification scheme may also be used to determine specific B-cell classes. For example, B-cells specific for producing IgM, IgG, IgD, IgE, and IgA may be defined by the internal expression of specific mRNA sequences encoding each type of immunoglobulin. The classification scheme may depend on either extracellularly expressed markers which are correlated as being diagnostic of specific stages in development, or intracellular mRNA sequences which indicate particular functions.

D. Temporal Development Scheme

1. Developmental Antigens

The present fingerprinting invention also allows cell classification by expression of developmental antigens. For example, a lymphocyte stem cell expresses a particular combination of antigens. As the lymphocyte develops through a program developmental scheme, at various stages it expresses particular antigens which are diagnostic of particular stages in development. Again, the fingerprinting methodology allows for the definition of specific structural features which are diagnostic of developmental or functional features which will allow classification of cells into temporal developmental classes. Cells, products of those cells, or lysates of those cells will be assayed to determine the developmental stage of the source cells. In this manner, once a developmental stage is defined, specific synchronized populations of cells will be selected out of another population. These synchronized populations may be very important in determining the biological mechanisms of development.

2. Developmental mRNA Expression

Besides expressed antigens, the present invention also allows for fingerprinting of the mRNA population of a cell. In this fashion, the mRNA population, which should be a good determinant of developmental stage, will be correlated with other structural features of the cell. In this manner, cells at specific developmental stages will be characterized by the intracellular environment, as well as the extracellular environment. The present invention also allows the combination of definitions based, in part, upon antigens and, in part, upon mRNA expression.

In one embodiment, the two may be combined in a single incubation step. A particular incubation condition may be found which is compatible with both hybridization recognition and non-hybridization recognition molecules. Thus, e.g., an incubation condition may be selected which allows both specificity of antibody binding and specificity of nucleic acid hybridization. This allows simultaneous performance of both types of interactions on a single matrix. Again, where developmental mRNA patterns are correlated with structural features, or with probes which are able to hybridize to intracellular mRNA populations, a cell sorter may be used to sort specifically those cells having desired mRNA population patterns.

E. Diagnostic Tests

The present invention also provides the ability to perform diagnostic tests. Diagnostic tests typically are based upon a fingerprint type assay, which tests for the presence of specific diagnostic structural features. Thus, the present invention provides means for viral strain identification, bacterial strain identification, and other diagnostic tests using positionally defined specific reagents. The present invention also allows for determining a spectrum of allergies, diagnosing a biological sample for any or all of the above, and testing for many other conditions.

1. Viral Identification

The present invention provides reagents and methodology for identifying viral strains. The specific reagents may be either antibodies or recognition proteins which bind to specific viral epitopes preferably surface exposed, but may make use of internal epitopes, e.g., in a denatured viral sample. In an alternative embodiment, the viral genome may be probed for specific sequences which are characteristic of particular viral strains. As above, a combination of the two may be performed simultaneously in a single interaction step, or in separate tests, e.g., for both genetic characteristics and epitope characteristics.

2. Bacterial Identification

Similar techniques will be applicable to identifying a bacterial source. This may be useful in diagnosing bacterial infections, or in classifying sources of particular bacterial species. For example, the bacterial assay may be useful in determining the natural range of survivability of particular strains of bacteria across regions of the country or in different ecological niches.

3. Other Microbiological Identifications

The present invention provides means for diagnosis of other microbiological and other species, e.g., protozoal species and parasitic species in a biological sample, but also provides the means for assaying a combination of different infections. For example, a biological specimen may be assayed for the presence of any or all of these microbiological species. In human diagnostic uses, typical samples will be blood, sputum, stool, urine, or other samples.

4. Allergy Tests

An immobilized set of antigens may be attached to a solid substrate and, instead of the standard skin reaction tests, a blood sample may be assayed on such a substrate to determine the presence of antibodies, e.g., IgE or other type antibodies, which may be diagnostic of an allergic or immunological susceptibility. A standard radioallergosorbent test (RAST) may be used to check a much larger population of antigens.

In addition, an allergy like test may be used to diagnose the immunological history of a particular individual. For example, by testing the circulating antibodies in a blood sample, which reflects the immunological history and memory of an individual, it may be determined what infections may not have been historically presented to the immune system. In this manner, it may be possible to specifically supplement an immune system for a short period of time with IgG fractions made up of specific types of gamma globulins. Thus, hepatitis gamma globulin injections may be better designed for a particular environment to which a person is expected to be exposed. This also provides the ability to identify genetically equivalent individuals who have immunologically different experiences. Thus, a blood sample from an individual who has a particular combination of circulating antibodies will likely be different from the combination of circulating antibodies found in a genetically similar or identical individual. This could allow for the distinction between clones of particular animals, e.g., mice, rats, or other animals.

F. Individual Identification

The present invention provides the ability to fingerprint and identify a genetic individual. This individual may be a bacterial or lower microorganism, as described above in diagnostic tests, or of a plant or animal. An individual may be identified genetically or immunologically, as described.

1. Genetic

Genetic fingerprinting has been utilized in comparing different related species in Southern hybridization blots. Genetic fingerprinting has also been used in forensic studies, see, e.g., Morris et al. (1989) *J. Forensic Science* 34: 1311–1317, and references cited therein. As described above, an individual may be identified genetically by a sufficiently large number of probes. The likelihood that another individual would have an identical pattern over a sufficiently large number of probes may be statistically negligible. However, it is often quite important that a large number of probes be used where the statistical probability of matching is desired to be particularly low. In fact, the probes will optimally be selected for having high heterogeneity among the population. In addition, the fingerprint method may make use of the pattern of homologies indicated by a series of more and more stringent washes. Then, each position has both a sequence specificity and a homology measurement, the combination of which greatly increases the number of dimensions and the statistical likelihood of a perfect pattern match with another genetic individual.

2. Immunological

As indicated above in the diagnostic tests, it is possible to identify a particular immune system within a genetically homogeneous class of organisms by virtue of their immunological history. For example, a large colony of cloned mice may be distinguishable by virtue of each immunological history. For example, one mouse may have had an immunological response to exposure to antigen A to which her genetically identical sibling may have not been exposed. By virtue of this differential history, the first of the pair will likely have a high antibody titer against the antigen A whereas her genetically identical sibling will have not had a response to that antigen by virtue of never having been exposed to it. For this reason, immune systems may be identified by their immunological memories. Thus, immunological experience may also be a means for identifying a particular individual at a particular moment in her lifetime.

This same immunological screening may be used for other sorts of identifiable biological products. For example, an individual may be identified by her combination of expressed proteins. These proteins may reflect a physiological state of the individual, and would thus be useful in certain circumstances where diagnostic tests may be performed. For example, an individual may be identified, in part, by the presence of particular metabolic products.

In fact, a plant origin may be determined by virtue of having within its genome an unnatural sequence introduced to it by genetic breeders. Thus, a marker nucleic acid sequence may be introduced as a means to determine whether a genetic strain of a plant or animal originated from another particular source.

G. Genetic Screening

1. Test Alleles with Markers

The present invention provides for the ability to screen for genetic variations of individuals. For example, a number of genetic diseases are linked with specific alleles. See, e.g., Scriber, C. et al. (eds.) (1989) *The Metabolic Bases of Inherited Disease*, McGraw-Hill, New York. In one embodiment, cystic fibrosis has been correlated with a specific gene, see, Gregory et al. (1990) *Nature* 347: 382–386. A number of alleles are correlated with specific genetic deficiencies. See, e.g., McKusick, V. (1990) *Genetic Inheritance in Man: Catalogs of Autosomal Dominant, Autosomal Recessive, and X-linked Phenotypes*, Johns Hopkins University Press, Baltimore; Ott, J. (1985) *Analysis of Human Genetic Linkage*, Johns Hopkins University Press, Baltimore; Track, R. et al. (1989) *Banbury Resort* 32: *DNA Technology and Forensic Science*, Cold Spring Harbor Press, New York; each of which is hereby incorporated herein by reference.

2. Amniocentesis

Typically, amniocentesis is used to determine whether chromosome translocations have occurred. The mapping procedure may provide the means for determining whether these translocations have occurred, and for detecting particular alleles of various markers.

III. Mapping

A. Positionally Located Clones

The present invention allows for the positional location of specific clones useful for mapping. For example, caged biotin may be used for specifically positioning a probe to a location on a matrix pattern.

In addition, the specific probes may be positionally directed to specific locations on a substrate by targeting. For example, polypeptide specific recognition reagents may be attached to oligonucleotide sequences which can be complementarily targeted to specific locations on a VLSIPS™ Technology substrate. Hybridization conditions, as applied for oligonucleotide probes, will be used to target the reagents to locations on a substrate having complementary oligonucleotides synthesized thereon. In another embodiment, oligonucleotide probes may be attached to specific polypeptide targeting reagents such as an antigen or antibody. These reagents can be directed towards a complementary antigen or antibody already attached to a VLSIPS substrate.

In another embodiment, an unnatural nucleotide which does not interfere with natural nucleotide complementary hybridization may be used to target oligonucleotides to particular positions on a substrate. Unnatural optical isomers of natural nucleotides should be ideal candidates.

In this way, short probes may be used to determine the mapping of long targets or long targets may be used to map the position of shorter probes. See, e.g., Craig et al. 1990 *Nuc. Acids Res.* 18: 2653–2660.

B. Positionally Defined Clones

Positionally defined clones may be transferred to a new substrate by either physical transfer or by synthetic means. Synthetic means may involve either a production of the probe on the substrate using the VLSIPS™ Technology synthetic methods, or may involve the attachment of a targeting sequence made by VLSIPS synthetic methods which will target that positionally defined clone to a position on a new substrate. Both methods will provide a substrate having a number of positionally defined probes useful in mapping.

IX. Conclusion

The present inventions provide greatly improved methods and apparatus for synthesis of polymers on substrates. It is to be understood that the above description is intended to be illustrative and not restrictive. Many embodiments will be apparent to those of skill in the art upon reviewing the above description. By way of example, the invention has been described primarily with reference to the use of photoremovable protective groups, but it will be readily recognized by those of skill in the art that sources of radiation other than light could also be used. For example, in some embodiments it may be desirable to use protective groups which are sensitive to electron beam irradiation, x-ray irradiation, in combination with electron beam lithograph, or x-ray lithography techniques. Alternatively, the group could be removed by exposure to an electric current. The scope of the invention should, therefore, be determined not with reference to the above description, but should instead be determined with reference to the appended claims, along with the full scope of equivalents to which such claims are entitled.

All publications and patent applications referred to herein are incorporated by reference to the same extent as if each individual publication or patent application was specifically and individually incorporated by reference. The present invention now being fully described, it will be apparent to one of ordinary skill in the art that many changes and modifications can be made thereto without departing from the spirit or scope of the appended claims.

What is claimed is:

1. An array comprising a solid substrate and a plurality of positionally distinguishable polynucleotides attached to the solid substrate at a density of at least 100 different polynucleotides per $cm^2$; wherein each of the attached polynucleotides comprises at least about 25 nucleotides and has a predetermined nucleotide sequence, a target complementary to at least one of the predetermined nucleotide sequences specifically binds to at least one known position on the solid substrate, and at least one of the attached polynucleotides is comprised of an unnatural nucleotide or unnatural nucleotide analogue.

2. The array of claim 1, wherein each of the positionally distinguishable polynucleotides is attached to the solid substrate within a square of less than about 10 microns by 10 microns.

3. The array of claim 1, wherein the density of positionally distinguishable polynucleotides attached to the solid substrate is at least 300 polynucleotides per $cm^2$.

4. The array of claim 1, wherein each of the attached polynucleotides comprises at least about 50 nucleotides.

5. The array of claim 1, wherein the plurality of attached polynucleotides comprises at least 3000 different polynucleotides.

6. The array of claim 1, wherein the solid substrate is glass or plastic.

7. The array of claim 1, wherein the solid substrate is a bead or fiber.

8. An array comprising a solid substrate and a plurality of positionally distinguishable polynucleotides attached to the solid substrate at a density of at least 100 different polynucleotides per $cm^2$; wherein each of the attached polynucleotides has a predetermined nucleotide sequence and at least one of the attached polynucleotides is comprised of an unnatural nucleotide or unnatural nucleotide analogue.

9. The array of claim 8, wherein each of the positionally distinguishable polynucleotides is attached to the solid substrate within a square of less than about 500 microns by 500 microns.

10. The array of claim 8, wherein each of the positionally distinguishable polynucleotides is attached to the solid substrate within a square of less than about 100 microns by 100 microns.

11. The array of claim 8, wherein each of the positionally distinguishable polynucleotides is attached to the solid substrate within a square of less than about 50 microns by 50 microns.

12. The array of claim 8, wherein each of the positionally distinguishable polynucleotides is attached to the solid substrate within a square of less than about 10 microns by 10 microns.

13. The array of claim 8, wherein the density of positionally distinguishable polynucleotides attached to the solid substrate is at least 300 polynucleotides per $cm^2$.

14. The array of claim 8, wherein the density of positionally distinguishable polynucleotides attached to the solid substrate is at least 1000 polynucleotides per $cm^2$.

15. The array of claim 8, wherein the density of positionally distinguishable polynucleotides attached to the solid substrate is at least 3000 polynucleotides per $cm^2$.

16. The array of claim 8, wherein the density of positionally distinguishable polynucleotides attached to the solid substrate is at least 10,000 polynucleotides per $cm_2$.

17. The array of claim 8, wherein the density of positionally distinguishable polynucleotides attached to the solid substrate is at least 30,000 polynucleotides per $cm^2$.

18. The array of claim 8, wherein the density of positionally distinguishable polynucleotides attached to the solid substrate is at least 100,000 polynucleotides per $cm^2$.

19. The array of claim 8, wherein each of the attached polynucleotides comprises at least about 25 nucleotides.

20. The array of claim 8, wherein each of the attached polynucleotides comprises at least about 50 nucleotides.

21. The array of claim 8, wherein the plurality of attached polynucleotides comprises at least 3000 different polynucleotides.

22. The array of claim 8, wherein the solid substrate has a surface area of less than about 4 square centimeters.

23. The array of claim 8, wherein the solid substrate has a surface area of less than about 11 $cm^2$.

24. The array of claim 8, wherein the solid substrate is glass.

25. The array of claim 8, wherein the solid substrate is plastic.

26. The array of claim 8, wherein the solid substrate is a bead.

27. The array of claim 8, wherein the solid substrate is a fiber.

* * * * *